US012466791B2

(12) United States Patent
Dai et al.

(10) Patent No.: US 12,466,791 B2
(45) Date of Patent: Nov. 11, 2025

(54) METHODS FOR SYNTHESIS OF THE TRICYCLIC PROSTAGLANDIN $D_2$ METABOLITE METHYL ESTER

(71) Applicant: Purdue Research Foundation, West Lafayette, IN (US)

(72) Inventors: Mingji Dai, Alpharetta, GA (US); Hunter Sims, Decatur, GA (US)

(73) Assignee: Purdue Research Foundation, West Lafayette, IN (US)

( * ) Notice: Subject to any disclaimer, the term of this patent is extended or adjusted under 35 U.S.C. 154(b) by 357 days.

(21) Appl. No.: 18/061,969

(22) Filed: Dec. 5, 2022

(65) Prior Publication Data

US 2023/0174477 A1 Jun. 8, 2023

Related U.S. Application Data

(60) Provisional application No. 63/285,590, filed on Dec. 3, 2021.

(51) Int. Cl.

| | |
|---|---|
| ***C07C 405/00*** | (2006.01) |
| ***C07C 67/14*** | (2006.01) |
| ***C07C 201/00*** | (2006.01) |
| ***C07D 307/935*** | (2006.01) |
| ***C07D 493/04*** | (2006.01) |

(52) U.S. Cl.
CPC .............................. *C07C 405/0075* (2013.01)

(58) Field of Classification Search
CPC ................................................ C07C 405/0075
USPC ......................................................... 549/265
See application file for complete search history.

(56) References Cited

PUBLICATIONS

Taber and Prakash et al., "Synthesis of the Major Urinary Metabolite of Prostaglandin D2", J Chem Soc Perkin Trans. 1, (1988) 2821-2826 ("Taber"); and (Year: 1988).*

Sulikowski et al., "Synthesis of a Human Urinary Metabolite of Prostaglandin D2" Org. Lett. 2019, 21, 24, 10048-10051 (Published Dec. 4, 2019) https://doi.org/10.1021/acs.orglett.9b03983 (Year: 2019).*

* cited by examiner

*Primary Examiner* — Jeffrey H Murray
*Assistant Examiner* — Grace Ching Hsu
(74) *Attorney, Agent, or Firm* — Reichel Stohry Dean LLP; Natalie J. Dean

(57) ABSTRACT

Methods for the synthesis of a tricyclic-prostaglandin $D_2$ metabolite methyl ester or a pharmaceutically acceptable salt thereof.

6 Claims, 46 Drawing Sheets prostaglandin D2 ($PGD_2$, 1)

tricyclic-PGDM (2)

4
Taber (1988)
26 steps
(17 steps from 4)
5 mg

5
Sulikowski (2019)
19 steps
(13 steps from 5)
1 mg tricyclic-PGDM methyl ester (3)
lack of material supply

6
18
19
17
16
20
21 tricyclic-PGDM methyl ester

Ru-Z-Mes
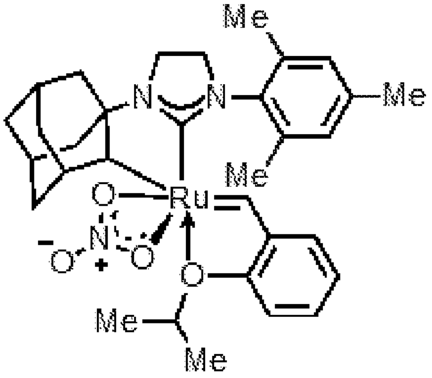
Ru-Z-DIPP
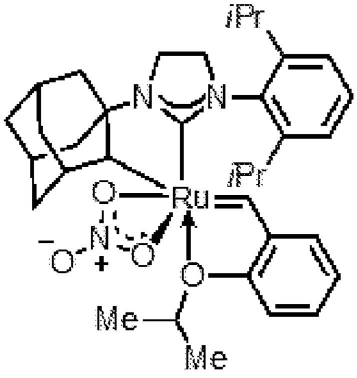
From Sigma-Aldrich (repurified)
From Professor Grubbs
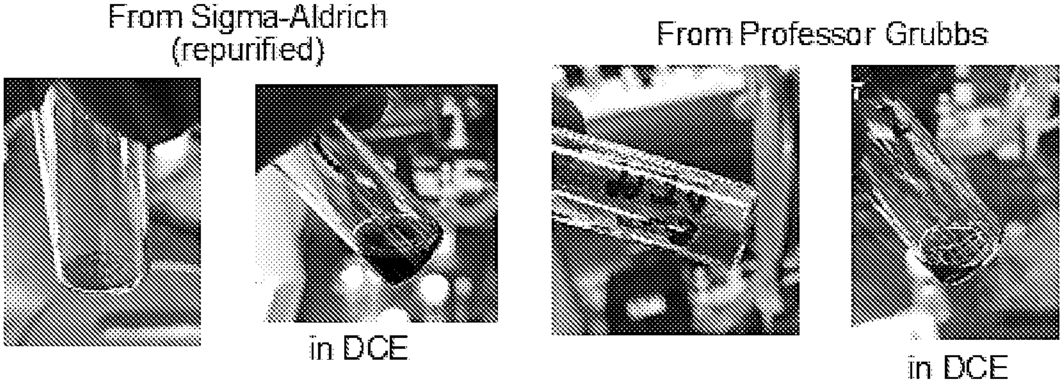
*FIG. 6A*
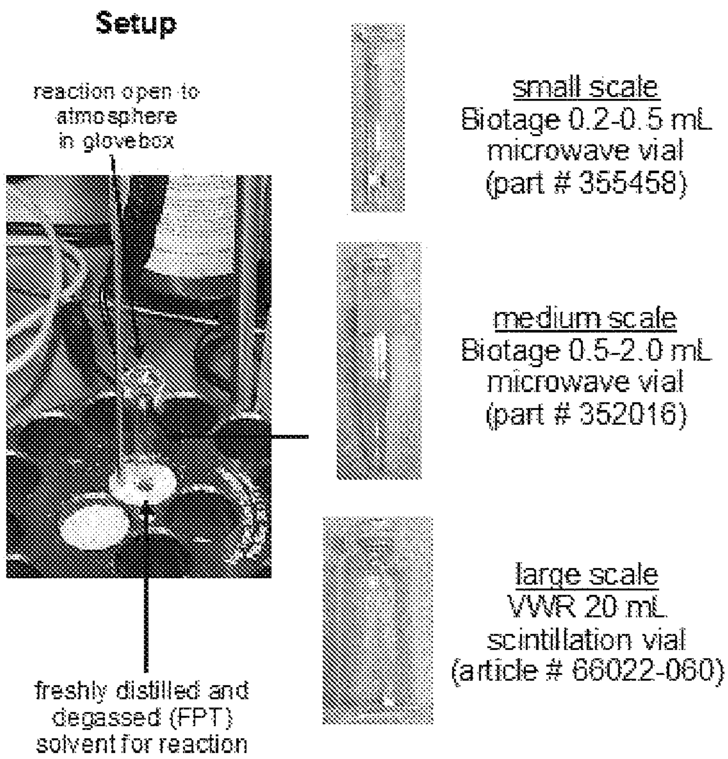
*FIG. 6B*

FIG. 7

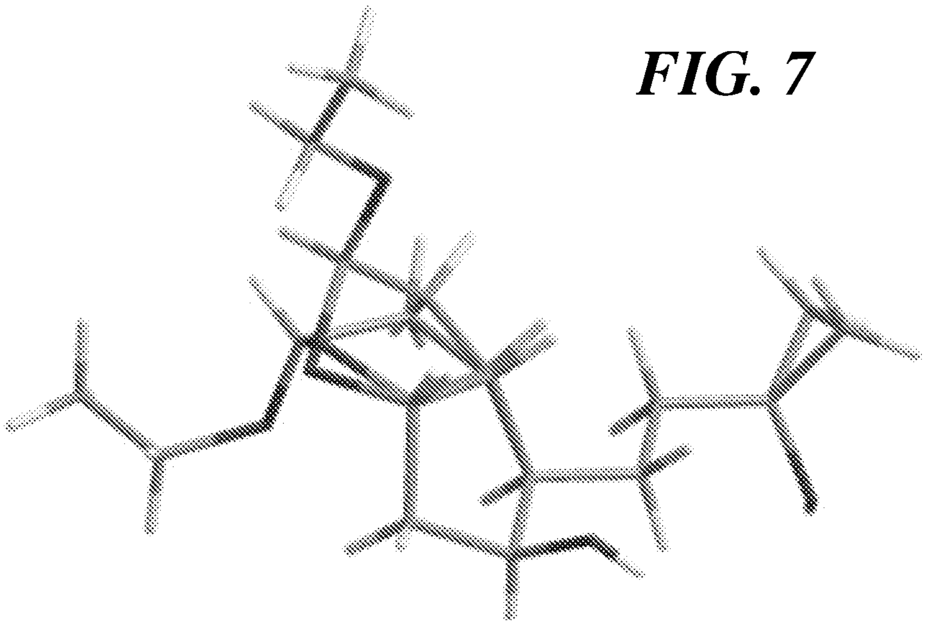

Bond precision: C-C = 0.0046 A Wavelength=1.54178

Cell. a=15.137(3) b=7.8516(11) c=11.998(2)
alpha=90 beta=103.523(13) gamma=90

Temperature: 150 K

| | Calculated | Reported |
|---|---|---|
| Volume | 1386.4(4) | 1386.5(4) |
| Space group | P 21/c | P 21/c |
| Hall group | -P 2ybc | -P 2ybc |
| Moiety formula | C14 H24 O4 | ? |
| Sum formula | C14 H24 O4 | C14 H24 O4 |
| Mr | 256.33 | 256.33 |
| Dx,g cm-3 | 1.228 | 1.228 |
| Z | 4 | 4 |
| Mu (mm-1) | 0.718 | 0.718 |
| F000 | 560.0 | 560.0 |
| F000' | 561.74 | |
| h,k,lmax | 19,10,15 | 19,9,15 |
| Nref | 3018 | 2898 |
| Tmin,Tmax | 0.891,0.986 | 0.589,0.754 |
| Tmin' | 0.891 | |

Correction method= # Reported T Limits: Tmin=0.589 Tmax=0.754
AbsCorr = MULTI-SCAN Data completeness= 0.960 Theta(max)= 79.868

R(reflections)= 0.0832( 1643) wR2(reflections)= 0.2642( 2898)

S = 1.071 Npar= 242

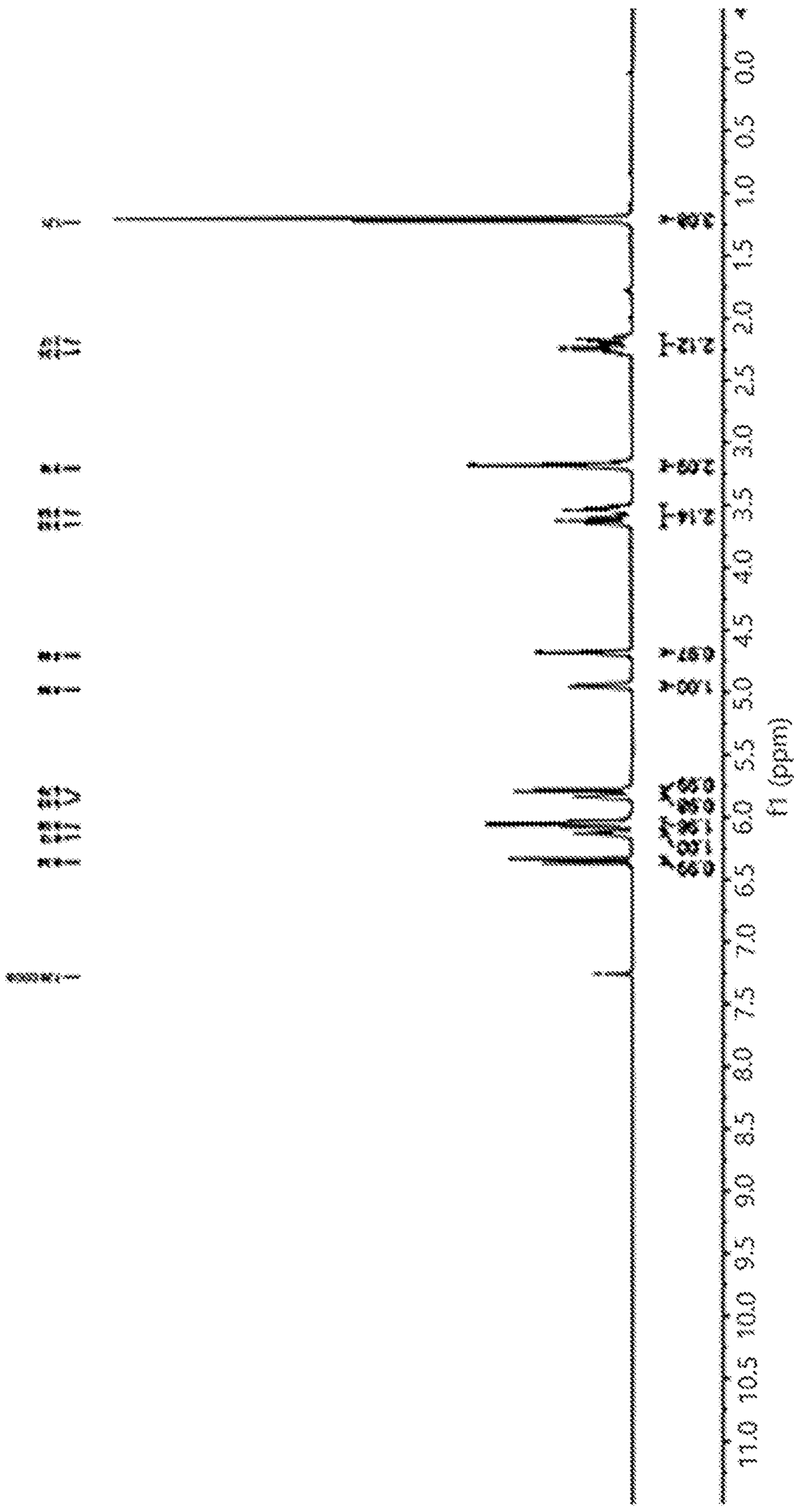
*FIG. 8 cont.*
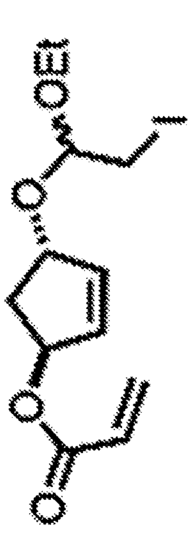
$^1$H-NMR (500 MHz, $CDCl_3$)

$^{13}C$-NMR (125 MHz, $CDCl_3$)

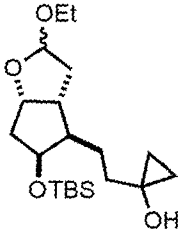
$^1$H-NMR (500 MHz, $CDCl_3$)
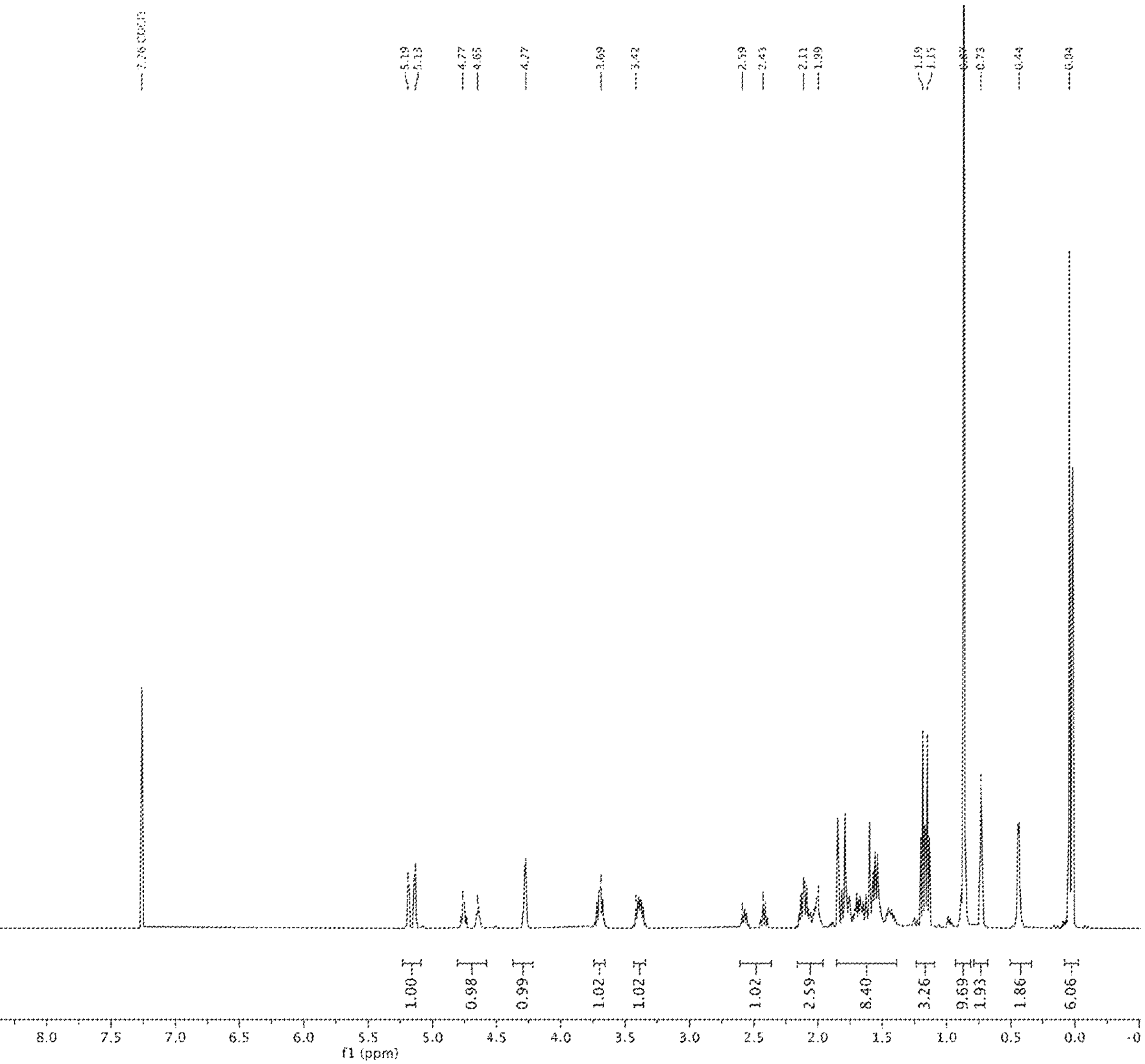
FIG. 8 cont.

$^1$H-NMR (500 MHz, $CDCl_3$)

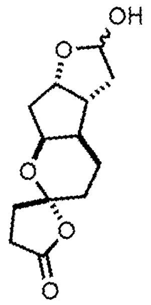
unstable intermediate
$^{13}$C-NMR (125 MHz, $CDCl_3$)
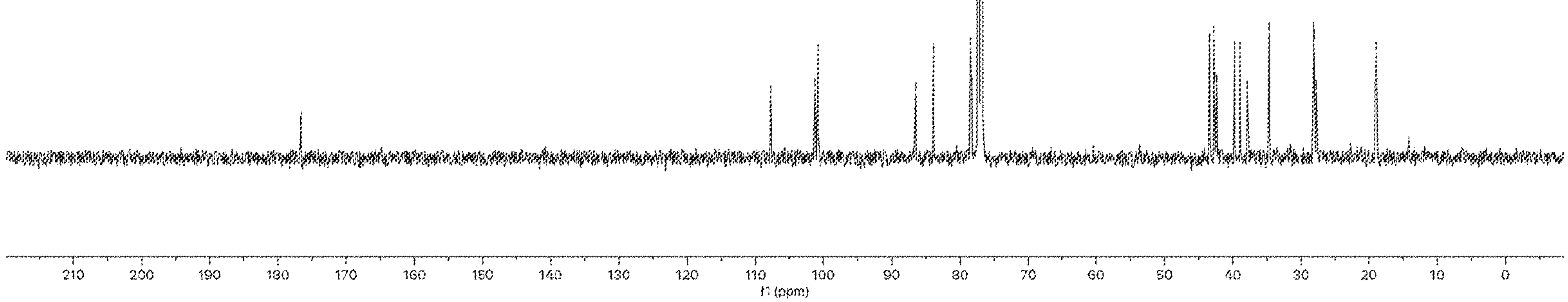
FIG. 8 cont.

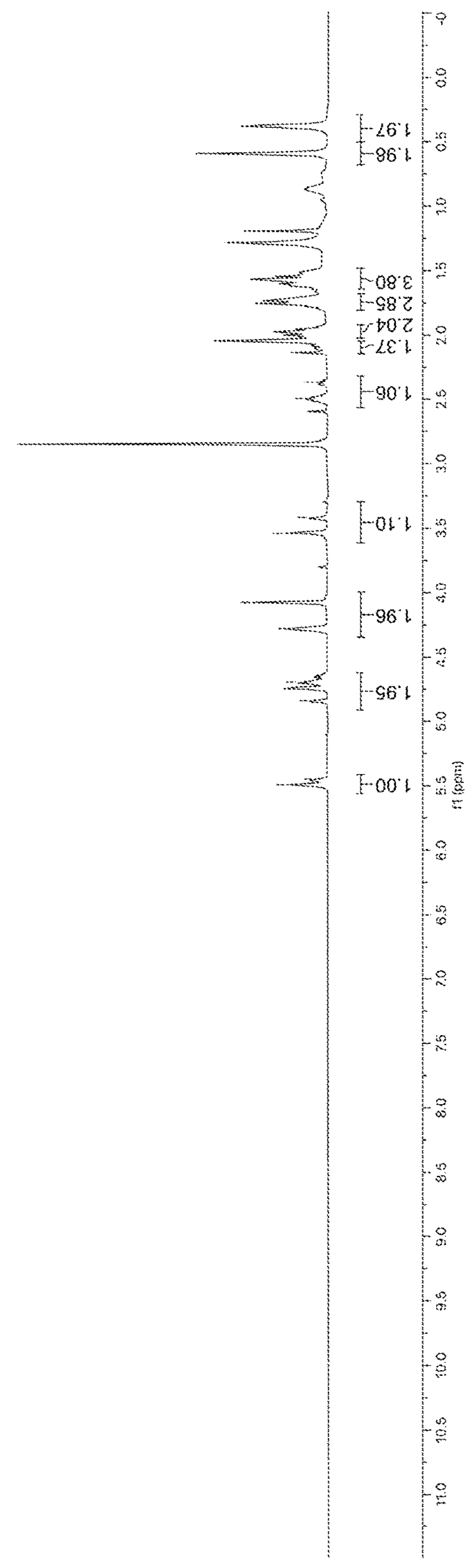
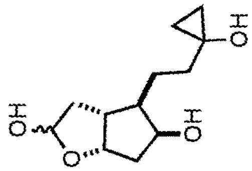
unstable intermediate
$^1$H-NMR (500 MHz, $(CD_3)_2CO$)
FIG. 8 cont.

$^1$H-NMR (500 MHz, $CDCl_3$)

$^{13}C$-NMR (125 MHz, $CDCl_3$)

$^{13}C$-NMR (125 MHz, $CDCl_3$)

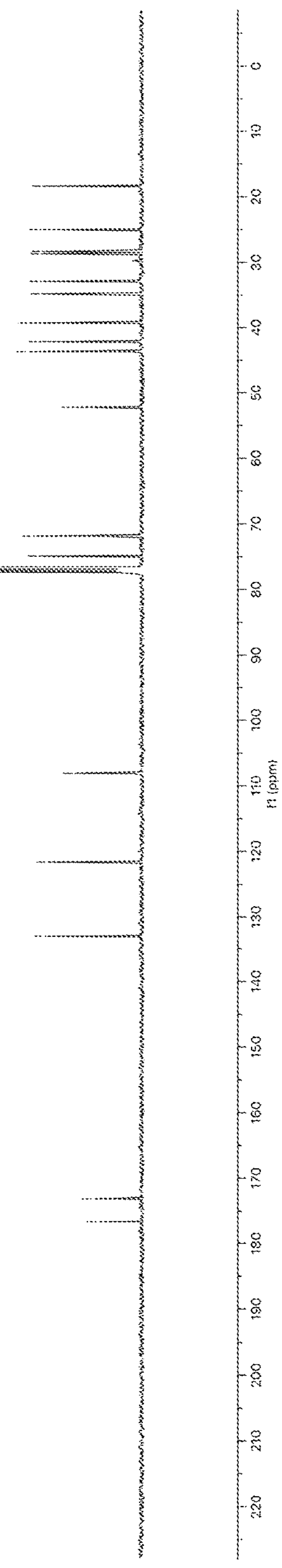
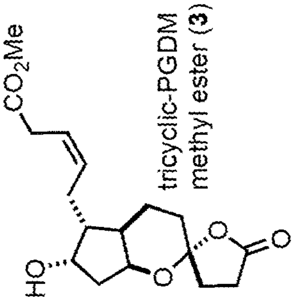
tricyclic-PGDM methyl ester (3)
$^{13}$C-NMR (125 MHz, $CDCl_3$)
*FIG. 8 cont.*

$^1$H-NMR (500 MHz, $C_6D_6$)

$^{13}$C-NMR (125 MHz, $C_6D_6$)

METHODS FOR SYNTHESIS OF THE TRICYCLIC PROSTAGLANDIN $D_2$ METABOLITE METHYL ESTER

RELATED APPLICATIONS

This application is related to and claims the priority benefit of U.S. Provisional Application No. 63/285,590, filed Dec. 3, 2021. The content of the aforementioned application is hereby incorporated by reference herein in its entirety.

STATEMENT OF GOVERNMENT INTEREST

This invention was made with government support under Award No. CHE2102022 awarded by the National Science Foundation (NSF). The government has certain rights in the invention.

TECHNICAL FIELD

The present disclosure relates to catalysis-enabled methods of concise total synthesis of the tricyclic prostaglandin $D_2$ metabolite methyl ester.

BACKGROUND OF THE INVENTION

This section introduces aspects that may help facilitate a better understanding of the disclosure. Accordingly, these statements are to be read in this light and are not admissions about what is or is not prior art.

Prostaglandins are signaling molecules that play a pivotal role in numerous biological pathways. A range of chemical and physical stimuli can activate their biosynthesis, which progresses through an enzymatic cascade involving phospholipase-mediated release of arachidonic acid (AA) from the membrane. Upon release, AA is transformed by cyclooxygenase (COX) enzymes to prostaglandin $H_2$ ($PGH_2$), a common intermediate that gives rise to the four principal prostaglandins by tissue specific isomerases.

Prostaglandins serve a crucial regulatory function in the acute inflammatory response. However, upregulation of these pathways spontaneously or extending beyond an initial inflammation event can be detrimental and has been linked to multiple diseases. In addition, other unique non-inflammatory roles of prostaglandins continue to emerge, which further demonstrates that these scaffolds hold a privileged position as biological mediators.

In view of this, it is to no surprise that the development of sensitive detection methods for prostaglandins has been an active research area. By virtue of their short half-lives, most conventional methods rely on the detection of metabolites that can be traced to the prostaglandin of interest.

Following its recognition as the major urinary metabolite of prostaglandin $D_2$ ($PGD_2$, 1 in FIG. 1), tricyclic-$PGD_2$ metabolite (PGDM) (2 in FIG. 1) has been used as a valuable indicator for $PGD_2$ overproduction. More specifically, an assay for tricyclic-PGDM quantification was developed that uses $^{18}O$-labelling and fully synthetic tricyclic-PGDM methyl ester (3 in FIG. 1). While this assay has been a valuable tool in clinical settings, limitations on the availability of fully synthetic tricyclic-PGDM methyl ester (3 in FIG. 1) has prevented this assay from becoming more prevalent.

Prostaglandin molecules and their metabolites have garnered a tremendous amount of interest and efforts from the synthetic community. The complexity of tricyclic-PGDM methyl ester arises from the four contiguous stereocenters on the central cyclopentane ring, the labile oxaspirolactone, and the (Z)-3-butenoate side chain.

In 1988, Taber and coworkers achieved the first synthesis of (±)-tricyclic-PGDM in 17 steps from the Corey lactone (see compound 4 in FIG. 1), with their final step giving 5 mg of tricyclic-PGDM for the clinical assay. Prackash et al., Synthesis of the major urinary metabolite of prostaglandin $D_2$, J. Chemical Soc'y Perkin Transactions 1 10: 2821-2826 (1988). In Taber's synthesis, the (Z)-3-butenoate side chain proved to be troublesome to install on a hemi-acetal intermediate, with β-phosphoranylidene esters being noncompatible with the Wittig reaction. They overcame this issue by using an orthoester phosphorane. Corey & Shimoji, Total synthesis of the major human urinary metabolite of prostaglandin $D_2$, a key diagnostic indicator, J. Am. Chemical Soc'y 105(6): 1662-1664 (1983). To complete the synthesis, an acid-catalyzed cyclization of a hydroxy ketoacid was used to install the oxaspirolactone. However, while they could produce tricyclic-PGDM, overall yield was low, and the synthesis required 17 steps (not counting the 9 steps required to prepare the initial compound (Corey lactone (4 in FIG. 1)).

More recently, Sulikowski and coworkers developed the second synthesis of (±)-tricyclic-PGDM from the known α-iodoenone (5 in FIG. 1) in 13 steps, with their final step yielding 1 mg of tricyclic-PGDM (3 in FIG. 1). Kimbrough et al., A synthesis of a human urinary metabolite of prostaglandin $D_2$, Organic Letters 21(24): 10048-10051 (2019). Their route featured a Lindlar reduction of a β-alkynyl ester to install the (Z)-3-butenoate side chain (albeit in low yield) and an acid-promoted spiroketalization to afford the oxaspirolactone. Again, overall yield was low and this process requires 13 steps in addition to the 6 steps required to prepare the starting compound α-iodoenone (5).

What is needed is a simple and concise process for synthesizing tricyclic-PGDM methyl ester from readily available components.

SUMMARY OF THE INVENTION

Methods for synthesis of a tricyclic-prostaglandin $D_2$ metabolite (PGDM) methyl ester or a pharmaceutically acceptable salt thereof are provided. In certain embodiments, the method comprises: subjecting an iodo-acetal compound to a cyclization reaction with a methyl ester to provide a cyclization product; reacting the cyclization product with a catalyst and a dialkyldialkoxytitanium reagent under conditions sufficient to produce a cyclopropanol compound; hydrolyzing the cyclopropanol compound to form a hemi-acetal compound; reacting the hemi-acetal compound under suitable Wittig reaction or olefination conditions to provide an olefin compound; subjecting the olefin compound to a carbonylative spirolactonization reaction to produce a compound having an oxaspirolactone moiety, the compound having the structure; and reacting a molecule having a terminal olefin with the compound having an oxaspirolactone moiety and a Z-selective catalyst under conditions suitable for a Z-selective cross metathesis reaction to produce tricyclic-PGDM methyl ester or a pharmaceutically acceptable salt thereof.

Embodiments of the aforementioned method can further comprise providing a first compound having the structure of the following formula:

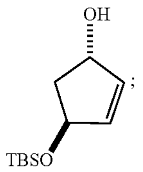 [SMILES: CC(C)(C)[Si](C)(C)O[C@@H]1C=C[C@@H](O)C1]

and converting the first compound to the iodo-acetal compound and deprotecting a silyl ether moiety thereof; wherein the olefin compound provided by the Wittig reaction or olefination has the structure:

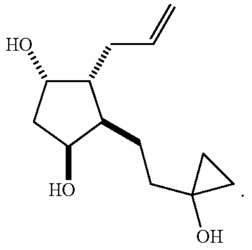 [SMILES: C=CC[C@@H]1[C@@H](CCC2(O)CC2)[C@@H](O)C[C@@H]1O]

Deprotecting a silyl ether moiety can comprise subjecting the iodo-acetal compound to tetra-n-butylammonium fluoride (TBAF) in the presence of an anhydrous organic solvent.

Subjecting the iodo-acetal compound to a cyclization reaction can comprise reacting the iodo-acetal compound and the methyl ester with a radical initiator, a reducing agent, and an alcohol in solution to produce the cyclization product. In certain embodiments, the radical initiator is 2,2'-azobis(2-methylpropionitrile) (AIBN). In certain embodiments, the reducing agent is sodium cyanoborohydride ($NaCNBH_3$). In certain embodiments, the methyl ester is methyl acrylate. In certain embodiments, the alcohol is tert-Butyl alcohol (t-BuOH). In certain embodiments, the radical initiator is AIBN, the reducing agent is sodium $NaCNBH_3$, the methyl ester is methyl acrylate, and the alcohol is t-BuOH.

Alternatively, subjecting the iodo-acetal compound to a cyclization reaction can comprise reacting the iodo-acetal compound and the methyl ester with a metal-based reducing agent, a chelating agent, an alcohol, and a dehydrogenation catalyst. In certain embodiments, the metal-based reducing agent is nickel(II) chloride ethylene glycol dimethyl ether complex ($NiCl_2$·glyme). In certain embodiments, the chelating agent is neocupoine. In certain embodiments, the alcohol is methanol. In certain embodiments, the dehydrogenation catalyst is a zinc oxide nanopowder. In certain embodiments, the methyl ester is methyl acrylate. In certain embodiments, the metal-based reducing agent is $NiCl_2$·glyme, the chelating agent is neocupoine, the alcohol is methanol, the dehydrogenation catalyst is a zinc oxide nanopowder, and the methyl ester is methyl acrylate.

The catalyst of the reacting the cyclization product with a catalyst step is a Grignard reagent and the dialkyldialkoxytitanium reagent is a stoichiometric amount of $CIT^{i}(O_{i}Pr)_3$. The Grignard reagent can be, for example, ethyl magnesium bromide.

In certain embodiments, the method can further comprise quenching hydrolysis when at or about 5-10% of the deprotected cyclopropanol compound remains.

In certain embodiments, the method can further comprise concentrating the hemi-acetal compound with dichloromethane (DCM).

The Wittig reaction or olefination conditions can comprise adding the hemi-acetal compound to a reaction solution comprising methyltriphenylphosphonium bromide ($CH_3PPh_3Br$) and potassium hexamethyldisilazanide (KHMDS) in THF. In certain embodiments, the method further comprises monitoring a reaction solution of the Wittig reaction or olefination using thin-layer chromatography (TLC) and quenching the Wittig reaction or olefination upon detection of a byproduct.

Subjecting the olein compound to a carbonylative spirolactonization reaction can further comprise combining the olefin compound with a solvent, an oxidant, and a palladium catalyst. The solvent can be, for example, anhydrous benzene or anhydrous THF. In certain embodiments, the oxidant is 2,3-Dichloro-5,6-dicyano-1,4-benzoquinone (DDQ). The palladium catalyst can be, for example, palladium(II) acetate ($Pd(OAc)_2$) or palladium(II) trifluoroacetate ($Pd(TFA)_2$). In certain embodiments, the solvent is anhydrous benzene or anhydrous THF, the oxidant is DDQ, and the palladium catalyst is $Pd(OAc)_2$ or $Pd(TFA)_2$.

The Z-selective catalyst can be Ru—Z-Mes or Ru—Z-DIPP. In certain embodiments, the Z-selective catalyst is Ru—Z-Mes. In certain embodiments, the Z-selective catalyst can be Ru—Z-DIPP.

The molecule having a terminal olefin can be, for example, methyl 3-butenoate.

In certain embodiments, a method for synthesis of a tricyclic-prostaglandin $D_2$ metabolite (PGDM) methyl ester or a pharmaceutically acceptable salt thereof can comprise: providing a first compound, for example, having a structure of the following formula:

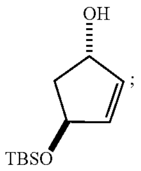 [SMILES: CC(C)(C)[Si](C)(C)O[C@@H]1C=C[C@@H](O)C1]

converting the first compound to the iodo-acetal compound and deprotecting a silyl ether moiety thereof, for example, wherein the iodo-acetal compound has a structure of the following formula:

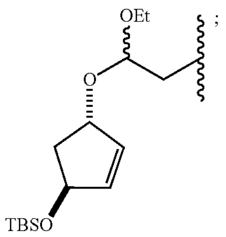 [SMILES: *CC(OCC)O[C@@H]1C=C[C@@H](O[Si](C)(C)C(C)(C)C)C1]

reacting the iodo-acetal compound and the methyl ester with a $NiCl_2$·glyme, neocupoine, methanol, and zinc oxide nanopowder to provide a cyclization product; reacting the cyclization product with ethyl magnesium bromide and a stoichiometric amount of $CIT^{i}(O_{i}Pr)_3$ under conditions sufficient to produce a cyclopropanol compound, followed by deprotecting a silyl ether of the cyclopropanol compound; hydrolyzing the deprotected cyclopropanol compound to form a hemi-acetal compound, for example, having a structure of the following formula:

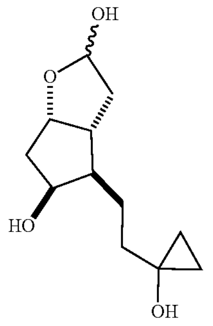

reacting the hemi-acetal compound under suitable Wittig reaction or olefination conditions to provide an olefin compound, wherein the hemi-acetal compound is combined in a reaction solution with $CH_3PPh_3Br$, KHMDS, and THF; subjecting the olefin compound to a carbonylative spirolactonization reaction to produce a compound having an oxaspirolactone moiety, the compound having a structure of the following formula:

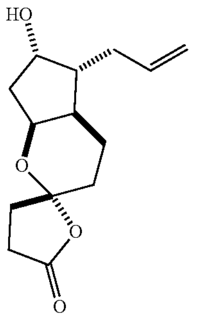
;

reacting a molecule having a terminal olefin with the compound having an oxaspirolactone moiety and Ru—Z-Mes or Ru—Z-DIPP under conditions suitable for a Z-selective cross metathesis reaction to produce tricyclic-PGDM methyl ester or a pharmaceutically acceptable salt thereof. The method can also further comprise quenching hydrolysis when at or about 5-10% of the deprotected cyclopropanol compound remains.

Compounds are also provided herein. In certain embodiments, a tricyclic-PGDM methyl ester or a pharmaceutically acceptable salt thereof is provided, such compound produced by any of the methods described herein.

BRIEF DESCRIPTION OF DRAWINGS

The detailed description will be better understood when taken in conjunction with the accompanying drawings, wherein:

FIG. 6A shows catalysts used in the Z-selective metathesis studies herein.

FIG. 6B shows images of the Z-selective metathesis reaction setup used in embodiments hereof.

FIG. 7 shows the X-ray structure of compound 15 and the related X-ray analysis data.

DETAILED DESCRIPTION

Figure 1:
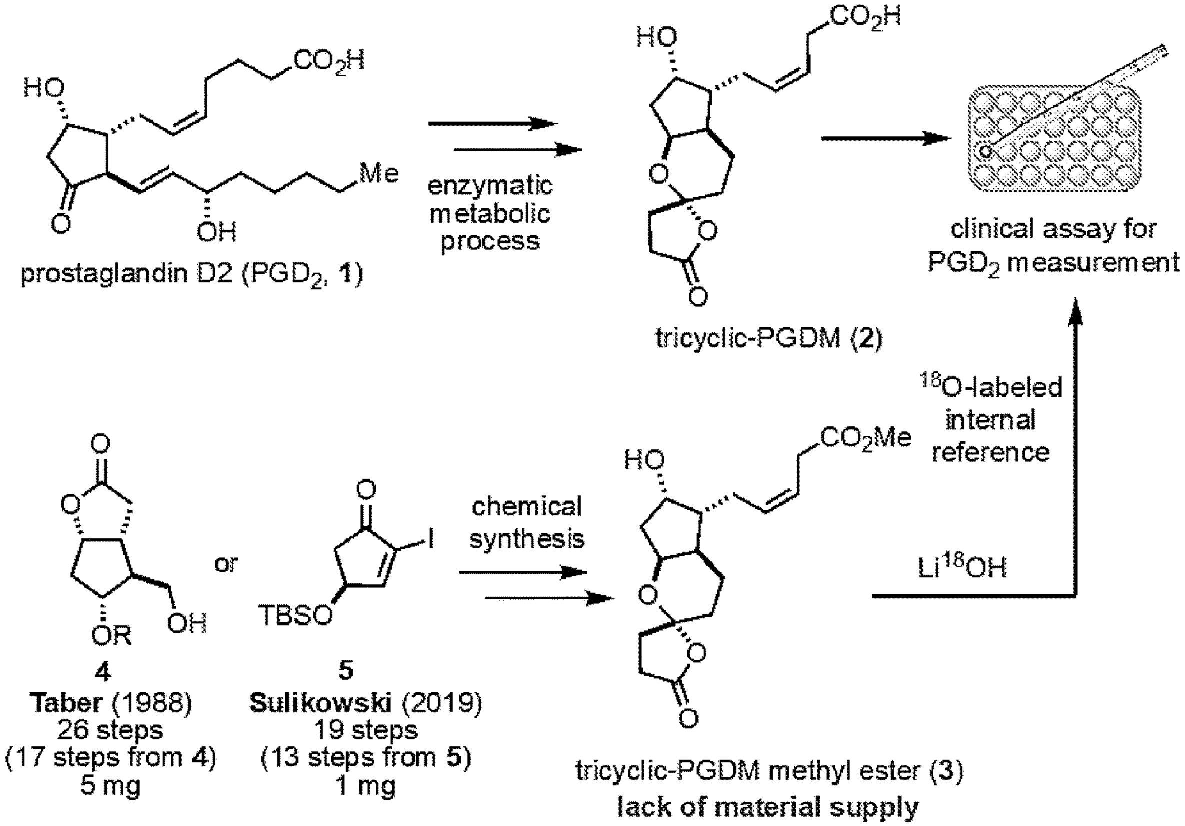
FIG. 1 shows a schematic diagram showing a potential clinical use of tricyclic-$PGD_2$ metabolite (PGDM) methyl ester (compound 3) in a conventional $PGD_2$ assay and the conventional synthesis of tricyclic-PGDM methyl ester.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Methods are provided herein for the efficient synthesis of (±)-tricyclic-prostaglandin $D_2$ metabolite (PGDM) methyl ester. Tricyclic-PGDM methyl ester can have a structure according to the following formula:

Compound 3

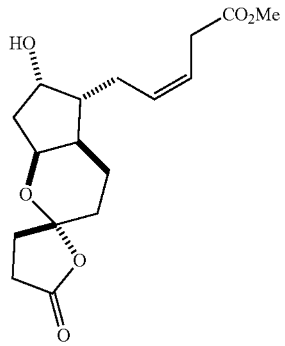

In certain embodiments, such methods can produce up to 75 mg of tricyclic-PGDM methyl ester.

The methods can use three transition metal (e.g., Ni, Pd, and Ru)-catalyzed transformations to build strategic C—C bonds and key ring systems. In certain embodiments, the methods use one or more transition metal-catalyzed transformations to build strategic C—C bonds and key ring systems. In certain embodiments, the methods use a modified Stork radical cascade to build strategic C—C bonds and key ring systems.

Figure 2A:
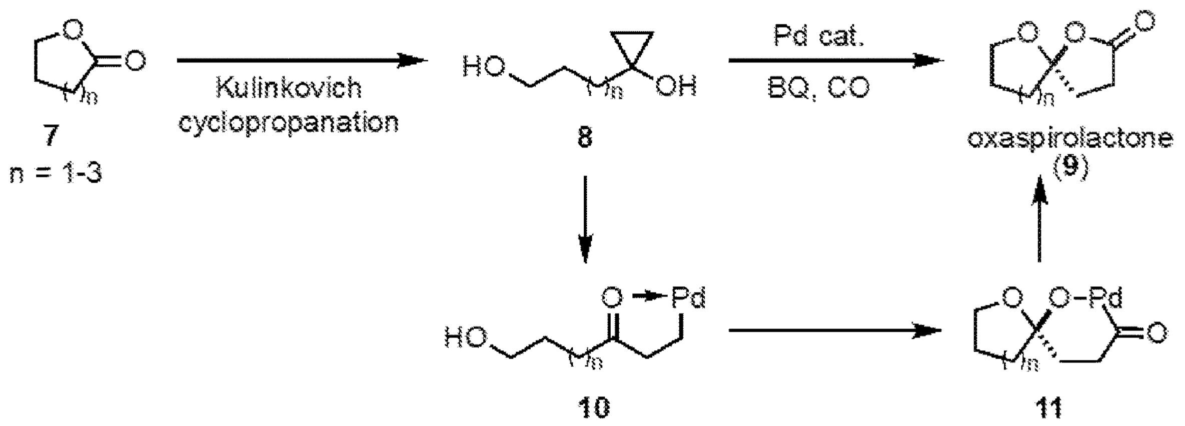
FIG. 2A shows a Pd-catalyzed carbonylative spirolactonization of hydroxycyclopropanols.

The present inventors previously developed a palladium-catalyzed carbonylative spirolactonization to synthesize oxaspirolactones from readily available hydroxycyclopropanols (see 8→9 in FIG. 2A) and have used this method to efficiently synthesize a multitude of complex natural products. See, e.g., Davis et al., Catalytic carbonylative spirolactonization of hydroxycyclopropanols, J. Am. Chem Soc'y 138(33): 10693-10699 (2016); Ma et al., Total syntheses of bisdehydroneostemoninine and bisdeydrostemoninine by catalytic cabonylative spirolactonization, Angewandte Chemie Int'l Ed. 57(46): 15209-15212 (2018); Yin et al., Pyrrole strategy for the γ-lactam-containing stemona alkaloids: (±)stemoamide, (±)tuberostemoamide, and (±)sessilifoliamide A, Organic Letters 22(13): 5001-5004 (2020). To this end, an efficient carbonylative lactonization route to tricyclic-PGDM methyl ester was sought for the purpose of providing a sufficient amount of material to support the clinical assays.

Figure 2B:
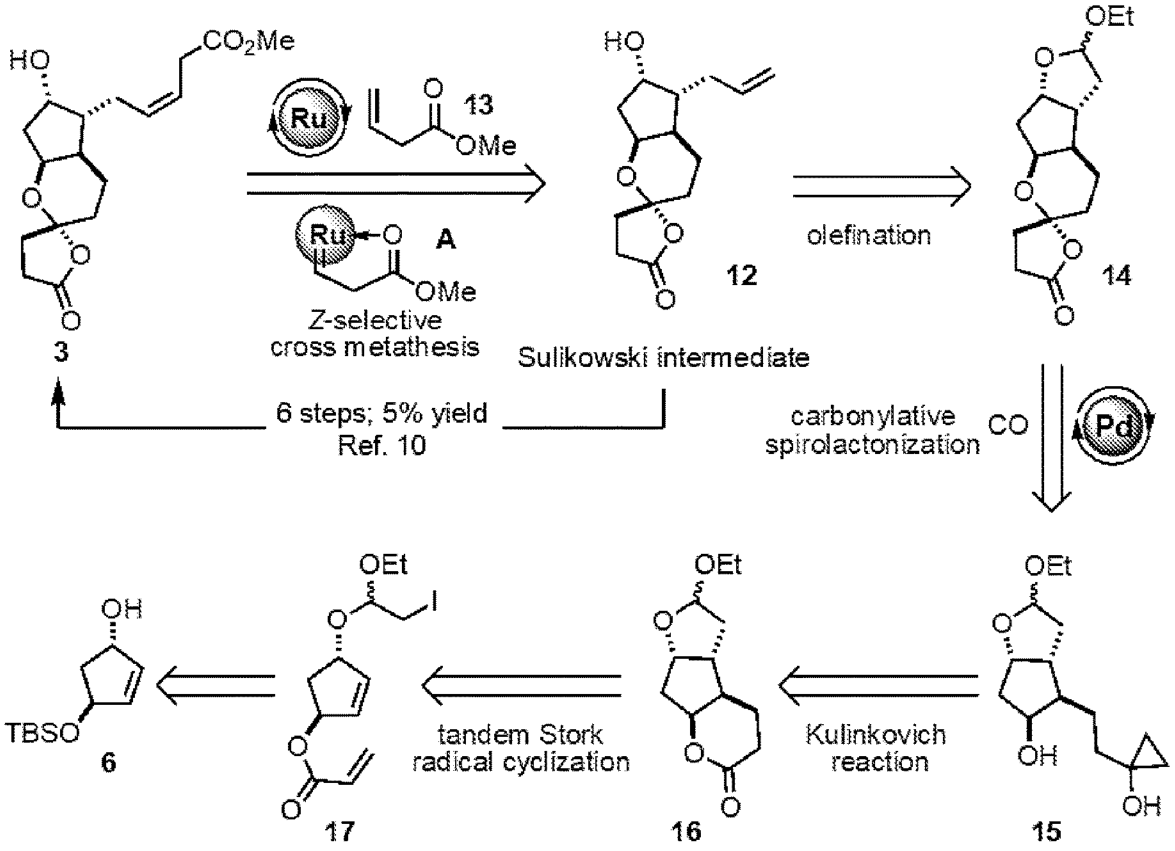
FIG. 2B shows a schematic of an embodiment of retrosynthetic synthesis.

Retrosynthetically, it was reasoned that the (Z)-3-butenoate side chain would need to be incorporated late in the synthesis to ensure its integrity (see FIG. 2B). While the Wittig protocol with an orthoester phosphorane employed by Taber et al. provided 50% yield, the Z:E selectivity was only moderate (4:1) and additional orthoester deprotection and esterification steps were required. Prakash et al., Synthesis of the major urinary metabolite of prostaglandin $D_2$, J. Chemical Soc'y, Perkin Transactions 1 10: 2821 (1988).

Now referring to FIG. 2B, precursor 12 is a known intermediate in the Sulikowski synthesis; however, six more steps (5% overall yield)—including a Lindlar reduction—are required to incorporate the (Z)-3-butenoate side chain. Kimbrough et al. (2019), supra. While a direct Z-selective cross metathesis between precursor 12 and methyl 3-butenoate 13 would be beneficial for installing the side chain, there are several challenges with this approach. In particular, and even despite significant advances in Z-selective cross metathesis, β,γ-unsaturated esters (such as, for example, methyl 3-butenoate 13), remain challenging substrates. Endo & Grubbs, Chelated ruthenium catalysts for Z-selective olefin metathesis, J. Am. Chemical Soc'y 133(22): 8525-8527 (2011); Keitz et al., Improved ruthenium catalysts for Z-selective olefin metathesis, J. Am. Chemical Soc'y 134(1): 693-699 (2012); Rosebrugh et al., Highly active ruthenium metathesis catalysts exhibiting unprecedented activity and Z-selectivity, J. Am. Chemical Soc'y 135(4): 1276-1279 (2013); Meek et al., Catalytic Z-selective olefin cross-metathesis for natural product synthesis, Nature 471: 461-466 (2011); Mann et al., Catalytic Z-selective cross-metathesis with secondary silyl- and benzyl-protected allylic ethers: mechanistic aspects and applications to natural product synthesis, Angewandte Chemie Int'l Ed. 52(32): 8395-8400 (2013); Koh et al., High-value alcohols and higher-oxidative-state compounds by catalytic Z-selective cross-metathesis, Nature 517: 181-186 (2015); Occhipinti et al., Simple and highly Z-selective ruthenium-based olefin metathesis catalyst, J. Am. Chemical Soc'y 135(9): 3331-3334 (2013). Prior to the present disclosure, a method was not available or known for direct Z-selective cross metathesis for (Z)-β,γ-unsaturated esters.

Olefins with a proximal chelating group, such as esters and amides, are particularly challenging substrates. β,γ-unsaturated esters are among the worst substrates because the ester can chelate on the metal center after carbenoid formation (cf. A in FIG. 2B) which forms a stable five-membered metallocycle. Furthermore, the cross-metathesis product tends to undergo double bond isomerization to the E-product or migration to the α,β-unsaturated ester. However, the recent Z-selective cross metathesis results between allylic-substituted olefins or acrylamides and common terminal olefins has been encouraging. Quigley & Grubbs, Ruthenium-catalyzed Z-selective cross metathesis of allylic-substituted olefins, Chemical Science 5(2): 501-506 (2014) and Xu et al., Efficient Z-selective olein-acrylamide cross-metathesis enabled by sterically demanding cyclometalated ruthenium catalysts, J. Am. Chemical Soc'y 142(50): 20987-20993 (2020).

Figure 4:
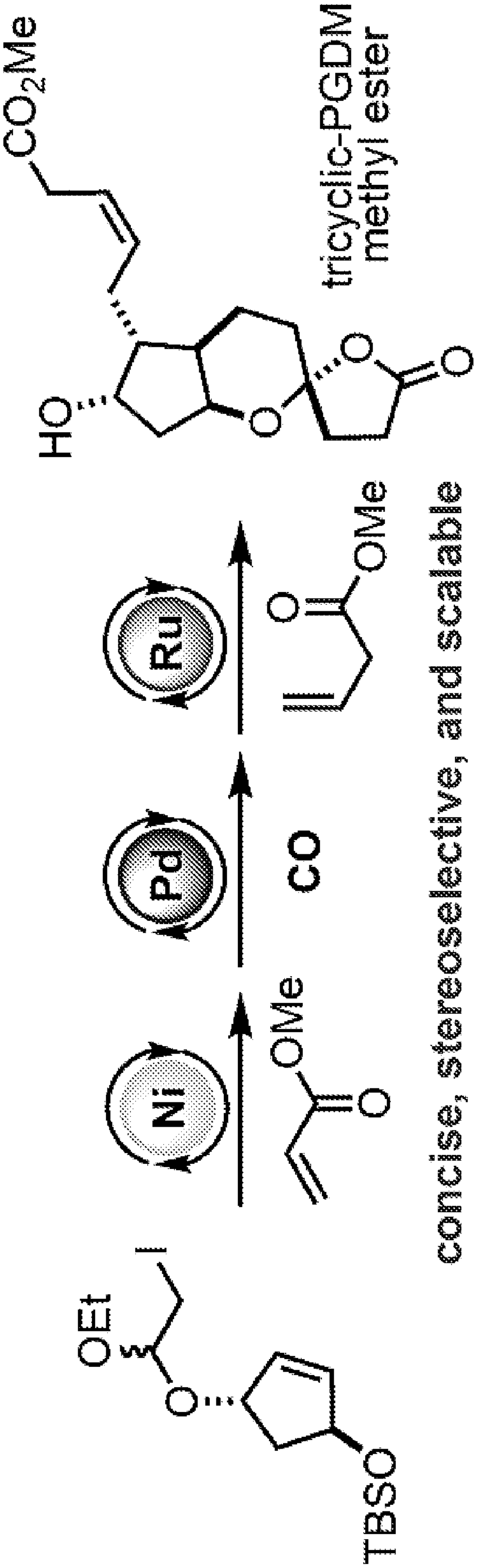
FIG. 4 shows a schematic representation of three-transition metal-catalyzed transformations to form key C—C bonds and ring systems in a method for the total synthesis of tricyclic-PGDM methyl ester (compound 3).

The method hereof allows for a direct Z-selective cross metathesis between precursor 12 and methyl 3-butenoate 13 to complete the synthesis of tricyclic-PGDM methyl ester 3 in one step. This method is highly advantageous as it can result in a generalized method for (Z)-β,γ-unsaturated ester preparation. The method can use starting materials that are readily available and/or straightforward to synthesize. In certain embodiments, the method comprises a nickel-catalyzed Ueno-Stork-type dicarbofunctionalization to form two key C—C bonds and stereocenters, a palladium-catalyzed carbonylative spirolactonization to build an oxaspirolactone moiety, and a Z-selective cross metathesis to form a (Z)-β,γ-unsaturated ester (see FIG. 4), and results in tricyclic-PGDM methyl ester. The method is concise, stereoselective, and scalable.

Starting Materials

The cross-metathesis precursor 12 can be prepared via olefination of the hemi-acetal derived from hydrolysis of acetal 14. Acetal 14 can be prepared from hydroxycyclopropanol 15 using the palladium-catalyzed carbonylative spirolactonization to generate its oxaspirolactone moiety. Hydroxycylopropanol 15 can be generated by the Kulinkovich reaction of lactone 16, which is ex arise from a Ueno-Stork type tandem radical cyclization of iodo-acetal 17. (For a comprehensive review on the Ueno-Stork reaction see Salom-Roig et al., Radical cyclization of haloacetals: the Ueno-Stork reaction, Synthesis 12: 1903-1928 (2004). The radical cyclization precursor 17 can be assembled from the readily available known mono-protected diol 6. Ghosh et al., Enantioselective synthesis of dioxatriquinane structural motifs for HIV-1 protease inhibitors using a cascade radical cyclization, Tetrahedron Letters 56(23), 3314-3317 (2015).

In certain embodiments, the method hereof commences with a multi-decagram preparation of compound 6:

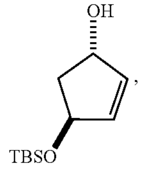

wherein "TBSO" refers to a tert-Butyldimethylsilyl (TBS) ether.

Figure 3:
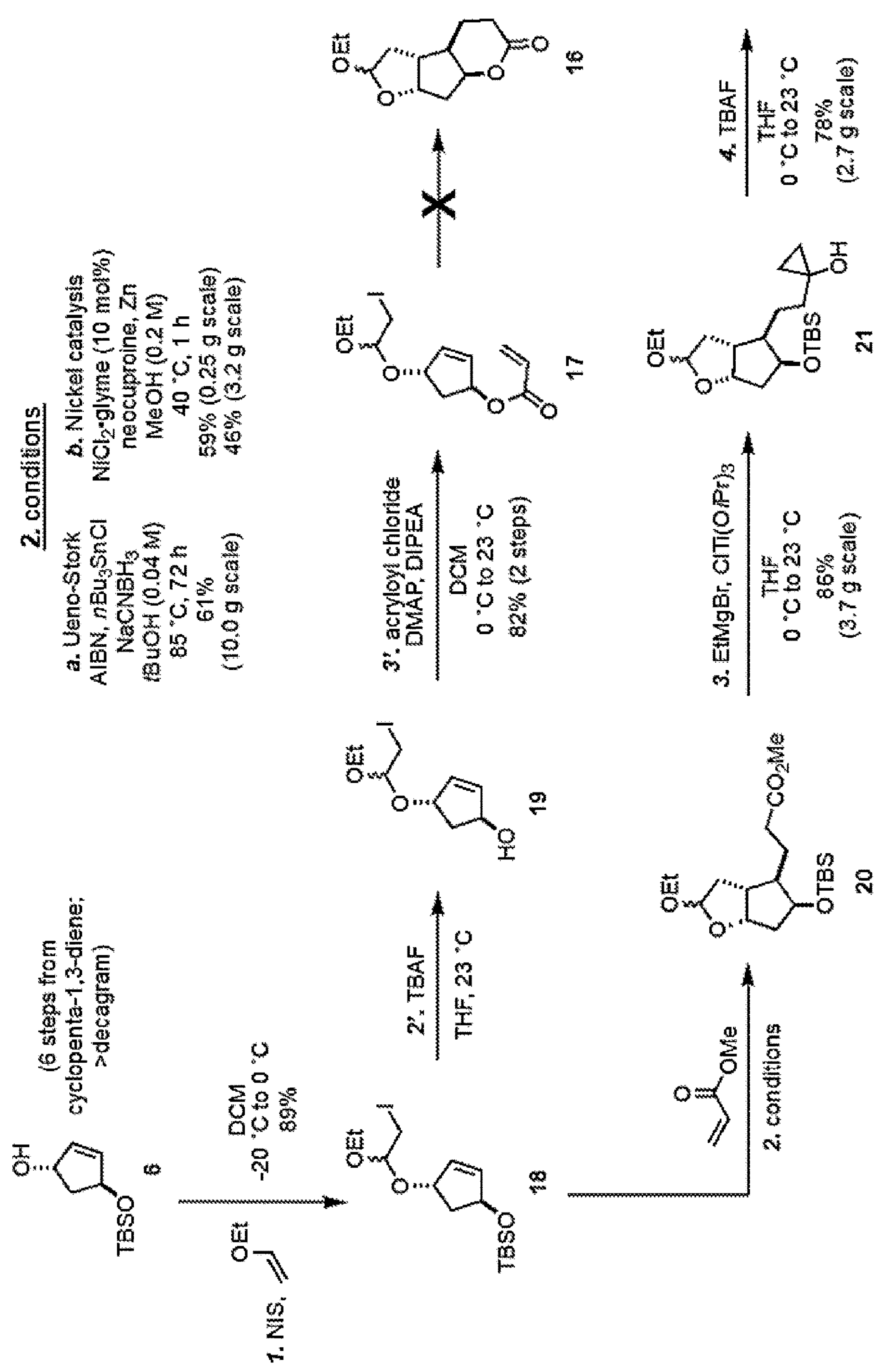
FIG. 3 shows Scheme 1, which represents a method for the total synthesis of tricyclic-PGDM methyl ester (compound 3), where NIS=N-iodosuccinimide, DCM=dichloromethane, TBAF=tetrabutylammonium fluoride, DMAP=4-(dimethylamino)pyridine, DIPEA=N,N-diisopropylethylamine, AIBN=2,2'-azobis(2-methylpropionitrile), THF=tetrahydrofuran, DCE=1,2-dichloroethane, DDQ=2,3-dichloro-5,6-dicyano-p-benzoginone, KHMDS=potassium bis(trimethylsilyl)amide.
Figure 3:
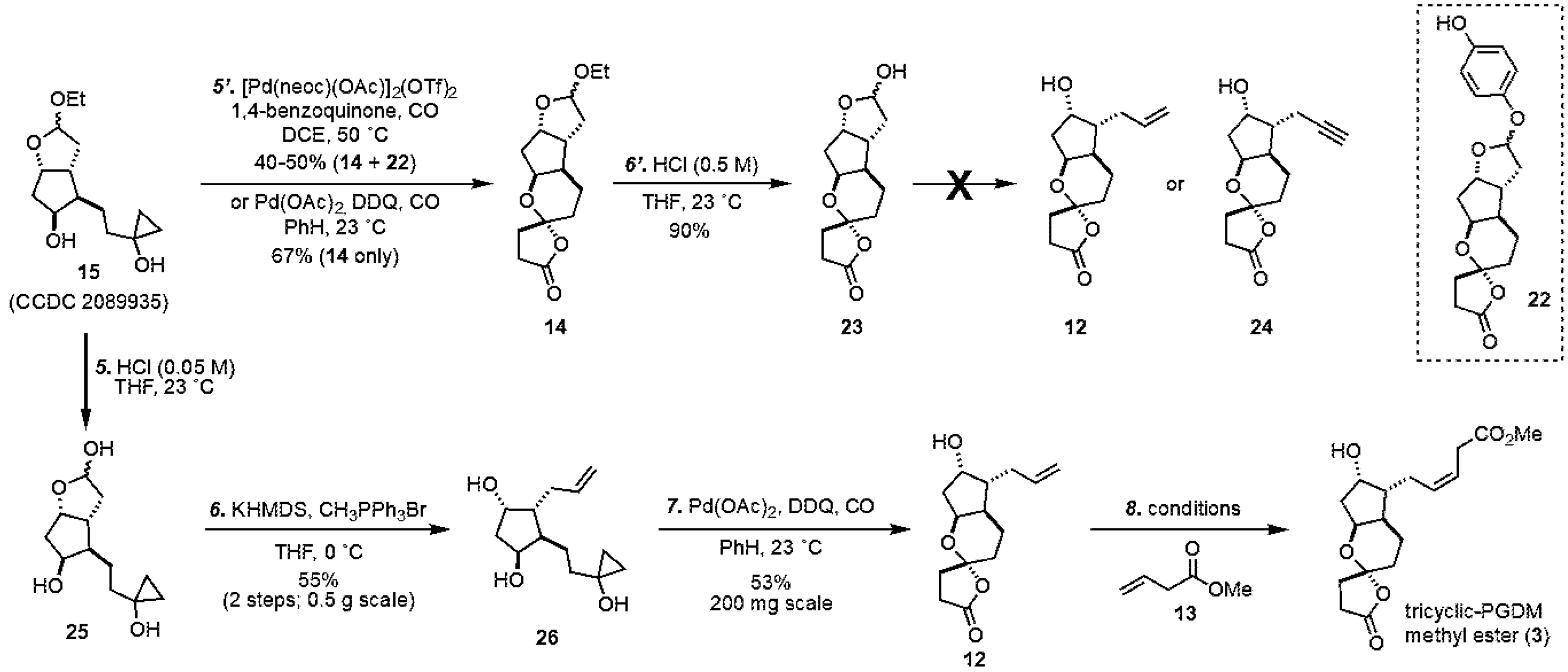

Compound 6 can be prepared, for example, in six steps in racemic form from cyclopentadiene (see Scheme 1 in FIG. 3). Compound 6 can also be synthesized in enantiomerically pure form via procedures with an enzymatic hydrolysis or a Noyori reduction. See, e.g., Deardorff et al., (4S)-(−)-tert-Butyldimethylsiloxy-2-cyclopenten-1-one, Organic Synthesis 73 (1996) and Singh et al., Stereodivergent synthesis of enantioenriched 4-hydroxy-2-cyclopentenones, J. Organic Chemistry 79(1): 452-458 (2014).

In certain embodiments of the method, the method comprises providing compound 6 and converting compound 6 to an iodo-acetal compound (e.g., iodo-acetal 18) and deprotecting a silyl ether moiety of the iodo-acetal compound.

Cyclization Reaction

Because it was presumed the terminal 6-endo-trig cyclization was unfeasible for this substrate, an intermolecular variant utilizing an iodo-acetal compound 18 and methyl acrylate were employed in the Examples described below, however, it will be understood this step is not necessarily limited to such materials.

Accordingly, in certain embodiments, the method comprises subjecting an iodo-acetal compound (e.g., compound 18) to a cyclization reaction with a methyl ester to produce a cyclized product (e.g., cyclization product 20). Such reaction can comprise reacting the iodo-acetal compound and the methyl ester with a radical initiator, a reducing agent, and an alcohol in solution to produce the cyclization product. The methyl ester can be, without limitation, methyl acrylate. In certain embodiments, the radical initiator is 2,2'-azobis(2-methylpropionitrile) (AIBN). In certain embodiments, the reducing agent is sodium cyanoborohydride ($NaCNBH_3$). In certain embodiments, the alcohol is tert-Butyl alcohol (t-BuOH). While efficient and scalable, the organotin toxicity and complications with t-BuOH during the workup led to the exploration of more environmentally benign conditions.

In certain embodiments, the method utilizes an alternative nickel-catalyzed protocol for the cyclization step to obtain dicarbofunctionalization cyclization product (e.g., product 20) (see Example 4 below; 59% yield). Qi & Diao, Nickel-catalyzed dicarbofunctionalization of alkenes, ACS Catalysis 10(15): 8542-8556 (2020). Such protocol is scalable such that it can be utilized on a larger scale (noting that while yield slightly decreased on larger scale (yield about 46%), the procedure was operationally convenient).

The iodo-acetal compound can be subjected to a cyclization reaction comprising reacting the iodo-acetal compound and the methyl ester with a metal-based (e.g., nickel-based) reducing agent, a chelating agent, an alcohol, and a dehydrogenation catalyst. The metal-based reducing agent can be, for example, nickel(II) chloride ethylene glycol dimethyl ether complex ($NiCl_2$·glyme). In certain embodiments, the chelating agent is neocupoine. In certain embodiments, the alcohol is methanol. In certain embodiments, the dehydrogenation catalyst is a zinc oxide nanopowder.

Kulinkovich Cyclopropanation

Thereafter, a Kulinkovich reaction can be performed, followed by TBS-ether deprotection to provide cyclopropanol 15 (see Example 6 below). Referring to the Kulinkovich step, a cyclopropanol product (e.g., compound 21) can be obtained from the cyclization product (e.g., compound 20) via modified Kulinkovich cyclopropanation. A dialkyldialkoxytitanium reagent, such as $ClTi(O^iPr)_3$ (chlorotitaniumtriisopropoxide) or $TiCl_4$ (titanium tetrachloride/tetra n-butyl titanate), can be used to facilitate the cyclopropanation. In certain embodiments, the dialkyldialkoxytitanium reagent is $ClTi(O^iPr)_3$. In certain embodiments, the dialkyldialkoxytitanium reagent is a stoichiometric amount of $ClTi(O^iPr)_3$. In certain embodiments, the dialkyldialkoxytitanium reagent is $TiCl_4$.

The dialkyldialkoxytitanium reagent can be caused to react with a catalyst, for example, under conditions an oi reaction can be maintained. The catalyst can be a Grignard reagent such as, for example, ethyl magnesium bromide (EtMgBr), methyl magnesium bromide, methyl magnesium chloride, and the like, or any catalyst used in preparing the Grignard reagent. In certain embodiments, the Gringard reagent is selected from the group consisting of: EtMgBR, methyl magnesium bromide, methyl magnesium chloride, and any other Grignard reagent known in the art. The Grignard reagent can provide a zinc, magnesium, or sodium to the reaction.

In certain embodiments, the dialkyldialkoxytitanium reagent is $ClTi(O^iPr)_3$ and the catalyst is EtMgBr.

The resulting reaction solution can be filtered (e.g., through a celite pad), washed, isolated (e.g., via distillation, column chromatography, etc.), concentrated, and/or further processed to collect an organic phase using commonly known techniques. The organic phase can be dried (e.g., over magnesium sulfate), filtered, isolated, concentrated, and purified using commonly known techniques, but it will be recognized that all such steps are not necessary.

The cyclopropanol product (e.g., compound 21) can then be subjected to deprotection conditions to deprotect a silyl ether moiety of the cyclopropanol product and provide deprotected cyclopropanol (e.g., compound 15).

Hydrolysis

The deprotected cyclopropanol compound can be hydrolyzed to form a hemi-acetal compound. In certain embodiments, the deprotected cyclopropanol compound is hydrolyzed to form a hemi-acetal compound having the structure:

(compound 25)

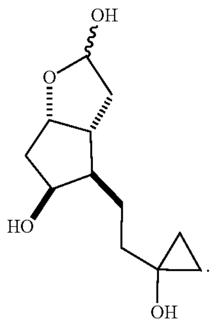

Hydrolysis protocols are commonly known in the art. In certain embodiments, hydrolysis of the deprotected cyclopropanol compound can comprise combining the deprotected cyclopropanol compound with a solvent and aqueous hydrochloride (HCl) (0.05M), for example. In certain embodiments, the solvent is THF or another appropriate solvent. In certain embodiments, the solvent is freshly distilled THF. In certain embodiments, the THF can be THF processed with a solvent purification system (SPS) such as, for example the MBraun Solvent Purification System (M. Braun Inertgas-systeme Gmbh, Garching, Germany).

The method can further comprise quenching hydrolysis (e.g., by adding $K_2CO_3$ to the reaction solution) at a desired point. It can be beneficial to closely monitor the hydrolysis and quench the reaction just when the starting material spot becomes faint. For example, if the reaction is left too long, the product can rapidly degrade; as such, close monitoring can result in higher yields. Additionally, reaction times can vary (e.g., smaller scale reactions can have shorter reaction times).

Detection of the amount of starting material (e.g., deprotected cyclopropanol compound) in the reaction solution can be performed using any appropriate modalities now known or hereinafter developed. In certain embodiments, nuclear magnetic resonance (NMR) spectroscopy is used to detect the amount of starting material in the reaction solution. In certain embodiments, hydrolysis is quenched when at or about 5-10% (e.g., 5-10%) of the deprotected cyclopropanol compound/starting material remains in the reaction solution.

The hemi-acetal compound (e.g., compound 25) can be concentrated one or more times prior to undergoing a Wittig reaction or olefination, if desired, using known methods. For example, in certain embodiments, the method can further comprise concentrating the hemi-acetal compound 25 with DCM. This concentrating step can be performed once or repeated sequentially as desired.

Wittig Reaction or Olefination

The method further comprises a Wittig reaction or olefination step prior to carbonylative spirolactonization. In certain embodiments, such step comprises reacting the hemi-acetal compound under suitable Wittig reaction or olefination conditions to provide an olefin compound. In certain embodiments, the olefin compound has the structure:

(compound 26)

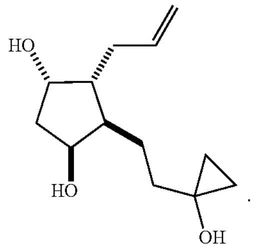

The Wittig reaction or olefination step can comprise treating the hemi-acetal compound under suitable Wittig reaction or olefination conditions to provide an olefin compound (e.g., compound 26). In certain embodiments, the Wittig reaction or olefination conditions comprise adding the hemi-acetal compound to a reaction solution comprising a Wittig salt with and a strong dissociating base in a solvent (e.g., anhydrous THF or anhydrous benzene (PhH)).

The starting material for this step, as previously stated, can be hemi-acetal compound 25. The hemi-acetal compound can be purified prior to this step using known techniques or provided as crude.

The Wittig salt can be any salt suitable to facilitate a Wittig or olefination reaction. In certain embodiments, the Wittig salt is selected from a group consisting of methyltriphenylphosphonium bromide ($CH_3PPh_3Br$), methyltriphenylphosphonium iodide, and 5-hydroxyltriphenylphosphonium bromide. In certain embodiments, the Wittig salt is methyltriphenylphosphonium bromide.

Any strong dissociating bases known in the art can be used, provided the appropriate reaction conditions are achieved. In certain embodiments, the base is n-butyllithium (n-BuLi), sodium amide ($NaNH_2$), or such as potassium hexamethyldisilazanide (KHMDS). In certain embodiments, the base is KHMDS.

The quality of the dissociating base can impact the rate of reaction. The reaction solution can be monitored to quench the Wittig reaction or olefination when desired. In certain embodiments, the reaction solution of the Witting reaction or olefination is quenched upon detection of a byproduct (e.g., pure EtOAc).

Reaction monitoring can be performed by various modalities known in the art. In certain embodiments, the reaction is monitored by thin-layer chromatography (TLC). In certain embodiments, the reaction is monitored in about 5-minute intervals.

Carbonylative Spirolactonization Reaction

The resulting olefin compound is then subjected to a carbonylative spirolactonization reaction to produce a compound having an oxaspirolactone moiety. In certain embodiments, the compound having an oxaspirolactone moiety has the structure:

(compound 12)

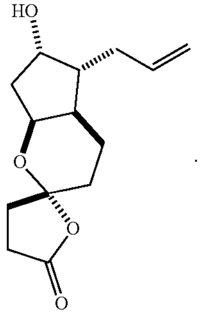

The carbonylative spirolactonization reaction can comprise a palladium-catalyzed ring opening carbonylative lactonization as described in Cai et al., *Catalytic Hydroxycyclopropanol Ring-Opening Carbonylative Lactonization to Fused Bicyclic Lactones*, J. Am. Chemical Soc'y 142(32): 13677-13682 (2020) for synthesizing bicyclic lactones. For example, the carbonylative spirolactonization reaction can comprise a palladium-catalyzed ring opening carbonylative lactonization.

In certain embodiments, the carbonylative spirolactonization reaction comprises combining the olefin compound with a solvent, an oxidant, and a palladium catalyst. The solvent can be any appropriate solvent. In certain embodiments, the solvent is anhydrous benzene (PhH). In certain embodiments, the solvent is anhydrous THF.

The oxidant can be 2,3-Dichloro-5,6-dicyano-1,4-benzoquinone (DDQ).

The palladium catalyst can be any palladium catalyst known in the art that can catalyze the reaction. The catalyst can be, for example, a palladium acetate derivative. In certain embodiments, the catalyst is palladium(II) acetate ($Pd(OAc)_2$). In certain embodiments, the catalyst is palladium(II) trifluoroacetate ($Pd(TFA)_2$).

Z-Selective Cross Metathesis Reaction

The compound having an oxaspirolactone moiety (e.g., compound 12) can then be reacted with a molecule comprising at least one terminal olefin under conditions suitable for a Z-selective cross metathesis reaction to produce tricyclic-PGDM methyl ester (having an internal double bond) or a pharmaceutically acceptable salt thereof. The metathesis reaction can proceed with high selectivity and/or high conversion. In certain embodiments, the method can provide the ability to selectively synthesize, via the metathesis reaction, products having a high percentage of Z-configuration about their double bond. Those with ordinary skill in the art will understanding the meaning of the terms "cis" or "Z" and "trans" or "E" as used within the context of the present disclosure.

The internal double bond of the tricyclic-PGDM methyl ester product can be produced in a high Z:E ratio in favor of the Z-isomer. A "terminal double bond" in the context of a metathesis reaction refers to a double bond between a first and a second carbon atom (e.g., C=C), wherein the two substituents on the first carbon atom are both hydrogen and at least one substituent on the second carbon atom is not hydrogen (e.g., $H_2C{=}CR^aH$). An "internal double bond" in the context of a metathesis reaction refers to a double bond between a first and a second carbon atom (e.g., C═C), wherein at least one substituent on each of the first and second carbon atoms are not hydrogen (e.g., $R^aR^bC{=}CR^cR^d$, wherein at least one of $R^a$ and $R^b$ are not hydrogen and at least one of $R^c$ and $R^d$ are not hydrogen).

In some embodiments, the internal double bond of the tricyclic-PGDM methyl ester product of the metathesis reaction can be formed with high selectivity for the Z-isomer. For example, the internal double bond of the product can be formed in a Z:E (i.e., cis:trans) ratio of about 1:2, about 1:1, about 2:1, about 3:1, about 4:1, about 5:1, about 10:1, about 25:1, about 50:1, about 100:1, or greater. In some embodiments, the double bond can be produced in a Z:E ratio greater than about 1:1, greater than about 2:1, greater than about 3:1, greater than about 4:1, greater than about 5:1, greater than about 10:1, greater than about 20:1, greater than about 30:1, greater than about 40:1, greater than about 50:1, greater than about 75:1, greater than about 100:1, or greater, in favor of the Z-isomer. In some cases, the Z- or E-selectivity can be expressed as a percentage of products formed. In some cases, the product can be greater than about 50% Z-isomer, greater than about 60% Z-isomer, greater than about 70% Z-isomer, greater than about 80% Z-isomer, greater than about 90% Z-isomer, greater than about 95% Z-isomer, greater than about 98% Z-isomer, greater than about 99% Z-isomer, or, in some cases, greater than about 99.5%. In some instances, the product may be between about 50% and about 99% Z-isomer, between about 50% and about 90% Z-isomer, between about 60% and about 99% Z-isomer, between about 60% and about 95% Z-isomer, between about 70% and about 98% Z-isomer, between about 80% and about 98% Z-isomer, between about 90% and about 99% Z-isomer, or the like.

In some cases, the metathesis reaction can proceed with high conversion. Conversion refers to the percent of the limiting reagent converted to product. In some embodiments, percent conversion can be calculated according to the following equation: % Conversion=100−{(final moles of limiting reagent)×100 (initial moles of limiting reagent)}, where the initial moles of the limiting reagent can be calculated from the amount of limiting reagent added to reaction vessel and the final moles of the limiting reagent can be determined using techniques known to those of ordinary skill in the art (e.g., isolation of reagent, GPC, HPLC, NMR, etc.). In some cases, the metathesis reaction can proceed with a conversion of at least about 30%, at least about 40%, at least about 50%, at least about 60%, at least about 70%, at least about 75%, at least about 80%, at least about 85%, at least about 90%, at least about 95%, at least about 97%, at least about 98%, at least about 99%, or more. In some cases, the conversion is about 70%, about 75%, about 80%, about 85%, about 90%, about 95%, about 97%, about 98%, about 99%, or the like. In some instances, the conversion is between about 60% and about 99%, between about 70% and about 95%, between about 70% and about 90%, or any other range therein.

In certain embodiments, the metathesis reaction can proceed with good turnover numbers. The term "turnover number," refers to the number of average times a catalyst is able to promote a reaction. In some embodiments, the turnover number can be calculated according to the following equation:

Turnover number=% yield 100×{(moles of limiting reagent) (moles of catalyst)}, wherein the percent yield may be calculated according to the following equation:

% Yield=100×{(moles of a desired product)(moles of limiting reagent)}.

For example, in a metathesis reaction, the moles of catalyst can be determined from the weight of catalyst (or catalyst precursor) provided, the related moles of limiting reagent (e.g., generally one half the moles of terminal olefin starting material as two moles of starting material are reacted to form one mole of product) can be determined from the amount of limiting reagent added to the reaction vessel, and the moles of a desired product (e.g., the Z-isomer of the product) can be determined using techniques known to those of ordinary skill in the art (e.g., isolation of product, GPC, HPLC, NMR, etc.).

In some cases, the metathesis reaction can proceed at a turnover number of at least about 10, at least about 25, at least about 50, at least about 100, at least about 200, at least about 300, at least about 400, at least about 500, at least about 1000, at least about 3,000, at least about 5,000, or more. In some cases, the turnover number is between about 10, and about 1000, between about 50 and about 500, between about 50 and 200, or any other range therein. In certain embodiments, the turnover number is about 10, about 20, about 30, about 50, about 75, about 100, about 200, about 500, about 1000, about 5000, or the like. The turnover frequency is the turnover number divided by the length of reaction time (e.g., seconds).

A metathesis reaction can be carried out using techniques known to those of ordinary skill in the art. In some cases, the reaction involves exposing a catalyst (e.g., Ru—Z-Mes, Ru—Z-DIPP, or any other otherwise known) to a plurality of molecules comprising a terminal olefin (e.g., compound 12 and a terminal alkene). In some instances, the reaction mixture can be agitated (e.g., stirred, shaken, etc.). The reaction products can be isolated (e.g., via distillation, column chromatography, etc.) and/or analyzed (e.g., gas liquid chromatography, high performance liquid chromatography, nuclear magnetic resonance spectroscopy, etc.) using commonly known techniques.

Molecules comprising at least one terminal olefin will be known to those of ordinary skill in the art. In certain embodiments, a molecule comprising at least one terminal olefin can comprise one or more ethylenic units and/or heteroatoms (e.g., oxygen, nitrogen, silicon, sulfur, phosphorus, etc.).

In some cases, the molecule comprising at least one terminal olefin has the formula:

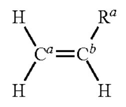

wherein $R^a$ is alkyl, alkenyl, heteroalkyl, heteroalkenyl, aryl, heteroaryl, or acyl, optionally substituted. The internal double bond of the product can comprise one $C^bHR^a$ from the terminal alkene (e.g., to form the Z- or E-isomer of $R^aHC^b{=}C^bHR^a$). In certain embodiments, the molecule comprising at least one terminal olefin is methyl 3-butenoate (e.g., compound 13).

Other non-limiting examples of molecules comprising terminal olefins are substituted and unsubstituted linear alkyl internal olefins such as $C_4$-$C_{30}$ olefins (e.g., 1-butene, 1-pentene, 1-hexene, 1-heptene, 1-octene, 1-decene, 1-dodecene, 1-tetradecene, 1-hexadecene, 1-octadecene, 1-eicosene, allylbenzene, allyltrimethylsilane, methyl-10-undecenoate, allylboronic acid pincol ester, allylbenzylether, N-allyl-4-methylbenzenesulfonamide, allylaniline, methyl-9-decenoate, allyloxy(tert-butyl)dimethyl silane, allylcyclohexane, etc.).

In sum, the method hereof can achieve a concise synthesis of tricyclic-PGDM methyl ester (3) in 8 steps from readily available known starting material (e.g., compound 6). Such methods comprise a Z-selective cross metathesis to form the challenging (Z)-β,γ-unsaturated ester, a palladium-catalyzed carbonylative spirolactonization to build the oxaspirolactone moiety, and a nickel-catalyzed Ueno-Stork-type dicarbofunctionilzation to form two key C—C bonds and stereocenters. A general cross-metathesis protocol for (Z)-β,γ-unsaturated esters was established (see FIG. 4). The methods hereof have accumulated over 75 mg of pure tricyclic-PGDM methyl ester. As described above, this material is useful at least for the tricyclic-PGDM assay and the efficient production thereof can further its availability as a clinical tool.

A tricyclic-PGDM methyl ester or pharmaceutically acceptable salt thereof is also provided. In certain embodiments, such a tricyclic-PGDM methyl ester is produced according to any of the methods described.

All patents, patent application publications, journal articles, textbooks, and other publications mentioned in this specification are indicative of the level of skill of those in the art to which the disclosure pertains. All such publications are incorporated herein by reference to the same extent as if each individual publication were specifically and individually indicated to be incorporated by reference.

While certain embodiments of the present disclosure have been shown and described herein, it will be apparent to those skilled in the art that such embodiments are provided by way of example only. It is not intended that the claimed invention be limited by the specific examples provided within the specification.

While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein, which depend upon a variety of conditions and variables. It should be understood that various alternatives to the embodiments of the invention described herein may be employed in practicing the invention. It is, therefore, contemplated that the invention shall also cover any such alternatives, modifications, variations or equivalents. It is intended that the following claims define the scope of the invention and that methods and structures within the scope of these claims and their equivalents be covered thereby.

Those skilled in the art will recognize that numerous modifications can be made to the specific implementations described above. The implementations should not be limited to the particular limitations described. Other implementations may be possible.

Certain Additional Definitions

As used herein and in the appended claims, the singular forms “a,” “and,” and “the” include plural referents unless the context clearly dictates otherwise. Thus, for example, reference to “a compound” includes a plurality of such compounds. When ranges are used herein for physical properties, such as molecular weight, or chemical properties, such as chemical formulae, all combinations and sub-combinations of ranges and specific embodiments therein are intended to be included. The term “about,” when referring to a number or a numerical range, means that the number or numerical range referred to is an approximation within experimental variability (or within statistical experimental error), and thus the number or numerical range may vary between 1% and 15% of the stated number or numerical range. The term “comprising” (and related terms such as “comprise” or “comprises” or “having” or “including”) is not intended to exclude in certain embodiments of any compound, composition, method, process, or the like that may “consist of” or “consist essentially of” the described features.

“Alkyl” refers to a straight or branched or cyclic hydrocarbon chain radical consisting solely of carbon and hydrogen atoms, containing no unsaturation, and having from one to fifteen carbon atoms (e.g., $C_1$-$C_{15}$ alkyl). In various embodiments, an alkyl comprises three to six carbon atoms (e.g., $C_3$-$C_6$ alkyl), one to thirteen carbon atoms (e.g., $C_1$-$C_{13}$ alkyl), one to eight carbon atoms (e.g., $C_1$-$C_8$ alkyl), one to five carbon atoms (e.g., $C_1$-$C_5$ alkyl), one to four carbon atoms (e.g., $C_1$-$C_4$ alkyl), one to three carbon atoms (e.g., $C_1$-$C_3$ alkyl), one to two carbon atoms (e.g., $C_1$-$C_2$ alkyl), one carbon atom (e.g., $C_1$ alkyl), five to fifteen carbon atoms (e.g., $C_5$-$C_{15}$ alkyl), five to eight carbon atoms (e.g., $C_5$-$C_8$ alkyl), two to five carbon atoms (e.g., $C_2$-$C_5$ alkyl), or three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, $—OR^a$, $—SR^a$, $—OC(O)—R^a$, $—N(R^a)_2$, $—C(O)R^a$, $—C(O)OR^a$, $—C(O)N(R^a)_2$, $—N(R^a)C(O)OR^a$, $—OC(O)—N(R^a)_2$, $—N(R^a)C(O)R^a$, $—N(R^a)S(O)_tR^a$ (where t is 1 or 2), $—S(O)_tOR^a$ (where t is 1 or 2), $—S(O)_tR^a$ (where t is 1 or 2) and $—S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

“Alkenyl” refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Cyano" refers to the group —CN.

"Oxo" refers to the group ═O.

The term "substituted" means a functional group in which one or more hydrogen atoms contained therein are replaced by one or more non-hydrogen atoms. The term "functional group" or "substituent" means a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

Non-limiting examples of substituents that can be bonded to a substituted carbon atom (or other functional groups such as nitrogen) can include, without limitation, F, Cl, Br, I, OR, $OC(O)N(R)_2$, CN, NO, $NO_2$, $ONO_2$, azido, $CF_3$, $OCF_3$, R, O (oxo), S (thiono), C(O), S(O), methylenedioxy, ethylenedioxy, $N(R)_2$, SR, SOR, $SO_2R$, $SO_2N(R)_2$, $SO_3R$, $(CH_2)_{0-2}P(O)OR_2$, C(O)R, C(O)C(O)R, $C(O)CH_2C(O)R$, C(S)R, C(O)OR, OC(O)R, $C(O)N(R)_2$, $OC(O)N(R)_2$, $C(S)N(R)_2$, $(CH_2)_{0-2}N(R)C(O)R$, $(CH_2)_{0-2}N(R)C(O)OR$, $(CH_2)_{0-2}N(R)N(R)_2$, N(R)N(R)C(O)R, N(R)N(R)C(O)OR, $N(R)N(R)CON(R)_2$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, $C(═NH)N(R)_2$, C(O)N(OR)R, or C(═NOR)R, wherein R can be hydrogen or a carbon-based moiety, and wherein the carbon-based moiety can itself be further substituted; for example, wherein R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R can be independently mono- or multi-substituted; or wherein two R groups bonded to a nitrogen atom or to adjacent nitrogen atoms can together with the nitrogen atom or atoms form a heterocyclyl, which can be mono- or independently multi-substituted.

The terms "halo," "halogen," or "halide" group, as used herein, by themselves or as part of another substituent, mean, unless otherwise stated, a fluorine, chlorine, bromine, or iodine atom.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized $(4_n+2)$ π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless specifically stated otherwise, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $—R^b—OR^a$, $—R^b—OC(O)—R^a$, $—R^b—OC(O)—OR^a$, $—R^b—OC(O)—N(R^a)^2$, $—R^b—N(R^a)^2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)_tR^a$ (where t is 1 or 2), $—R^b—S(O)_tR^a$ (where t is 1 or 2), $—R^b—S(O)_tOR^a$ (where t is 1 or 2) and $—R^b—S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

The term "aryl" means a substituted or unsubstituted cyclic aromatic hydrocarbon that does not contain heteroatoms in the ring. Accordingly, aryl groups can include, without limitation, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

A heteroaryl ring is an embodiment of a heterocyclyl group. The phrase "heterocyclyl group" includes fused ring species including those that comprise fused aromatic and non-aromatic groups. Representative heterocyclyl groups include, but are not limited to, pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "methoxy" or "methoxy functional group" refers to an alkoxy group ($OCH_3$) and can be abbreviated as "—OMe".

The term "olefin" refers to any species having at least one ethylenic double bond such as normal and branched chain aliphatic olefins, cycloaliphatic olefins, aryl substituted olefins and the like. Olefins can comprise terminal double bond(s) ("terminal olefin") and/or internal double bond(s) ("internal olefin") and can be cyclic or acyclic, linear or branched, optionally substituted. The total number of carbon atoms can be from 1 to 100, or from 1 to 40; the double bonds of a terminal olefin may be mono- or bi-substituted and the double bond of an internal olefin may be bi-, tri-, or tetrasubstituted. In some cases, an internal olefin is bi-substituted.

The phrase "pharmaceutically acceptable salt" refers to pharmaceutically acceptable organic or inorganic salts of a compound of the referenced formula. For use in medicine, the salts of a compound of a formula can be pharmaceutically acceptable salts. Other salts can, however, be useful in the preparation of a compound of an identified formula or of their pharmaceutically acceptable salts. A pharmaceutically acceptable salt can involve the inclusion of another molecule such as an acetate ion, a succinate ion or other counter ion. The counter ion can be any organic or inorganic moiety that stabilizes the charge on the parent compound. Furthermore, a pharmaceutically acceptable salt can have more than one charged atom in its structure.

Pharmaceutically acceptable salts of the compounds of a formula described herein can include those derived from suitable inorganic or organic acids or bases. In some embodiments, the salts can be prepared in situ during the final isolation and purification of the compounds. In other embodiments the salts can be prepared from the free form of the compound in a separate synthetic step.

Salts derived from inorganic bases include, for example and without limitation, aluminum, ammonium, calcium, copper, ferric, ferrous, lithium, magnesium, manganic salts, manganous, potassium, sodium, and zinc. Particular embodiments include ammonium, calcium, magnesium, potassium and sodium salts. Salts derived from pharmaceutically acceptable organic non-toxic bases can include salts of primary, secondary and tertiary amines, substituted amines including naturally occurring substituted amines, cyclic amines and basic ion exchange resins, such as arginine, betaine, caffeine, choline, N, $N_1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, and tromethamine.

Salts can be prepared from pharmaceutically acceptable non-toxic acids, including inorganic and organic acids. Such acids include, without limitation, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acid. In certain embodiments, the salt can include citric, hydrobromic, hydrochloric, maleic, phosphoric, sulfuric and tartaric acids. Other exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and/or pamoate salts.

The term "protective group" refers to a moiety of a compound that masks or alters the properties of a functional group or the properties of the compound as a whole. The chemical substructure of a protective group can vary widely. One function of a protective group is to serve as an intermediate in the synthesis of a parental compound. Chemical protective groups and strategies for protection/deprotection are well known in the art. See: "Protective Groups in Organic Chemistry", Theodora W. Greene (John Wiley & Sons, Inc., New York, 1991. Protective groups are often utilized to mask the reactivity of certain functional groups, to assist in the efficiency of desired chemical reactions, e.g., making and breaking chemical bonds in an ordered and planned fashion. Protection of functional groups of a compound can alter other physical properties besides the reactivity of the protected functional group, such as the polarity, lipophilicity (hydrophobicity), and other properties that can be measured by common analytical tools. Chemically protected intermediates can themselves be biologically active or inactive. The non-limiting examples of protective groups for an amine include t-butyloxycarbonyl (Boc), benzyloxycarbonyl (Cbz), 9-fluorenylmethoxycarbonyl (Fmoc), and the like.

The term "deprotection conditions" refers to the reaction conditions under which a protective group is removed.

The term "silyloxy" represents $—OSi(R^{22})_3$, wherein each $R^{22}$ can be the same or different and can be alkyl, aryl, heteroalkyl, or heteroaryl, optionally substituted. Non-limiting examples of silyloxy groups include $—OSiPh_3$, $—OSiMe_3$, and $—OSiPh_2Me$.

As used herein, the term "substituted" is contemplated to include all permissible substituents of organic compounds, "permissible" being in the context of the chemical rules of valence known to those of ordinary skill in the art. In some cases, "substituted" may generally refer to replacement of a hydrogen atom with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" group must still comprise the phenyl moiety and cannot be modified by substitution, in this definition, to become, e.g., a cyclohexyl group. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For example, a substituted alkyl group may be $CF_3$. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans). Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

Specific exemplary methods hereof are described in additional detail below. The following examples are intended to illustrate certain embodiments of the present invention, but do not exemplify the full scope of the invention.

EXAMPLES

General Methods

Nuclear magnetic resonance spectroscopy (NMR) spectra were recorded on Bruker spectrometers ($^1H$ at 500 MHz, and $^{13}C$ at 125 MHz MHz). Chemical shifts (δ) are given in ppm with reference to residual protiated solvent as the internal standard [$^1H$ NMR: $CDCl_3$ (1H, 7.26 ppm), $(CD_3)_2CO$ ($^1H$, 2.05), $C_6D_6$ (1H, 7.16); $^{13}C$ NMR: $CDCl_3$ (77.2), $(CD_3)_2CO$ (29.8, 206.3), $C_6HD$ (128.1)].

High-resolution mass measurements were carried out using a Waters SYNAPT G2-Si system with QuanTof analyzer on an Agilent 6550 QTOF system.

Column chromatography was performed on silica gel.

All reactions sensitive to air or moisture were conducted under argon atmosphere in dry SPS (Solvent Purification System-Cabinet Mount SPS from Pure Process Technology) or freshly distilled solvents (e.g., tetrahydrofuran (THF) over sodium benzophenone and all other over $CaH_2$ unless otherwise noted). All other solvents and reagents were used as obtained from commercial sources without further purification unless otherwise noted. Room temperature (rt) is around 23° C.

Example 1

Preparation of Compound 6

Scheme 2 Synthesis of S1 and S2

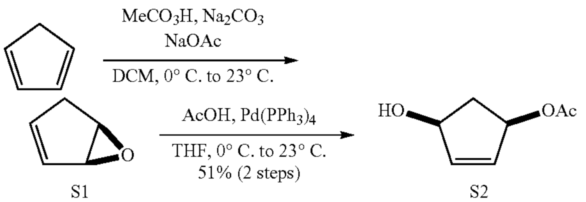

S1 S2

Compound S1: S1 was prepared with slight modifications to the known procedure. Jung et al., Total synthesis of the epoxy isoprostane phospholipids PEIPC and PECPC, Organic Letters 7(18): 3933-3935 (2005). To a rapidly stirring solution of freshly cracked cyclopentadiene (23 mL, 273 mmol, 1.0 eq.) in anhydrous dichloromethane (DCM) (160 mL) under an argon atmosphere was added anhydrous sodium carbonate (46 g, 438 mmol, 1.6 eq.) Note the sodium carbonate should be added slow enough to maintain stirring (adding too quickly can cause the stir bar to stop moving).

The solution was cooled to 0° C. in an ice bath, and then a solution of sodium acetate (1.76 g, 21.4 mmol, 0.03 eq.) in peracetic acid (32% in AcOH, 28.8 mL, 136.5 mmol, 0.5 eq.) was added dropwise over a 35-minute period. The solution was left to stir at 0° C. for another 10 minutes, and then to room temperature for 1 hour. After this time, the reaction mixture was filtered through a fritted filter with DCM (200 mL), and then the filtrate was carefully concentrated under reduced pressure at 0° C. to give around 125 mL of a solution of product epoxide S1 in DCM. (Note that distillation of the crude is advised against, as it has been reported that (especially on larger scales) the epoxide can explosively decompose at elevated temperatures.)

The amount of product was estimated to be 8.19 g (0.2 M in DCM) based on proton nuclear magnetic resonance (H-NMR) integration.

The analytical data was in agreement with the referenced procedure: $^1$H NMR (500 MHz, $CDCl_3$) δ 6.14 (m, 1H), 5.98 (dd, J=5.8, 2.2 Hz, 1H), 3.90 (dd, J=5.8, 3.0 Hz, 1H), 3.81 (m, 1H), 2.62 (ddd, J=19.2, 4.2, 2.2 Hz, 1H), 2.38 (ddt, J=19.1, 3.5, 2.1 Hz, 1H) $^{13}$C NMR (125 MHz, $CDCl_3$) δ 137.9, 131.3, 59.2, 56.9, 35.6.

Compound S2: This compound was prepared with slight modifications to the known procedure.[1] In a flame dried 250 mL flask, $Pd(PPh_3)_4$ (230 mg, 0.199 mmol, 0.002 eq.) was combined with anhydrous THF (50 mL) to give a clear, yellow solution. The solution was cooled in an ice bath to 0° C., and then glacial acetic acid (5.7 mL, 100 mmol, 1.0 eq.) was added all at once. To the solution, the DCM solution of epoxide S1 (approximately 8.19 g, 100 mmol, 0.2 M in DCM) was then added dropwise via a cannula over a 20-min period. The solution was left to stir at 0° C. for another 1 hour, and then to room temperature until the solution changed to dark orange (1 hour). The crude reaction mixture was concentrated under reduced pressure, filtered through a short silica plug followed by ether (500 mL), and then concentrated again under reduced pressure to give a dark orange oil. This oil was purified by flash chromatography (3:1 to 1:1 hexanes/EtOAc) to give mono-acetylated diol S2 (9.91 g, 51% over 2 steps (based on mol of peracetic acid)) as an oil, which solidified in the fridge to a yellow solid.

The analytical data was in agreement with the referenced procedure: $^1$H NMR (500 MHz, $CDCl_3$) δ 6.10 (m, 1H), 5.97 (m, 1H), 5.48 (m, 1H), 4.71 (m, 1H), 2.79 (dt, J=14.6, 7.4 Hz, 1H), 2.04 (s, 3H), 1.64 (dt, J=14.5, 3.9 Hz, 1H). $^{13}$C NMR (125 MHz, $CDCl_3$) δ 170.8, 138.5, 132.6, 77.1, 74.9, 40.5, 21.2.

Scheme 3 Synthesis of S3 and S4 from S2

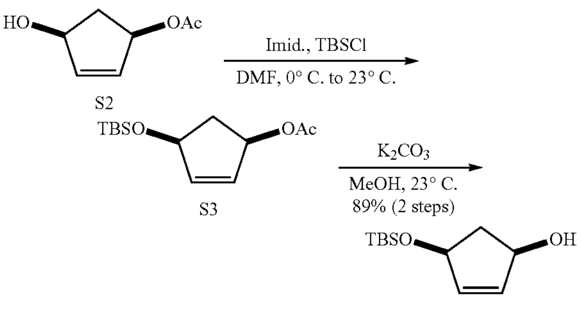

S2 S3 S4

Compound S3: Following the known procedure, in a flame dried 250 mL round bottom flask, mono-acetylated diol S2 (4.41 g, 31 mmol, 1.0 eq.) was combined with anhydrous dimethylformamide (DMF) (40 mL) and imidazole (3.17 g, 46.5 mmol, 1.5 eq.) under an argon atmosphere. Ghosh et al. (2015), supra. The solution was cooled to 0° C., and then tert-Butyldimethylsilyl chloride (TBSCl) (5.61 g. 37 mmol, 1.2 eq.) in anhydrous DMF (20 mL) was added over a 30-minute period.

The solution was left to slowly stir to room temperature overnight (20 hours), and then was cooled again to 0° C. and quenched with 10 mL of water. The reaction mixture was diluted with deionized (DI) water (200 mL) and extracted with ether (3×100 mL), and then the combined organic phases were back extracted with DI water (100 mL), dried over sodium sulfate, filtered, and concentrated under reduced pressure to give a crude yellow oil. This oil was purified by flash chromatography (95:5 hexanes/EtOAc) to give acetylated-tert-Butyldimethylsilyl (TBS) diol S3 as a colorless oil.

The analytical data was in agreement with the referenced procedure: $^1$H NMR (500 MHz, $CDCl_3$) δ 5.97 (m, 1H), 5.88 (m, 1H), 5.45 (m, 1H), 4.71 (m, 1H), 2.80 (dt, J=13.8, 7.4 Hz, 1H), 2.04 (s, 3H), 1.60 (dt, J=13.8, 5.1 Hz, 1H), 0.89 (s, 9H), 0.08 (s, 6H). $^{13}$C NMR (125 MHz, $CDCl_3$) δ 170.9, 138.9, 131.2, 77.0, 74.9, 41.2, 25.9, 21.2, 18.2, −4.6.

Compound S4: Following the known procedure, in a 250 mL round bottom flask, acetylated-TBS diol S3 (7.95 g, 31.0 mmol, 1.0 eq.) was combined with MeOH (160 mL) and $K_2CO_3$ (4.71 g, 34.1 mmol, 1.1 eq.). Ghosh et al. (2015), supra. After stirring at room temperature for 4.5 hours, the reaction mixture was concentrated under reduced pressure, and diluted with DI water (100 mL) and ether (150 mL). The organic phase was collected, and then the aqueous (aq.) phase was washed with more ether (2×100 mL). The combined organic phases were then dried over magnesium sulfate, filtered, concentrated under reduced pressure, and purified by flash chromatography (8:1 to 4:1 hexanes/ethyl acetate (EtOAc)) to give mono-TBS diol S4 (5.94 g, 89%, over 2 steps) as a clear, colorless oil.

The analytical data was in agreement with the referenced procedure. $^{1}$H NMR (500 MHz, $CDCl_3$) δ 5.94 (m, 1H), 5.89 (m, 1H), 4.66 (m, 1H), 4.59 (m, 1H), 2.68 (dt, J=13.8, 6.9 Hz, 1H), 1.50 (dt, J=13.8, 4.6 Hz, 1H), 0.89 (s, 9H), 0.08 (s, 6H). $^{13}$C NMR (125 MHz, $CDCl_3$) δ 137.1, 135.6, 75.2, 75.1, 44.8, 25.9, 18.2, −4.6.

Scheme 4 Synthesis of Compound 6 from S4

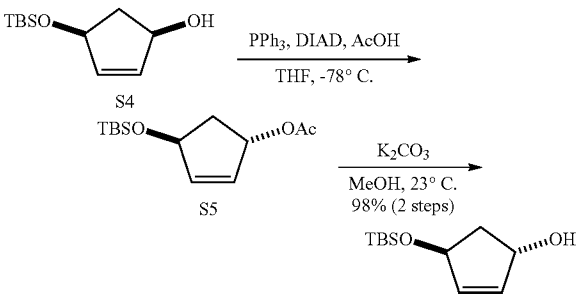

S4

S5

6

Compound S5: Following a slight variation of the known procedure, in a flame dried 250 mL flask mono-TBS diol S4 (5.94 g, 27.7 mmol, 1.0 eq.) was combined with anhydrous THF (140 mL) and $PPh_3$ (14.54 g, 55.4 mmol, 2.0 eq.) under an argon atmosphere. Fröhner et al., Regiospecific synthesis of mono-N-substituted indolopyrrolocarbazoles, Organic Letters 7: 4573 (2005).

The solution was cooled to −78° C., and then glacial acetic acid (3.2 mL, 55.4 mmol, 2.0 eq.) was added all at once, followed by the dropwise addition of DIAD (10.9 mL, 55.4 mmol, 2.0 eq.) over a 30-minute period. The solution was left to stir at −78° C. for 6 hours and then quenched with 45 mL of 10% $NaHCO_3$ and left to warm to room temperature. The reaction mixture was extracted with ether (2×140 mL), and then the combined organic phases were dried over magnesium sulfate, filtered, and concentrated under reduced pressure to give a yellow solid. This solid was sonicated with 30 mL of 95:5 pentanes/EtOAc to give a white suspension, which was filtered through a silica plug (moistened with 95:5 pentanes/EtOAc) followed by another 400 mL of 95:5 pentanes/EtOAc. The resulting filtrate was concentrated to give 7.0 g of fairly pure acetylated-TBS diol S5 as a yellow oil which was used directly in the next step without further purification.

Compound 6: Following the known procedure, in a 250 mL round bottom flask acetylated-TBS diol S5 (7.0 g, approx. 27.3 mmol, 1 eq.) was combined with MeOH (140 mL) and $K_2CO_3$ (4.15 g, 30 mmol, 1.1 eq.). Fröhner et al. (2005), supra. After stirring at room temperature for 3 hours, the reaction mixture was concentrated, and diluted with ether (150 mL) and DI water (100 mL). The organic phase was collected, and then the aq. phase was washed with more ether (2×100 mL). The combined organic phases were then dried over magnesium sulfate, filtered, and concentrated to give pure mono-TBS diol 6 (5.85 g, 98% over 2 steps) as a colorless oil (no chromatography required).

Using the above procedure, more than decagram of compound 6 was prepared.

$^{1}$H NMR (500 MHz, $CDCl_3$) δ 5.94 (m, 2H), 5.09 (m, 1H), 5.01 (m, 1H), 2.04 (m, 2H), 0.89 (s, 9H), 0.08 (s, 6H). $^{13}$C-NMR (125 MHz, $CDCl_3$) δ 138.3, 135.6, 76.6, 76.2, 44.4, 25.9, 18.2, −4.6.

Example 2

Scheme 5 Synthesis of Compound 18

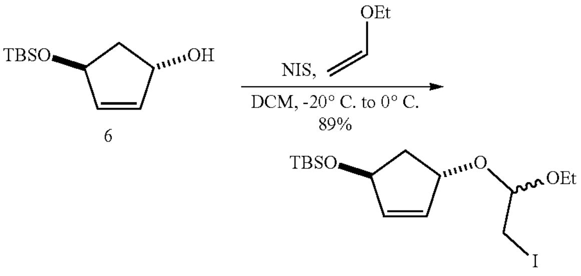

6

18

Compound 18: In a flame dried 250 flask, mono-TBS diol 6 (5.85 g, 27.3 mmol, 1.0 eq.) was combined with anhydrous DCM (175 mL) and N-iodosuccinimide (NIS) (6.75 g, 30.0 mmol, 1.1 eq.) under argon, and then cooled to −20° C. To the solution, ethyl vinyl ether (5.2 mL, 54.6 mmol, 2.0 eq.) was then added over a 30-minute period (solution changed from pink to light yellow). After the addition, the solution was left to stir at −20° C. for another 30 minutes, and then to 0° C. for 4 hours. After this time, the solution was quenched with 15 mL $Na_2S_2O_3$, left to warm to room temperature, and diluted with DCM (50 mL) and DI water (50 mL). The organic phase was collected, and the aq. phase was washed with more DCM (50 mL). The combined organic phases were then dried over magnesium sulfate, filtered, and concentrated under reduced pressure to give a cloudy yellow oil, which was filtered through a short silica plug with 150 mL of 95:5 hexanes/EtOAc. The resulting filtrate was then concentrated under reduced pressure and purified by flash chromatography (96:4 hexanes/$Et_2O$) to give iodo-acetal 18 (9.97 g, 89%) as a colorless oil and inconsequential mixture of acetal diastereomers.

$^{1}$H NMR (500 MHz, $CDCl_3$) δ 5.96 (m, 2H), 5.06 (m, 1H), 4.91 (m, 1H), 4.68 (m, 1H), 3.71-3.51 (m, 2H), 3.2 (m, 2H), 2.19 (m, 1H), 1.95 (m, 1H), 1.23 (m, 3H), 0.88 (s, 9H), 0.08 (s, 6H).

$^{13}$C NMR (125 MHz, $CDCl_3$) δ 139.3, 139.2, 133.4, 133.0, 101.6, 101.5, 81.2, 80.8, 76.4, 76.3, 62.0, 61.3, 42.2, 41.5, 25.9, 18.2, 15.2, 15.1, 6.0, 5.9, −4.6.

IR (ATR): 2935, 2928, 2884, 2856, 2162, 2035, 2017, 1970, 1471, 1462, 1414, 1366, 1251, 1177, 1102, 1050, 1030, 1002 $cm^{-1}$.

HRMS (ESI): m/z Calc. for $C_{15}H_{29}IO_3SiNa$ $[M+Na]^+$: 453.0823, found: 435.0821.

Example 3

Scheme 6 Synthesis of Compound 17

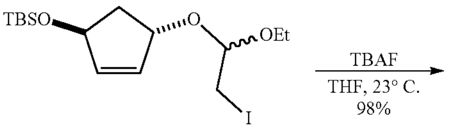

18

-continued

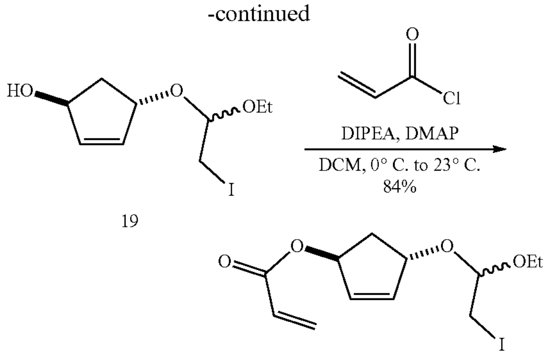

19

17

Optionally, an acrylate side chain can be additionally attached to compound 18 to produce an acrylate tethered iodo-acetal 17, which can set the stage for the key Ueno-Stork-type cyclization (described below). As represented in FIG. 3, however, tricyclic lactone 16 could not be isolated.

Compound 19: In a flame dried 20 mL vial, iodo-acetal 18 (200 mg, 0.48 mmol, 1.0 eq.) was combined with anhydrous THF (8 mL) under argon, and then tetrabutylammonium fluoride (TBAF) (1.0 M solution in THF, 0.53 mL, 0.53 mmol, 1.0 eq.) was added all at once. The solution was left to stir at room temperature for 1 hour, and then was concentrated under reduced pressure and purified directly by flash chromatography (2:1 hexanes/EtOAc) to give deprotected iodo-acetal 19 (142 mg, 98%) as a clear, colorless oil and inconsequential mixture of acetal diastereomers.

$^1H$ NMR (500 MHz, $CDCl_3$) δ 6.04 (m, 2H), 5.03 (m, 1H), 4.96 (m, 1H), 4.68 (m, 1H), 3.70-3.50 (m, 2H), 3.23-3.13 (m, 2H), 2.26-2.19 (m, 1H), 2.07-1.96 (m, 1H), 1.73 (bs, 1H), 1.26-1.20 (m, 3H).

$^{13}C$ NMR (125 MHz, $CDCl_3$) δ 138.1, 138.0, 135.2, 134.8, 101.7, 101.5, 81.0, 80.7, 76.0, 75.9, 62.0, 61.4, 42.0, 41.3, 15.2, 15.1, 5.8.

IR (ATR): 3371, 3060, 2974, 2923, 2851, 1481, 1416, 1350, 1316, 1272, 1177, 1102, 1040, 1000 $cm^{-1}$.

HRMS (ESI): m/z Calc. for $C_9H_{15}IO_3Na$ $[M+Na]^+$: 320.9958, found: 320.9957.

Compound 17: In a flame dried 2-dram vial, deprotected iodo-acetal 19 (100.0 mg, 0.335 mmol, 1.0 eq.) was combined with anhydrous DCM (1 mL), DMAP (7.5 mg, 0.061 mmol, 0.18 eq.) and DIPEA (0.18 mL, 1.01 mmol, 3.0 eq.) under an argon atmosphere. The solution was cooled to 0° C., and then a solution of acryloyl chloride (0.07 mL, 0.839 mmol, 2.5 eq.) in DCM (1 mL) was added slowly over a 5-minute period (solution turned yellow). The solution was left to stir at 0° C. for another 15 minutes, and then to room temperature for 45 minutes. The solution was then quenched with DI water (1 mL), diluted with 30 mL EtOAc (30 mL), and washed with DI water (10 mL) and brine (10 mL). The organic phase was collected, dried over sodium sulfate, filtered and concentrated under reduced pressure to give a yellow oil, which was purified by flash chromatography (10:1 hexanes/EtOAc) to give acrylate tethered iodo-acetal 17 (100 mg, 84%) as a colorless oil and inconsequential mixture of acetal diastereomers.

$^1H$ NMR (500 MHz, $CDCl_3$) δ 6.38-6.31 (m, 2H), 6.13 (m, 1H), 6.09-6.00 (m, 2H), 5.83 (m, 1H), 5.78 (m, 1H), 4.95 (m, 1H), 4.68 (m, 1H), 3.68-3.49 (m, 2H), 3.22-3.14 (m, 2H), 2.29-2.13 (m, 2H), 1.26-1.15 (m, 3H).

$^{13}C$ NMR (125 MHz, $CDCl_3$) δ 166.0, 138.0, 137.6, 133.5, 130.9, 128.5, 101.7, 101.6, 80.4, 80.2, 78.8, 78.7, 61.9, 61.4, 38.6, 38.0, 15.2, 15.1, 5.6, 5.5.

IR (ATR): 3066, 3037, 2976, 2890, 1717, 1635, 1619, 1405, 1369, 1339, 1293, 1268, 1184, 1121, 1102, 1027 $cm^{-1}$.

HRMS (ESI): m/z Calc. for $C_{12}H_{17}IO_4Na$ $[M+Na]^+$: 375.0063, found: 375.0064.

Example 4

Scheme 7 Synthesis of Compound 20

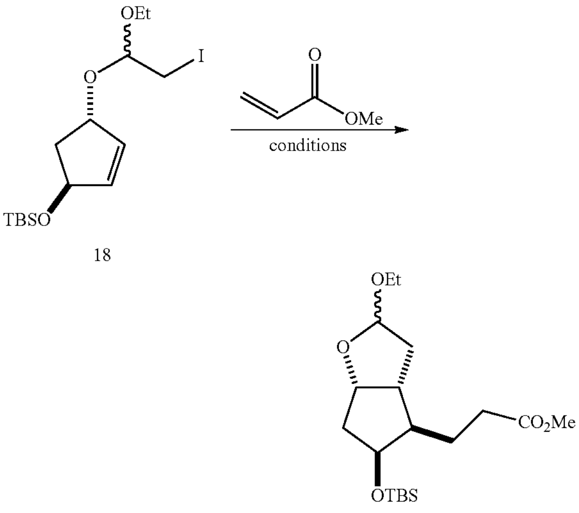

18

20 a. Stork radical cascade
AIBN (0.1 eq.), $nBu_3SnCl$ (0.1 eq.)
$NaCNBH_3$ (1.5 eq.), MA (5.0 eq)
tBuOH (0.04M), 85° C., 72 h
61% (10.0 g scale)
b. nickel catalysis
$NiCl_2$•glyme (10 mol %)
neo (12 mol %), Zn (3 eq.), MA (1.5 eq.)
MeOH (0.2M), 40° C., 1 h
59% (0.25 g scale)
46% (3.2 g scale)
MA = methyl acrylate
neo = neocuproine Complex mixtures can be obtained under various tin-based Ueno-Stork cyclization conditions, and the acrylate tether can be cleaved when palladium, nickel, or other transition metals are used to promote a dicarbofunctionalization due to its allylic nature. Stork et al., Radical cyclization-trapping in the synthesis of natural products. A simple, stereocontrolled route to prostaglandin F2.alpha, J. Am. Chemical Soc'y 108(20): 6384-6385 (1986); Firmansjah & Fu, Intramolecular heck reactions of unactivated alkyl halides, J. Am. Chemical Soc'y 129, 11340-11341 (2007); Wang et al., Irradiation-induced heck reaction of unactivated alkyl halides at room temperature, J. Am. Chemical Soc'y, 139(50): 18307-18312 (2017); Nguyen et al., Engaging unactivated alkyl, alkenyl and aryl iodides in visible-light-mediated free radical reactions, Nature Chemistry 4: 854-859 (2012); Kim & Lee, Nickel-catalyzed reductive cyclization of organohalides, Organic Letters 13(8): 2050-2053 (2011).

Compound 20: There are multiple methodologies available for the preparation of Compound 20.

(a) Stork radical cascade: Stork and colleagues performed tandem radical cyclizations on similar substrates, however, their reported conditions were unsuccessful for the present case. Stork et al. (1986), supra. The procedure used instead was a modified Stork radical cascade as follows: to iodo-acetal 18 (9.97 g, 24.2 mmol 1.0 eq) in a flame dried 1-L flask under argon were added the following reagents: AIBN (397 mg, 2.4 mmol, 0.1 eq.), $NaCNBH_3$ (2.28 g, 36.3 mmol, 1.5 eq.), 590 mL tBuOH (ACS grade), methyl acrylate (10.9 mL, 120.9 mmol, 5.0 eq.) (filtered neat through basic alumina before use) and $nBu_3SnCl$ (0.73 mL, 2.4 mmol, 0.1 eq., Oakwood 90% purity). The solution was then heated to 85° C. After stirring at this temperature for 72 hours, the reaction was cooled to room temperature, and then concentrated with benzene three times to remove the tBuOH. The crude mixture was then dissolved in EtOAc (150 mL) and washed with DI water (50 mL) and brine (50 mL). The combined aqueous phases were washed with more EtOAc (2×100 mL), and then the combined organic phases were dried over magnesium sulfate, filtered and concentrated under reduced pressure to give a crude, orange oil. This oil was filtered through a silica plug with 1:1 hexanes/EtOAc (300 mL), and then the filtrate was concentrated to give a yellow oil. Purification was then performed using flash chromatography (pure hexanes to 9:1 hexanes/EtOAc) to give cyclized product 20 (5.47 g, 61%) (viscous, colorless oil) only as the desired diastereomer at the ester side chain (ester side chain on convex face of the molecule; still inconsequential mixture of acetal diastereomers).

For stereochemical confirmation see the x-ray analysis of cyclopropanol 15 (Part 2). The other diastereomer (ester on the concave face of the molecule) was not found/able to be fully characterized after column. For smaller scale reactions (<1 g), anhydrous tBuOH (from Sigma-Aldrich, Sure/Seal) was used, the reaction was stirred for 24 hours, and no aqueous workup was performed (directly filtered through silica plug with 1:1 hexanes/EtOAc).

(b) Nickel conditions: To a flame dried 2-dram vial containing iodo-acetal 18 (250 mg, 0.61 mmol, 1.0 eq.), nickel(II) chloride ethylene glycol dimethyl ether complex ($NiCl_2$·glyme) (13.3 mg, 0.061, 0.1 eq.) (weighed in glove-box) in 1.3 mL MeOH (HPLC grade) and neocuproine (15.2 mg, 0.073 mmol, 0.12 eq.) in 1.8 mL MeOH were added consecutively and all at once. The reaction mixture was stirred at room temperature for 10 minutes (reaction turned light green), and then to 40° C. for 10 minutes. After this time, Zn nanopowder (119 mg, 1.82 mmol, 3.0 eq.) and methyl acrylate (82 uL, 0.91 mmol, 1.5 eq.) (filtered neat through basic alumina before using) were added consecutively and all at once, and then the reaction was left to stir at 40° C. for another 1 hour. After cooling to room temperature for 5 minutes, the reaction was filtered through a short celite pad followed by EtOAc (100 mL). The crude filtrate was then concentrated to give an orange solid, which was purified by flash chromatography (pure hexanes to 9:1 hexanes/EtOAc) to give cyclized product 20 (135 mg, 59%) only as the desired diastereomer at the ester side chain.

Using the modified Stork conditions, cyclization product 20 was obtained in 61% yield and exhibited excellent stereoselectivity at the newly formed stereogenic centers on up to 10 g scales. Stork et al. (1986), supra.

$^1H$ NMR (500 MHz, $CDCl_3$) δ 5.20-5.10 (m, 1H), 4.78-4.62 (m, 1H), 4.27 (m, 1H), 3.71-3.64 (m, 4H), 3.43-3.31 (m, 1H), 2.59-2.25 (m, 3H), 2.15-1.48 (m, 7H), 1.20-1.10 (m, 3H), 0.86 (m, 9H), 0.03 (m, 6H).

$^{13}C$ NMR (125 MHz, $CDCl_3$) δ 174.2, 174.1, 106.2, 106.0, 85.2, 82.5, 76.2, 75.8, 62.4, 62.3, 51.5, 51.4, 51.3, 50.4, 45.8, 45.3, 43.9, 41.5, 39.2, 37.9, 32.8, 32.6, 25.8, 24.6, 23.9, 18.0, 15.2, 15.1, −4.4, −4.5, −5.0.

IR (ATR): 2951, 2930, 2898, 2857, 1740, 1472, 1463, 1436, 1361, 1334, 1291, 1252 $cm^{-1}$.

HRMS (ESI): m/z Calc. for $C_{19}H_{36}O_5SiNa$ $[M+Na]^+$: 395.2224, found: 395.2227.

Example 5

Scheme 8 Synthesis of Compound 21

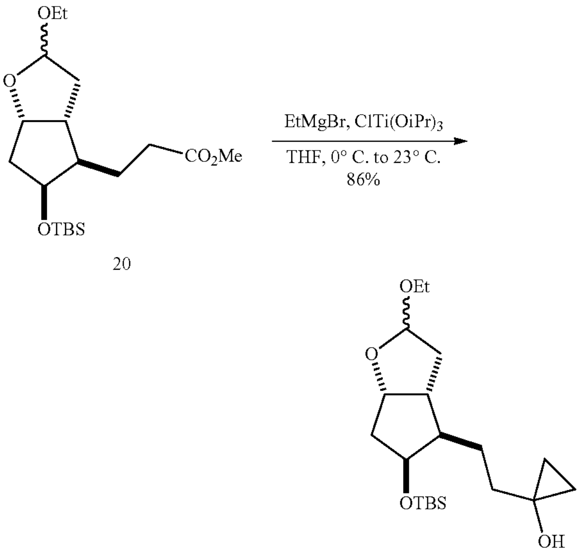

20

21

Compound 21: The reaction was low yielding using the conventional protocols. Kulinkovich et al. (1991), supra. However, the reaction was successful using stoichiometric amounts of $ClTi(OiPr)_3$ as set forth below. Kingsbury & Corey (2005), supra.

More specifically, in a flame dried 250 mL flask, cyclized product 20 (3.72 g, 9.98 mmol, 1.0 eq.), was combined with $ClTi(OiPr)_3$ (0.46 M solution made from anhydrous THF, 104 mL, 48 mmol, 4.8 eq.) under argon. The solution was cooled to 0° C., and then EtMgBr (1.0 M in THF, 96 mL, 96 mmol, 9.6 eq.) was added dropwise over a 1.5-hour period (solution became dark brown/black). The solution was left to stir at 0° C. for another 1 hour, and then to room temperature for 30 minutes. The reaction was then quenched by the addition EtOAc (15 mL) followed by saturated (sat.) aqueous $NH_4Cl$ (15 mL).

The solution was then filtered through a celite pad, followed by EtOAc (250 mL), and then the filtrate was concentrated under reduced pressure, and diluted with EtOAc (150 mL) and brine (100 mL). The organic phase was collected, and then the aq. phase was washed with more EtOAc (100 mL). The combined organic phases were dried over magnesium sulfate, filtered, concentrated under reduced pressure, and purified by column (4:1 hexanes/EtOAc) to give cyclopropanol 21 (3.19 g, 86%) as a colorless oil and inconsequential mixture of acetal diastereomers.

$^1H$ NMR (500 MHz, $CDCl_3$) δ 5.20-5.10 (m, 1H), 4.79-4.61 (m, 1H), 4.28 (m, 1H), 3.74-3.64 (m, 1H), 3.44-3.33 (m, 1H), 2.61-2.37 (m, 1H), 2.15-1.96 (m, 2H), 1.85-1.37 (m, 8H), 1.21-1.11 (m, 3H), 0.86 (m, 9H), 0.73 (m, 2H), 0.43 (m, 2H), 0.05-0.00 (m, 6H).

$^{13}C$ NMR (125 MHz, $CDCl_3$) δ 106.1 105.9, 85.3, 82.3, 76.0, 75.9, 62.5, 62.3, 56.0, 55.9, 52.1, 50.9, 46.1, 45.5, 43.9, 41.4, 39.4, 37.9, 36.9, 36.7, 25.8, 25.1, 24.6, 18.0, 15.3, 15.2, 13.6, 13.5, 13.4, 13.3, −4.3, −4.4, −4.9.

IR (ATR): 3427, 2953, 2929, 2856, 1714, 1462, 1403, 1375, 1362, 1287, 1253, 1155, 1108, 1090, 1055, 1006 $cm^{-1}$.

HRMS (ESI): m/z Calc. for $C_{20}H_{38}O_4SiNa$ $[M+Na]^+$: 393.2431, found: 393.2431.

Example 6

Scheme 9 Deprotection of Compound 21

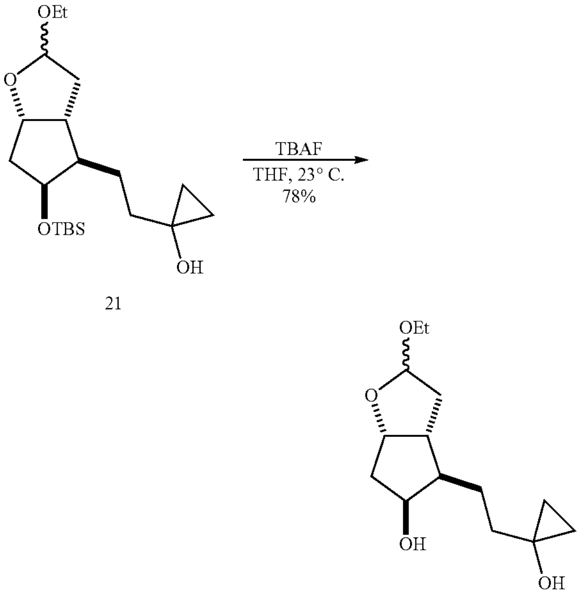

21

15

A Kulinkovich reaction was performed, followed by TBS-ether deprotection to provide cyclopropanol 15 (compound 15 was confirmed by x-ray analysis (CCDC 2089935, which contains the supplementary crystallographic data for compound 15)). Notably, while the reaction was not successful under Kulinkovich's originally reported catalytic conditions, stoichiometric amounts of $ClTi(OiPr)_3$ were subsequently used, which resulted in a smooth reaction. See Kulinkovich et al., Titanium(IV) isopropoxide-catalyzed formation of 1-substituted cyclopropanols in the reaction of ethylmagnesium bromide with methyl alkanecarboxylates, Synthesis 234 (1991) and Kingsbury & Corey, Enantioselective total synthesis of isoedunol and β-araneosene featuring unconventional strategy and methodology, J. Am. Chemical Soc'y 127(40): 13813-13815 (2005); also see Ma et al. (2018), supra.

Compound 15: In a flame dried 250 mL flask, cyclopropanol 21 (2.7 g, 7.3 mmol, 1.0 eq.) was combined with anhydrous THF (115 mL) under an argon atmosphere and cooled to 0° C. To the solution, TBAF (1 M solution in THF, 7.3 mL, 7.3 mmol, 1.0 eq.) was added dropwise over a 30-min period, and then the solution was left to slowly warm to room temperature. After stirring for 43 h at room temperature, the reaction mixture was concentrated and diluted with EtOAc (50 mL) and DI water (50 mL). The organic phase was collected, and then the aq. phase was washed with more EtOAc (2×50 mL). The combined organic phases were then dried over sodium sulfate, filtered, concentrated under reduced pressure, and purified by flash chromatography (3:1 EtOAc/hexanes) to give deprotected cyclopropanol 15 (1.46 g, 78%) as a white solid. On smaller scale (<1 g) the reaction was done in less time (<1 day) and gave slightly higher yields (80-85%).

$^1H$ NMR (500 MHz, $CDCl_3$) δ 5.22-5.13 (m, 1H), 4.88-4.67 (m, 1H), 4.42 (m, 1H), 3.76-3.65 (m, 1H), 3.45-3.33 (m, 1H), 2.59-2.40 (m, 1H), 2.27-2.06 (m, 3H), 1.98-1.82 (m, 2H), 1.80-1.50 (m, 6H), 1.17 (m, 3H), 0.76 (m, 2H), 0.47 (m, 2H).

$^{13}C$ NMR (125 MHz, $CDCl_3$) δ 106.1, 105.8, 85.2, 82.4, 75.8, 75.7, 62.5, 62.4, 55.5, 55.4, 51.6, 50.6, 46.4, 46.1, 43.7, 41.1, 39.0, 37.8, 36.8, 36.6, 24.9, 21.1, 15.2, 15.1, 14.3, 14.2, 13.3, 13.2.

IR (ATR): 3352, 3083, 2972, 2936, 1647, 1444, 1417, 1405, 1373, 1333, 1290, 1253, 1209, 1184, 1163, 1106, 1083, 1052, 1007 $cm^{-1}$.

HRMS (ESI): m/z Calc. for $C_{14}H_{24}O_4Na$ $[M+Na]^+$: 279.1567, found: 279.1569.

Example 7

Scheme 10 Compound 14

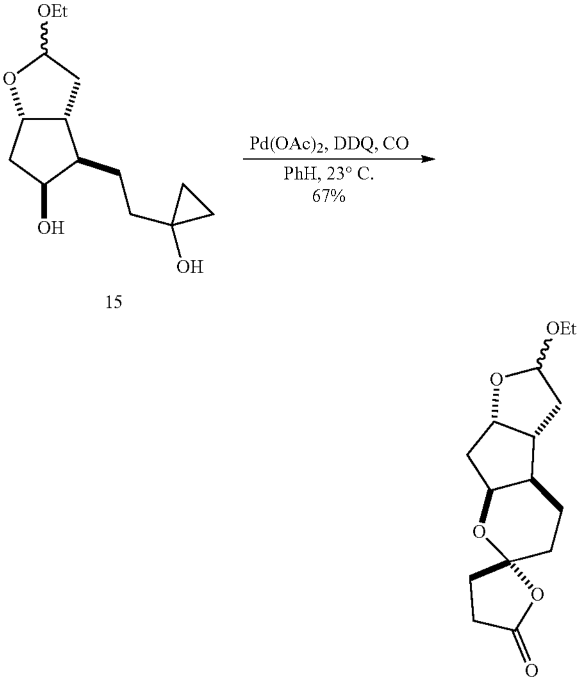

15

14

With a deprotected cyclopropanol (compound 15) in hand, the key carbonylative cyclization can be pursued. Under previously reported conditions for oxaspirolactone synthesis, tetracyclic product 14 was formed with an acceptable yield (e.g., 40-50%). Davis et al. (2016), supra. However, traces of acetic acid generated from the catalyst can result in partial trans-acetalization of the ethyl acetal with hydroquinone to give 22. The resulting mixture was nontrivial to separate. Hydrolysis of the acetal mixture did not simplify the purification, with the resulting hydroquinone being equally difficult to separate.

Compound 14: Following the previously reported conditions ($Pd(OAc)_2$ and 2,3-dichloro-5,6-dicyano-p-benzoginone (DDQ)) for synthesizing bicyclic lactones, in a flame dried 100 mL flask, cyclopropanol 15 (68 mg, 0.265 mmol, 1.0 eq.) was combined with anhydrous benzene (26 mL) to give a 0.01 M solution. To the solution, DDQ (120 mg, 0.530 mmol, 2.0 eq.) was added (solution turned bright orange) and then the flask was evacuated/backfilled with CO three times. $Pd(OAc)_2$ (6 mg, 0.027 mmol, 0.1 eq) was added all at once, and then the solution was left to stir at room temperature for 20 hours (with CO balloon). Cai et al., Catalytic hydrooxycyclopropanol ring-opening carbonylative lactonization to fused bicyclic lactones, J. Am. Chemical Soc'y 142(32): 13677-13682 (2020). The reaction was filtered through a celite pad with DCM, and then the filtrate was concentrated under reduced pressure and purified by flash chromatography (3:1 hexanes/EtOAc) to give oxaspirolactone 14 (50 mg, 67%) as a colorless oil.

This process was efficient for synthesizing oxaspirolactones in these circumstances. After replacing 1,4-benzoquinone with DDQ, 14 was cleanly produced in even higher yield (67%) without any evidence of trans-acetalization. Also, the use of commercially available $Pd(OAc)_2$ to replace $[Pd(neoc)(OAc)]_2(OTf)_2$ simplified the procedure. Under both reaction conditions, only the desired stereochemistry was obtained at the spirocenter with the lactone oxygen in the axial position due to the anomeric effect.

$^1H$ NMR (500 MHz, $CDCl_3$) δ 5.26-5.15 (m, 1H), 4.85-4.68 (m, 1H), 4.41-4.34 (m, 1H), 3.76-3.67 (m, 1H), 3.46-3.34 (m, 1H), 2.80-2.60 (m, 2H), 2.52-2.42 (m, 1H), 2.35-1.96 (m, 6H), 1.93-1.63 (m, 5H), 1.22-1.12 (m, 3H).

$^{13}C$ NMR (125 MHz, $CDCl_3$) δ 176.6, 176.5, 107.8, 107.7, 106.2, 106.1, 86.0, 83.5, 78.7, 78.2, 62.7, 62.6, 43.6, 42.8, 42.4, 42.2, 42.1, 39.7, 38.3, 37.5, 34.7, 34.6, 28.2, 28.1, 27.9, 19.3, 18.9, 15.3, 15.2.

IR (ATR): 2971, 2931, 2867, 1775, 1447, 1420, 1378, 1334, 1287, 1267, 1245, 1205, 1193, 1159, 1117, 1103, 1084, 1044, 1024, 1002 $cm^{-1}$.

HRMS (ESI): m/z Calc. for $C_{15}H_{22}O_5Na$ $[M+Na]^+$: 305.1360, found: 305.1361.

Example 8

Scheme 11 Compound 14 Hydrolysis to Compound 23

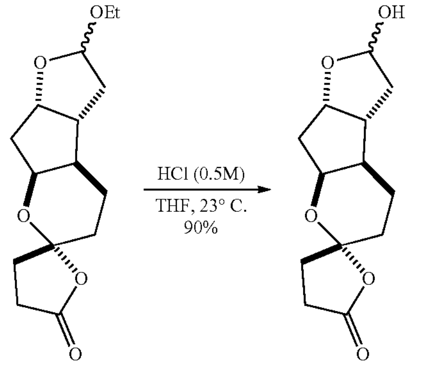

14

23

HCl-promoted hydrolysis to hemi-acetal 23 proceeded smoothly, setting the stage for a one-carbon homologation.

Compound 23: In a 2-dram vial, oxaspirolactone 14 (13.9 mg, 0.049 mmol) was combined with THF (0.4 mL) and 0.5 M aq. HCl (0.6 mL). After stirring for 6 hours, the reaction mixture was diluted with EtOAc (10 mL) and DI water (1 mL). The organic phase was collected, and the aqueous phase was washed with more EtOAc (2×10 mL). The combined organic phases were dried over sodium sulfate, concentrated under reduced pressure, and filtered through a pipette silica column followed by around another 15 mL of EtOAc. The filtrate was then concentrated under reduced pressure to give hemiacetal 23 (12 mg, 90%) which was used immediately in the next step (hemi-acetal 23 was freshly prepared each time for the olefination and alkynylation experiments).

$^1H$ NMR (500 MHz, $CDCl_3$) δ 5.68-5.58 (m, 1H), 4.88-4.77 (m, 1H), 4.39 (m, 1H), 2.81-2.65 (m, 3H), 2.51-2.44 (m, 1H), 2.40-1.64 (m, 11H).

$^{13}C$ NMR (125 MHz, $CDCl_3$) δ 176.7, 176.6, 107.8, 107.7, 101.3, 100.8, 86.5, 83.9, 78.5, 78.3, 43.4, 42.8, 42.7, 42.6, 42.4, 39.8, 39.0, 37.9, 34.7, 28.2, 28.1, 27.8, 19.1, 18.9.

IR (ATR): 3424, 2927, 2856, 1771, 1552, 1449, 1379, 1327, 1286, 1266, 1246, 1203, 1121, 1108, 1070, 1043, 1021, 1001 $cm^{-1}$.

HRMS (ESI): m/z Calc. for $C_{13}H_{18}O_5Na$ $[M+Na]^+$: 277.1046, found: 277.1048.

Surprisingly, however, under various Wittig conditions, olefination of hemi-acetal 23 was unsuccessful. Using standard Wittig conditions, no reaction occurred at low temperatures and complex mixtures were obtained at higher temperatures; under Lebel's salt free Wittig conditions, no reaction occurred after days of stirring. Alkynylation to 24 using the Seyferth or Bestmann reagent was also pursued, however, only meager yields were obtained (<5%). For protocols, see Lebel et al., Methylenation of aldehydes: Transition metal catalyzed formation of salt-free phosphorus ylides, Angewandte Chemie Int'l Ed. 113(15): 2971-2974 and Lebel & Paquet, Rhodium-catayzed methylenation of aldehydes, J. Am. Chemical Soc'y 126: 320-328 (2004).

Example 9

Scheme 12 Compound 25

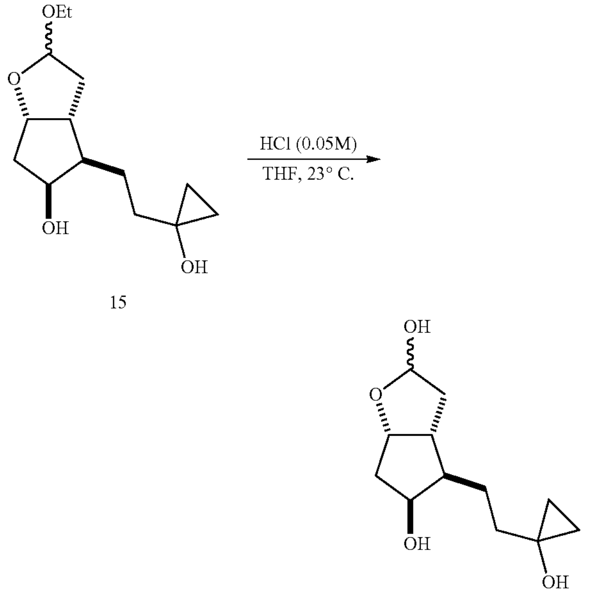

15

25

The unsuccessful one-carbon homologation of 23 prompted a redirection and, with the data mind, it was contemplated the olefination could be more feasible without the sensitive oxaspirolactone present. Accordingly, cyclopropanol 15 was chosen as an appropriate candidate as it does not require extensive modification of the present methodology. While it was expected that cyclopropanol would likely survive mild acetal hydrolysis conditions, the methylenation was a formidable challenge.

To this end, hydrolysis of compound 15 proceeded smoothly in dilute HCl (0.05 M) to give hemi-acetal 25. As expected, the olefination was not as straightforward, however, the methylenation product 26 can be obtained in acceptable yield on fairly large scales.

Compound 25: In a 50 mL flask, cyclopropanol 15 (498 mg, 1.94 mmol) was combined with THF (13 mL) (Note 1) and 0.05 M aqueous HCl (19 mL). After stirring for 2 hours, the reaction mixture was quenched with $K_2CO_3$ (134 mg, 0.97 mmol) (Note 2), left to stir for 5 minutes, and then extracted with EtOAc (5×100 mL). The combined organic phases were then dried over sodium sulfate, filtered, concentrated under reduced pressure, and then concentrated an additional three times with DCM (Note 3) to give hemi-acetal 25 as a sticky solid which was briefly put under high vacuum, placed under argon atmosphere, and used directly in the next step (Wittig olefination) within one hour. Hemi-acetal 25 can be purified quickly by flash chromatography (pure EtOAc) and the purified product seems to be more stable (could be stored in fridge overnight under argon without appreciable degradation) relative to the crude, however, it was determined that using the crude directly in the Wittig olefination gives a higher yield over 2 steps.

Note 1: The data supported that solvent purification system (SPS) or freshly distilled THF worked best for the reaction. In certain instances, directly using HPLC THF should be avoided, as with some (especially older) bottles a significant byproduct formed within 10 minutes of starting the reaction.

Note 2: The reaction can be quenched just when the starting material spot becomes faint by TLC to achieve high yield (there will be 5-10% of SM remaining in the crude NMR). It can be better to stop the reaction at this point because if left to stir for too long the product begins to rapidly degrade. Reaction times are usually slightly shorter for smaller scale reactions.

Note 3: Concentrating several times with DCM appeared to help slow the degradation of the product.

$^1H$ NMR (500 MHz, $(CD_3)_2CO$) δ 5.52-5.43 (m, 1H), 4.86-4.62 (m, 2H), 4.31-4.02 (m, 2H), 3.54-3.42 (m, 1H), 2.56-2.32 (m, 1H), 2.15-1.91 (m, 3H), 1.82-1.47 (m, 6H), 0.63-0.54 (m, 2H), 0.44-0.31 (m, 2H).

$^{13}C$ NMR (125 MHz, $(CD_3)_2CO$) δ 100.6, 100.1, 84.7, 82.1, 74.9, 54.5, 54.4, 51.7, 51.1, 46.7, 46.1, 44.3, 41.6, 40.1, 38.7, 37.0, 25.0, 24.5, 13.0, 12.9.

IR (ATR): 3332, 3089, 3001, 2927, 2857, 1648, 1564, 1453, 1358, 1316, 1252, 1211, 1150, 1113, 1068, 1011 $cm^{-1}$.

HRMS (ESI): m/z Calc. for $C_{12}H_{20}O_4Na$ $[M+Na]^+$: 251.1254, found: 251.1255.

Example 10

Scheme 13 Compound 26

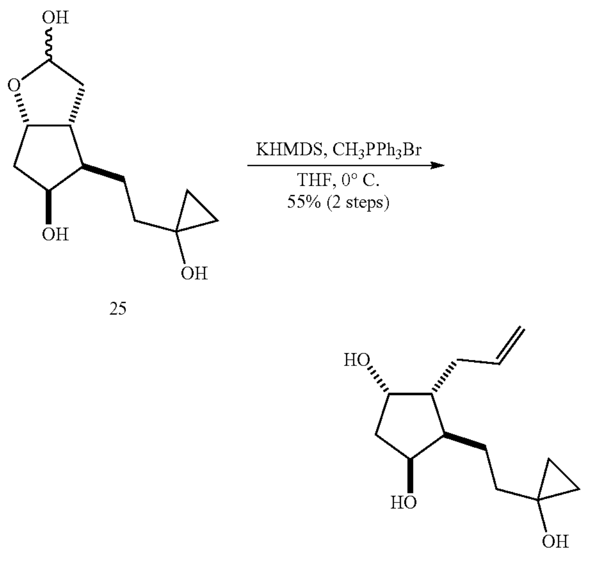

25

26

Compound 26: In a flame dried 50 mL flask, $CH_3PPh_3Br$ (2.6 g, 7.28 mmol, 3.75 eq.) was combined with anhydrous THF (50 mL) under argon, and then KHMDS (1 M solution in THF, 6.8 mL, 6.8 mmol, 3.5 eq.) (Note 1) was added all at once to give a bright yellow solution. The solution was left to stir at room temperature for 1 hour, and then to 0° C. for another 1 hour. After this time, hemi-acetal 25 (443 mg, 1.94 mmol, 1.0 eq., based on theoretical yield of the previous step) was combined with THF (4.7 mL) and added to the cooled ylide solution over an 8.5 minutes, followed by another THF (2 mL) wash of the hemi-acetal vial added over another 2 minute period. After stirring at 0° C. for another 37 minutes (Note 2), the solution was quenched with saturated aq. $NH_4Cl$ (15 mL), diluted with DI water (10 mL), and extracted with EtOAc (5×100 mL). The combined organic phases were then dried over sodium sulfate, filtered, and concentrated under reduced pressure to give a crude solid. This solid was purified by flash chromatography (pure DCM to 95:5 DCM/MeOH) to give olefin 26 (263 mg, 55%, over 2 steps) as a clear, sticky oil.

Note 1: The quality of the KHMDS can have a significant effect on the rate of the reaction. In general, for older bottles (<1 M) the rate is slower. Regardless, the reaction should be tracked very closely by TLC as described in note 2 of this Example.

Note 2: For optimal results, the reaction can be monitored around every 5 minutes by TLC. Optimally, when the notable byproduct (pure EtOAc, rf=0.3 for product, rf=0.6 for byproduct) begins to form, the reaction should be stopped.

$^1H$ NMR (500 MHz, $CDCl_3$) δ 5.92 (m, 1H), 5.14 (dd, J=17.2, 1.5 Hz, 1H), 5.05 (dd, J=10.2, 0.7 Hz, 1H), 4.45 (q, J=4.2 Hz, 1H), 4.37 (q, J=4.8 Hz, 1H), 2.30 (dt, J=14.6, 4.9 Hz, 1H), 2.15 (m, 1H), 2.02 (t, J=4.4 Hz, 2H), 1.84 (m, 1H), 1.78-1.55 (m, 6H), 0.74 (m, 2H), 0.44 (m, 2H).

$^{13}C$ NMR (125 MHz, $CDCl_3$) δ 138.2, 115.6, 72.4, 72.1, 55.4, 47.4, 46.6, 44.2, 36.9, 32.2, 22.8, 14.4, 13.2.

IR (ATR): 3270, 3077, 3005, 2973, 2926, 2907, 2861, 1641, 1454, 1437, 1415, 1379, 1345, 1328, 1285, 1219, 1202 $cm^{-1}$.

HRMS (ESI): m/z Calc. for $C_{13}H_{22}O_3Na$ $[M+Na]^+$: 249.1461, found: 249.1463.

Example 11

Scheme 14 Compound 12

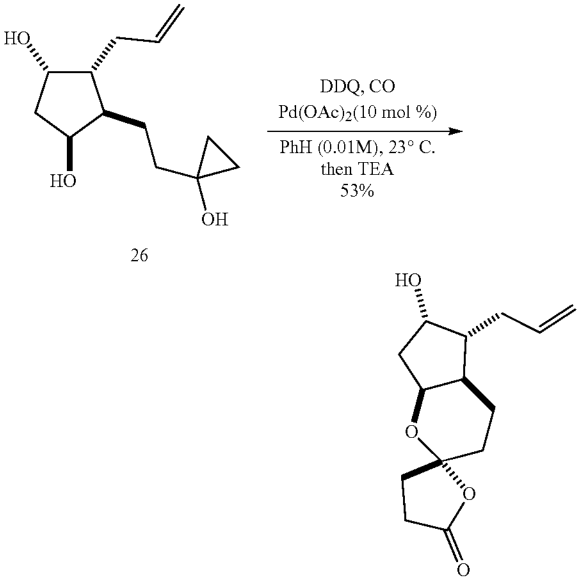

26

12

Compound 12: Following the previously reported conditions ($Pd(OAc)_2$ and 2,3-dichloro-5,6-dicyano-p-benzoginone (DDQ)) for synthesizing bicyclic lactones, in a flame dried 100 mL flask, olefin 26 (194 mg, 0.86 mmol, 1.0 eq.) was combined with 80 mL of anhydrous PhH (80 mL) (Note 1) and then DDQ (390 mg, 1.7 mmol, 2.0 eq.) (Note 2) was added all at once to give a bright orange solution. Cai et al. (2020), supra. The mixture was evacuated/backfilled with CO three times, and then $Pd(OAc)_2$ (0.013 M solution in PhH, 6.4 mL, 0.086 mmol, 0.1 eq.) (Note 3) was added all at once (no initial color change). After rapid stirring for 1 hour at room temperature (with CO balloon) (mixture looked dark orange), the reaction was quenched with 2 mL of TEA (solution turned black) and was left to stir for an additional 30 minutes (Note 4). After this time, the mixture was filtered through a short celite pad with around EtOAc (150 mL), and then the filtrate was concentrated under reduced pressure, and then filtered through a short silica plug (Note 5) followed by EtOAc (200 mL).

The filtrate was then concentrated under reduced pressure to give a dark green oil, which was purified by flash chromatography (first deactivated column with excess 95:5 hexanes/TEA, then ran 9:1 to 3:1 hexanes/EtOAc to purify product) to give oxaspirolactone 12 (115 mg, 53%) as a colorless oil (Note 6 and 7). The analytical data for this intermediate is consistent with the Sulikowski synthesis. Kimbrough et al. (2019), supra. The product was purified twice to insure high purity for the next step (Z-selective metathesis).

Note 1: THF also worked for the reaction but gave a slightly lower yield.

Note 2: Other oxidants such as BQ or $O_2$ gave little to no product for the reaction.

Note 3: $Pd(TFA)_2$ or higher catalyst loadings of $Pd(OAc)_2$ (0.25 eq.) gave slightly lower yields for the reaction.

Note 4: For optimal results, the purification steps following can be done immediately after this time (the product is not stable in the crude mixture).

Note 5: The silica plug was first deactivated with 200 mL of 95:5 EtOAc/TEA; the product seems to be acid sensitive.

Note 6: $CDCl_3$ for NMR can be neutralized with $K_2CO_3$.

Note 7: If the product is exposed to acid during the workup or purification, a byproduct with a very similar rf to the product (difficult to remove by column) can form. If the above procedure is followed carefully the amount of byproduct stays <5% in the NMR, even after prolonged storage in the refrigerator.

The data supported that the carbonylative spirolactonization was reliable. Oxaspirolactone 12 was delivered as a single stereoisomer due to the anomeric effect and in good yield despite the potential competition of a 5-exo-trig oxypalladation and other unproductive pathways.

$^1H$ NMR (500 MHz, $CDCl_3$) δ 5.90 (m, 1H), 5.12 (dd, J=17.1, 1.5 Hz, 1H), 5.03 (dd, J=10.2, 0.8 Hz, 1H), 4.35 (m, 2H), 2.72 (dt, J=17.7, 9.9 Hz, 1H), 2.45 (ddd, J=17.7, 9.5, 2.7 Hz, 1H), 2.20-2.10 (m, 4H), 2.05-1.95 (m, 3H), 1.90-1.60 (m, 5H), 1.53 (bs, 1H).

$^{13}C$ NMR (125 MHz, $CDCl_3$) δ 176.6, 137.8, 115.9, 108.1, 74.9, 72.6, 42.8, 42.1, 39.7, 34.8, 31.8, 28.6, 28.3, 18.5.

IR (ATR): 3447, 3074, 2933, 1764, 1639, 1452, 1418, 1380, 1287, 1242, 1195, 1120, 1097, 1035 $cm^{-1}$.

HRMS (ESI): m/z Calc. for $C_{14}H_{20}O_4Na$ $[M+Na]^+$: 275.1254, found: 275.1255.

Example 12

Z-Selective Metathesis

Scheme 15 Compound 12

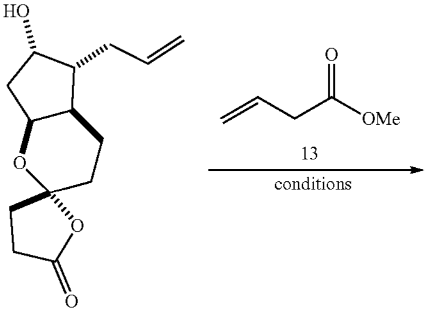

12

-continued

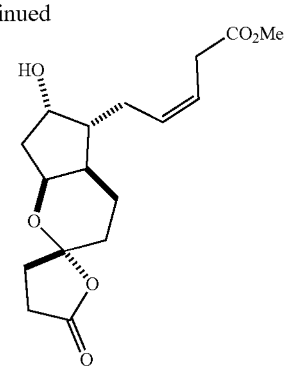

tricyclic-PGDM methyl ester (3)

Tricyclic-PGDM Methyl Ester 3:

Our next task was to find a suitable Z-selective cross metathesis condition to complete the total synthesis in just one step. For reference, see Herbert et al., Concise syntheses of insect pheromones using Z-selective cross metathesis, Angewandte Chemie Int'l Ed. 52(1), 310-314 (2013); Cannon & Grubbs, Alkene chemoselectivity in ruthenium-catalyzed Z-selective olefin metathesis, Angewandte Chemie Int'l Ed. 52(34): 9001-9004 (2013); Bronner et al., Ru-based Z-selective metathesis catalysts with modified cyclometalated carbene ligands, Chemical Science 5(10): 4091-4098 (2014); Mangold et al., Z-selective olefin metathesis on peptides: investigation of side-chain influence, preorganization, and guidelines in substrate selection, J. Am. Chemical Soc'y 136 (35): 12469-12478 (2014); For reviews see Herbert & Grubbs, Z-selective cross metathesis with ruthenium catalysts: synthetic applications and mechanistic implications, Angewandte Chemie Int'l Ed. 54(17): 5018-5024 (2015); Montgomery et al., Recent advancements in stereoselective olefin metathesis using ruthenium catalysts, Catalysts 7(3): 87 (2017); For examples in total synthesis see Chung et al., A synthesis of the chlorosulfolipid mytilipin A via a longest linear sequence of seven steps, Angewandte Chemie Int'l Ed. 52(38): 10052-10055 (2013); Li et al., Concise synthesis of $\Delta^{12}$-Prostaglandin J natural products via stereoretentive metathesis, J. Am. Chemical Soc'y 141(1): 154-158 (2019); Li et al., Enantioselective synthesis of 15-Deoxy-$\Delta^{12,14}$-Prostaglandin $J_2$, Organic Letters 21(24): 10139-10142 (2019); De Léséleuc et al., Catalytic macrocyclization strategies using continuous flow: formal total synthesis of ivorenolide A, J. Organic Chemistry 81(15): 6750-6756 (2016).

Motivation for the present method design was based, at least in part, on the rationale that a cross metathesis using the commercially available Ru—Z-Mes as catalyst and methyl 3-butenoate (13) as the partner would be a suitable starting point.

Overview: The "Metathesis Reaction Parameters" outlined in Part 1(c) were implemented herein. Table 1 provides the screened metathesis conditions for the synthesis of tricyclic-PGDM methyl ester 3.

TABLE 1

Z-Selective metathesis condition screening for the total synthesis of tricyclic-PGDM methyl ester (3)

| Entry | Solvent (0.1M) | Me-Ester (equiv.) | Z-Ru cat. (mol %) | Temp (° C.) | Time (h) | Yield (isolated) | Recovered SM | % Z |
|---|---|---|---|---|---|---|---|---|
| 1 | DCE | 10 | Mes (20)[1] | 53 | 2 | 10-15% | NA | 90 |
| 2 | DCE | 8 | Mes (20) | 53 | 2 | 35% | 40% | 90 |
| 3 | DCE | 8 | DIPP (20) | 53 | 2 | 42% | 45%[2] | 94 |
| 4 | DCE | 8 | DIPP (20) | 40 | 2 | 50% | 44% | >95 |
| 5 | DCE | 8 | DIPP (20) | 30 | 2[3] | 38% | 58% | >95 |
| 6 | DCE | 8 | DIPP (10) | 40 | 2 | 33% | 51% | >95 |
| 7 | DCE | 8 | DIPP (5) | 40 | 2 | 22% | 78% | >95 |
| 8 | DCE | 2 | DIPP (20) | 40 | 2[3] | 35% | 45%[2] | 94 |
| 9 | THF | 8 | DIPP (20) | 40 | 2 | 7% | 65% | >95 |
| 10 | THF | 8 | Mes (20) | 40 | 2 | 4% | 70% | 95 |
| 11 | DCE | 8[4] | DIPP (20) | 40 | 2 | 32% | 39% | >95 |
| 12 | DCE | 8 | DIPP (20)[5] | 40 | 2[3] | 35% | 39% | >95 |
| 13[6] | DCE | 8 | DIPP (15) | 40 | 2 | 52% | 35% | >95 |
| 14[7] | DCE | 5 | DIPP (5) | 30 | 12 | 38% | 52%[2] | >95 |

[1]Exemplary result using Ru-Mes catalyst directly from Sigma without purification. Around 20 conditions were tried using this impure catalyst but they were inconsistent. The remaining entries for this catalyst use the re-purified Ru-Mes catalyst (see "Metathesis Reaction Parameters" in Part 1(c)).

[2]The recovered starting material contained an impurity that was inseparable by chromatography.

[3]Reaction still looked slightly red/purple.

[4]Added 1.0 eq. of methyl 3-butenoate (13) at the beginning and then 1.0 eq. every 15 minutes.

[5]Added 5 mol % Ru-cat at beginning (initial conc. 0.15M of substrate), and then 5 mol % (25 uL, 0.04M in DCE) every 30 min (final conc. 0.1M).

[6]Reaction performed on 16 mg scale (12) in 0.5-2.0 mL Biotage microwave vial (FIG. 6B).

[7]Reaction performed on 100 mg scale (12) in VWR vial (FIG. 6B)) following "Optimized Z-Selective Metathesis General Procedure" (Part 1(c)).

Entries 1-12 were on small scale (5 mg scale 12), entry 13 corresponds to a "medium scale" (16 mg scale 12) reaction using the best condition from entries 1-12, and entry 14 is a "large scale" (100 mg scale 12) using the "Optimized Z-Selective Metathesis General Procedure" outlined in Part 1(c).

Exemplary Procedure: In a $N_2$ filled glovebox, oxaspirolactone 12 (16 mg, 0.063 mmol, 1.0 eq.) was combined with DCE (0.33 mL) and methyl 3-butenoate 13 (54 uL, 0.51 mmol, 8.0 eq.) in a Biotage (0.5-2 mL) microwave vial (FIG. 6B)). To the vial, the Grubbs Z-selective (DIPP; FIG. 6A) catalyst (6.4 mg, 0.0095 mmol, 0.15 eq.) was then added all at once in DCE (0.3 mL) to give a final concentration of 0.1 M (solution looks light purple). As soon as the catalyst was added, the microwave vial (open to the atmosphere of the glovebox, no cap, see FIG. 6B) was placed in a sand bath to 40° C. After stirring at this temperature for 2 hours, the reaction mixture (looks brown) was removed from the glovebox, concentrated, and purified by column (slow gradient, pure hexanes to 3:2 hexanes/EtOAc) to give tricyclic-PGDM methyl ester 3 (10.7 mg, 52%, >95% Z) as a colorless oil.

After extensive investigations, it was determined that about 10-15% (90% Z) of the cross-metathesis product could be obtained with the commercially available Ru—Z-Mes, but the results were not consistent. It was further determined that re-purification of the Ru—Z-Mes was beneficial and increased the yield to 35%. To further enhance the yield and Z selectivity, the Ru—Z-DIPP catalyst was evaluated and determined to be superior to the Ru—Z-Mes catalyst, with final product 3 produced in better yield (52%) and higher selectivity (>95% Z).

Interestingly, while both Ru—Z-Mes and Ru—Z-DIPP are conventionally most efficient in THF, only negligible yields (<10%) were obtained in the present studies, supporting lack of dependency on a particular solvent. The reaction also was conducted at 100-mg scale to provide 38% (>95% Z) yield of compound 3 at a lower catalyst loading (5 mol %) and less amount of 13 (5 equiv.).

The analytical data supported the reported syntheses. Kimbrough et al. (2019), supra; Prakash et al. (1988), supra.

$^1H$ NMR (500 MHz, $CDCl_3$) δ 5.67 (td, J=10.3, 4.9, 1H), 5.59-5.52 (m, 1H), 4.40 (td, J=5.1, 1.5 Hz, 1H), 4.33-4.27 (m, 1H), 3.69 (s, 3H), 3.27 (dd, J=15.9, 8.9 Hz, 1H), 3.03 (dd, J=15.9, 6.1 Hz, 1H), 2.75 (dt, J=17.6, 9.9 Hz, 1H), 2.57-2.51 (m, 1H), 2.47 (ddd, J=17.6, 9.5, 2.7 Hz, 1H), 2.31 (dt, J=14.5, 10.2 Hz, 1H), 2.24-1.57 (m, 11H).

$^{13}C$ NMR (125 MHz, $CDCl_3$) δ 176.6, 173.1, 132.9, 121.6, 108.1, 74.9, 71.9, 52.2, 43.7, 42.2, 39.3, 34.8, 32.9, 28.7, 28.3, 25.0, 18.4. IR (ATR): 3485, 3022, 2930, 1769, 1735, 1650, 1437, 1380, 1330, 1287, 1272, 1242, 1193, 1170, 1120, 1100, 1079, 1035, 1007 $cm^{-1}$.

HRMS (ESI): m/z Calc. for $C_{17}H_{24}O_6Na$ $[M+Na]^+$: 347.1465, found: 347.1464.

Z-Selective Metathesis

Metathesis Reaction Parameters: All solvents (DCE, THF, PhH, pentanes) were freshly distilled over $CaH_2$ (or Nal-benzophenone for THF) and degassed by freeze pump thaw. Deuterated benzene for NMR monitoring was degassed by freeze pump thaw. The Z-selective (DIPP) catalyst was graciously sent by Professor Grubbs, and the Z-selective (Mes) catalyst was purchased from Sigma-Aldrich and repurified as follows: in a $N_2$ filled glovebox, the Z-selective (Mes) catalyst (80 mg) (looks dark brown/black) was combined with 1 mL of pentane, and then filtered through a 1 mL syringe (clogged with a small piece of cotton) filled to the 0.5 mL mark with celite (celite briefly dried in oven before putting in glovebox) and pre-moistened with pentane. The above catalyst solution was then filtered followed by 2 mL of PhH to give a dark purple solution. The resulting filtrate was then concentrated under reduced pressure (in the glovebox) to give a dark purple/black solid (see FIG. 6A for catalyst descriptions).

Methyl 3-butenoate 13 (purchased from Sigma-Aldrich, St. Louis, MO) and all commercial olefins were filtered neat through neutral alumina in the glovebox before use.

Example 13

Z-Selective Metathesis Optimization

Figure 5:
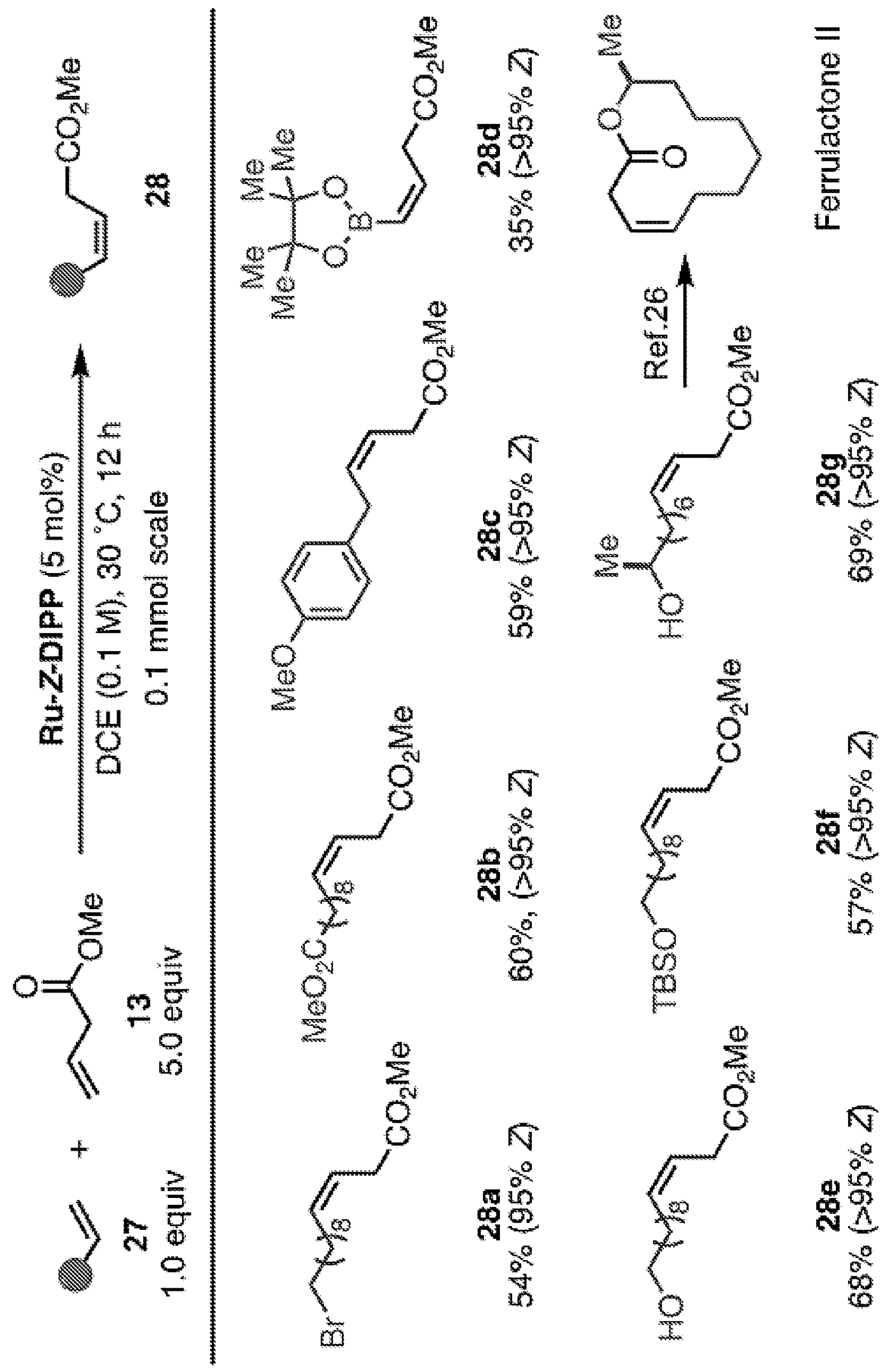
FIG. 5 shows a table of substrates that can be used for Z-selective cross metathesis with compound 13 in a method for the total synthesis of tricyclic-PGDM methyl ester (compound 3).

With the total synthesis of 3 secured, it was next sought to generalize the Z-selective cross metathesis with the challenging β,γ-unsaturated ester substrate 13 (see FIG. 5). Various terminal olefins with a wide range of functional groups were investigated.

Z-selective Metathesis Optimization NMR Studies: In a 0.5-2 mL Biotage microwave vial (see FIG. 6A), 11-Bromo-1-undecene (23.3 mg, 0.1 mmol, 1.0 eq.) was combined with DCE (0.5 mL) and methyl 3-butenoate 13 (54 uL, 0.5 mmol, 5.0 eq.). To the solution, the Grubbs Z-selective (DIPP) catalyst (3.4 mg, 0.005 mmol, 0.05 eq.) in 0.5 mL DCE was then added all at once to give a final concentration of 0.1 M (solution looks light purple). The mixture (reaction ran open to the atmosphere of the glovebox (no cap); see FIG. 6B) was then heated to 30° C. and monitored by H-NMR (Note 1) to track the quantity of the ruthenium catalyst remaining. To track the Z/E ratio, each NMR sample was immediately concentrated under reduced pressure and reanalyzed in $C_6D_6$.

Note 1: For sampling, 200 uL of the reaction mixture was combined with 400 uL of $C_6D_6$ containing anthracene as an internal standard (combined in NMR tube in glovebox and sealed cap with parafilm) and immediately analyzed. After each addition, a line was marked on the side of the microwave vial and DCE was intermittently added to account for evaporation.

Scheme 16 Ru-Z-DIPP Catalyst

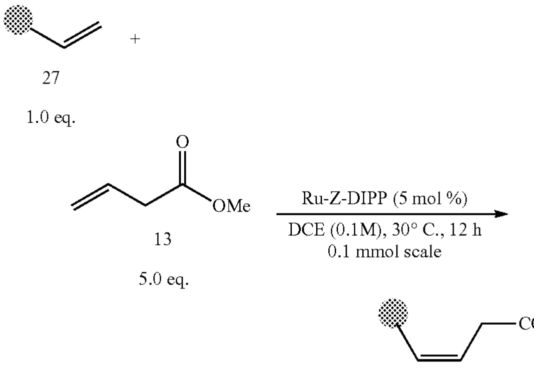

27, 1.0 eq.; 13, 5.0 eq.; 28

Optimized Z-Selective Metathesis General Procedure: In a 0.5-2 mL Biotage microwave vial (see FIG. 6B), the olefin substrate 27 (0.1 mmol, 1.0 eq.) was combined with DCE (0.5 mL) and methyl 3-butenoate 13 (53 uL, 0.5 mmol, 5.0 eq.). The Grubbs Z-selective DIPP catalyst (3.4 mg, 0.005 mmol, 0.05 eq.) was then combined with DCE (0.5 mL) and added all at once to the microwave vial (solution looks light purple). The reaction mixture (open to atmosphere of the glovebox (no cap); see FIG. 6B) was left to stir at 30° C. for 12 hour (for all substrates reaction looked brown after this time), and was then removed from the glovebox, concentrated under reduced pressure, and purified by flash chromatography to give the metathesis products 28.

Metathesis Experimental Data

28a

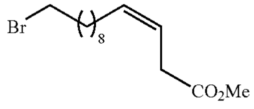

54% (95% Z)

Compound 28a: 11-Bromo-1-undecene and methyl 3-butenoate were reacted following the general procedure. Flash chromatography (pure hexanes to 3% EtOAc) gave product 28a (16.6 mg, 54% yield, 95% Z) as a colorless oil.

$^1H$ NMR (500 MHz, $C_6D_6$) δ 5.71-5.65 (dtt, J=10.5, 7.2, 1.6 Hz, 1H), 5.51-5.44 (dtt, J=10.9, 7.3, 1.8 Hz, 1H), 3.29 (s, 3H), 2.96-2.91 (m, 4H), 1.89 (q, J=7.4 Hz, 2H), 1.48 (m, 2H), 1.26-1.18 (m, 2H), 1.17-0.98 (m, 10H).

$^{13}C$ NMR (125 MHz, $C_6D_6$) δ 171.2, 132.9, 121.4, 50.9, 33.4, 32.7, 32.6, 29.4, 29.3, 29.2, 29.1, 28.7, 28.0, 27.3.

IR (ATR): 3021, 2925, 2854, 1740, 1458, 1435, 1402, 1329, 1287, 1251, 1194 $cm^{-1}$.

HRMS (ESI): m/z Calc. for $C_{14}H_{26}BrO_2$ $[M+H]^+$: 305.1111/305.1093, found: 305.1111/305.1091.

28b

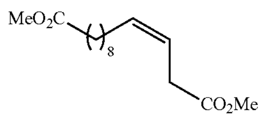

60%, (>95% Z)

Compound 28b: Methyl 10-undecenoate and methyl 3-butenoate were reacted following the general procedure. Flash chromatography (pure hexanes to 3% EtOAc) gave product 28b (16.3 mg, 60%, >95% Z) as a colorless oil.

$^1H$ NMR (500 MHz, $C_6D_6$) δ 5.66 (dtt, J=10.5, 7.2, 1.6 Hz, 1H), 5.45 (dtt, J=10.9, 7.4, 1.8 Hz, 1H), 3.34 (s, 3H), 3.29 (s, 3H), 2.92 (dd, J=7.3, 1.8 Hz, 2H), 2.08 (t, J=7.4 Hz, 2H), 1.86 (q, J=7.0 Hz, 2H), 1.55-1.47 (m, 2H), 1.35-1.07 (m, 10H).

$^{13}C$ NMR (125 MHz, $C_6D_6$) δ 173.0, 171.2, 132.9, 121.3, 50.9, 50.6, 33.8, 32.6, 29.3, 29.2, 29.1, 29.0, 27.3, 24.9.

IR (ATR): 3023, 2926, 2854, 1737, 1457, 1436, 1401, 1363, 1329, 1252, 1194 $cm^{-1}$.

HRMS (ESI): m/z Calc. for $C_{13}H_{27}O_3[M+H]^+$: 271.1904, found: 271.1904.

28c

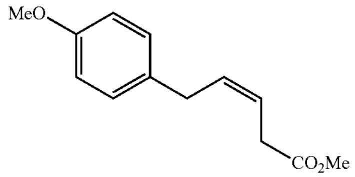

59% (>95% Z)

Compound 28c: 4-Allylanisole and methyl 3-butenoate were reacted following the general procedure. Flash chromatography (pure hexanes to 1% EtOAc) gave product 28c (13.0 mg, 59% yield, >95% Z) as a colorless oil.

$^1H$ NMR (500 MHz, $C_6D_6$) δ 6.94 (d, J=8.6 Hz, 2H), 6.74 (d, J=8.6 Hz, 2H), 5.74-5.65 (dtt, J=10.7, 7.1, 1.5 Hz, 1H), 5.64-5.57 (dtt, J=10.6, 7.4, 1.5 Hz, 1H), 3.29 (m, 6H), 3.11 (dd, J=7.3, 1.6 Hz, 2H), 2.92 (dd, J=7.1, 1.7 Hz, 2H).

$^{13}C$ NMR (125 MHz, $C_6D_6$) δ 171.1, 158.4, 132.0, 131.8, 129.3, 121.7, 114.0, 54.4, 51.0, 32.6, 32.5.

IR (ATR): 3029, 2998, 2951, 2926, 2853, 2041, 1736, 1611, 1584, 1510, 1464, 1436, 1398, 1330, 1301, 1243, 1194 $cm^{-1}$.

HRMS (ESI): m/z Calc. for $C_{13}H_{17}O_3[M+H]^+$: 221.1172, found: 221.1172.

28d

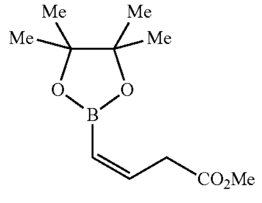

35% (>95% Z)

Compound 28d: Vinylboronic acid pinacol ester and methyl 3-butenoate were reacted following the general procedure. Flash chromatography (pure hexanes to 15% EtOAc) gave product 28d (8.5 mg, 35% yield, >95% Z) as a colorless oil.

$^1H$ NMR (500 MHz, $CDCl_3$) δ 6.57 (dt, J=13.7, 7.0 Hz, 1H), 5.55 (dt, 13.5, 1.7 Hz, 1H), 3.69 (s, 3H), 3.53 (dd, J=7.1, 1.7 Hz, 2H), 1.26 (s, 12H).

$^{13}C$ NMR (125 MHz, $CDCl_3$) δ 172.4, 144.9, 83.2, 51.8, 37.1, 24.9.

IR (ATR): 2979, 2953, 2928, 2855, 1740, 1634, 1436, 1424, 1391, 1380, 1372, 1321, 1283, 1263, 1214, 1198 $cm^{-1}$.

HRMS (ESI): m/z Calc. for $C_{11}H_{20}BO_4$ $[M+H]^+$: 227.1452, found: 227.1451.

28e

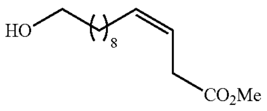

68% (>95% Z)

Compound 28e: 10-Undecen-1-ol and methyl 3-butenoate were reacted following the general procedure. Flash chromatography (pure hexanes to 15% EtOAc) gave product 28e (16.5 mg, 68% yield, >95% Z) as a colorless oil.

$^1H$ NMR (500 MHz, $C_6D_6$) δ 5.70-5.62 (dtt, J=10.5, 7.2, 1.6 Hz, 1H), 5.51-5.42 (dtt, J=10.8, 7.3, 1.7 Hz, 1H), 3.37 (t, J=6.5 Hz, 2H), 3.29 (s, 3H), 2.92 (dd, J=7.3, 1.9 Hz, 2H), 1.89 (q, J=7.2 Hz, 2H), 1.38 (m, 2H), 1.26-1.12 (m, 13H).

$^{13}C$ NMR (125 MHz, $C_6D_6$) δ 171.3, 133.0, 121.3, 62.4, 50.9, 32.9, 32.6, 29.6, 29.5, 29.3, 29.2, 27.3, 25.8.

IR (ATR): 3363, 3024, 2924, 2853, 1741, 1462, 1436, 1400, 1329, 1294, 1256, 1195 $cm^{-1}$.

HRMS (ESI): m/z Calc. for $C_{14}H_{27}O_3[M+H]^+$: 243.1957, found: 243.1955.

28f

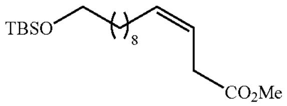

57% (>95% Z)

Compound 28f: TBS protected 10-Undecen-1-ol[10] and methyl 3-butenoate were reacted following the general procedure. Flash chromatography (pure hexanes to 1% EtOAc) gave product 28f (20.4 mg, 57% yield, >95% Z) as a colorless oil.

$^1H$ NMR (500 MHz, $C_6D_6$) δ 5.70-5.63 (dtt, J=10.6, 7.2, 1.6 Hz, 1H), 5.50-5.42 (dtt, J=10.8, 7.3, 1.8 Hz, 1H), 3.55 (t, J=6.4 Hz, 2H), 3.29 (s, 3H), 2.92 (dd, J=7.2, 1.8 Hz, 2H), 1.88 (q, J=7.0 Hz, 2H), 1.51 (m, 2H), 1.37-1.30 (m, 2H), 1.26-1.14 (m, 10H), 0.96 (s, 9H), 0.05 (s, 6H).

$^{13}$C-NMR (125 MHz, $C_6D_6$) δ 171.2, 132.9, 121.3, 63.0, 50.9, 33.0, 32.6, 29.7, 29.5, 29.4, 29.3, 29.2, 27.3, 26.0, 25.8, 18.2, −5.5.

IR (ATR): 3024, 2927, 2855, 1744, 1463, 1435, 1402, 1387, 1361, 1328, 1253, 1193 $cm^{-1}$.

HRMS (ESI): m/z Calc. for $C_{20}H_{41}O_3Si$ $[M+H]^+$: 357.2819, found: 357.2820.

28g

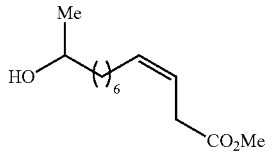

69% (>95% Z)

Compound 28g: Dec-9-en-2-ol[11] and methyl 3-butenoate were reacted following the general procedure. Flash chromatography (pure hexanes to 10% EtOAc) gave product 28g (15.8 mg, 69%, >95% Z) as a colorless oil.

$^1$H NMR (500 MHz, $C_6D_6$) δ 5.65 (dtt, J=10.5, 7.2, 1.6 Hz, 1H), 5.46 (dtt, J=10.8, 7.4, 1.7 Hz, 1H), 3.55-3.48 (m, 1H), 3.29 (s, 3H), 2.92 (dd, J=7.2, 1.9 Hz, 2H), 1.87 (q, J=7.2 Hz, 2H), 1.34-1.12 (m, 11H), 0.99 (d, J=6.2 Hz, 3H).

$^{13}$C NMR (125 MHz, $C_6D_6$) δ 171.3, 133.0, 121.3, 67.3, 50.9, 39.4, 32.6, 29.5, 29.2, 29.1, 27.3, 25.7, 23.5.

IR (ATR): 3397, 3024, 2925, 2854, 1740, 1657, 1457, 1436, 1328, 1257, 1195 $cm^{-1}$.

HRMS (ESI): m/z Calc. for $C_{13}H_{24}O_3Na$ $[M+Na]^+$: 251.1620, found: 251.1618.

Under the aforementioned conditions (15 mol % Ru—Z-DIPP, 8 equiv of 13, 40° C.), although cross metathesis products were obtained in good yield, the ZIE selectivity dropped slightly (90%-92% Z). Gratifyingly, lower the catalyst loadings (5 mol % Ru—Z-DIPP) and temperature (30° C.) gave satisfactory yields and excellent Z selectivity (>95%) for a range of olefin substrates. Notably, free alcohol, TBS ether, alkyl bromide, ester, and boronate were all tolerated and cross metathesis product 28g is a known precursor for synthesis of the beetle pheromone Ferrulactone II. Mori & Tomioka, Pheromone synthesis, CXL. Synthesis of four macrolide pheromones to define the scope and limitation of enzymatic macrolactonization, Chemistry Europe 12: 1011-1017 (1992); Pawar et al., Chemoenzymatic synthesis of ferrulactone II and (2E)-9-hydroxydecenoic acid, Tetrahedron Asymmetry 6(9): 2219-2226 (1995).

Example 14

X-Ray Structure and Analysis Data

With the total synthesis of 3 secured, it was next sought to generalize the Z-selective cross metathesis with the challenging β,γ-unsaturated ester substrate 13 (see FIG. 5). Various terminal olefins with a wide range of functional groups were investigated.

Solid Structure of compound 15: Vapor diffusion crystallization (DCE/hexanes: dissolved compound 15 in DCE in inner chamber and placed hexanes in outer chamber) afforded small white crystals of 15 for X-ray diffraction. The data were collected at 150 K on a Bruker AXS D8 Quest CMOS diffractometer with Mo sealed tube and curved triumph monochromator with a 10 cm×10 cm Photon-100 detector and fixed chi angle. The supplementary crystallographic data was deposited in The Cambridge Crystallographic Data Centre (CCDC 2089935). X-ray analysis data of 15 (FIG. 7).

Figure 8:
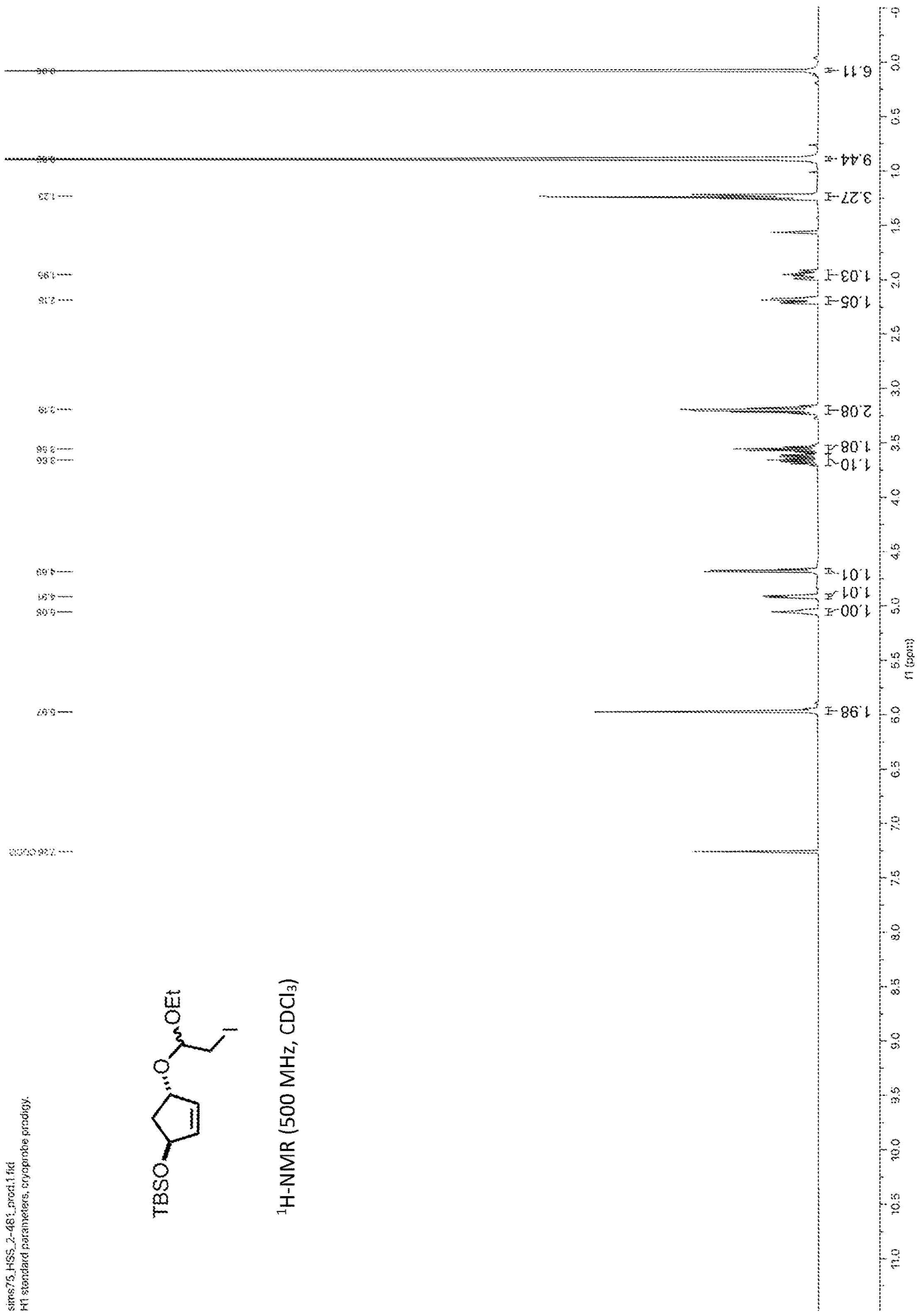
FIG. 8 shows $^1H$ and $^{13}C$ NMR spectra data for the synthesized compounds.
Figure 8:
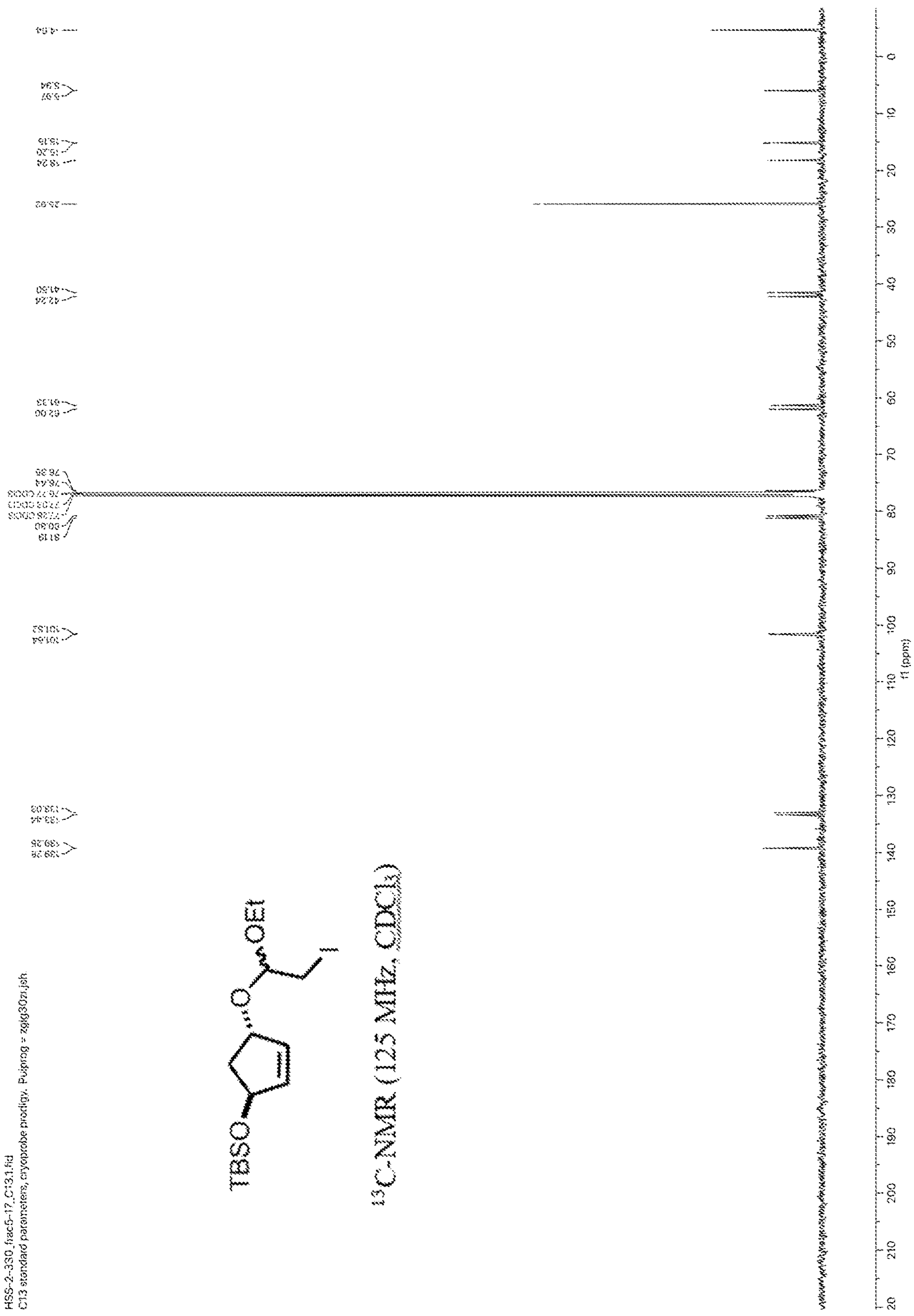
Figure 8:
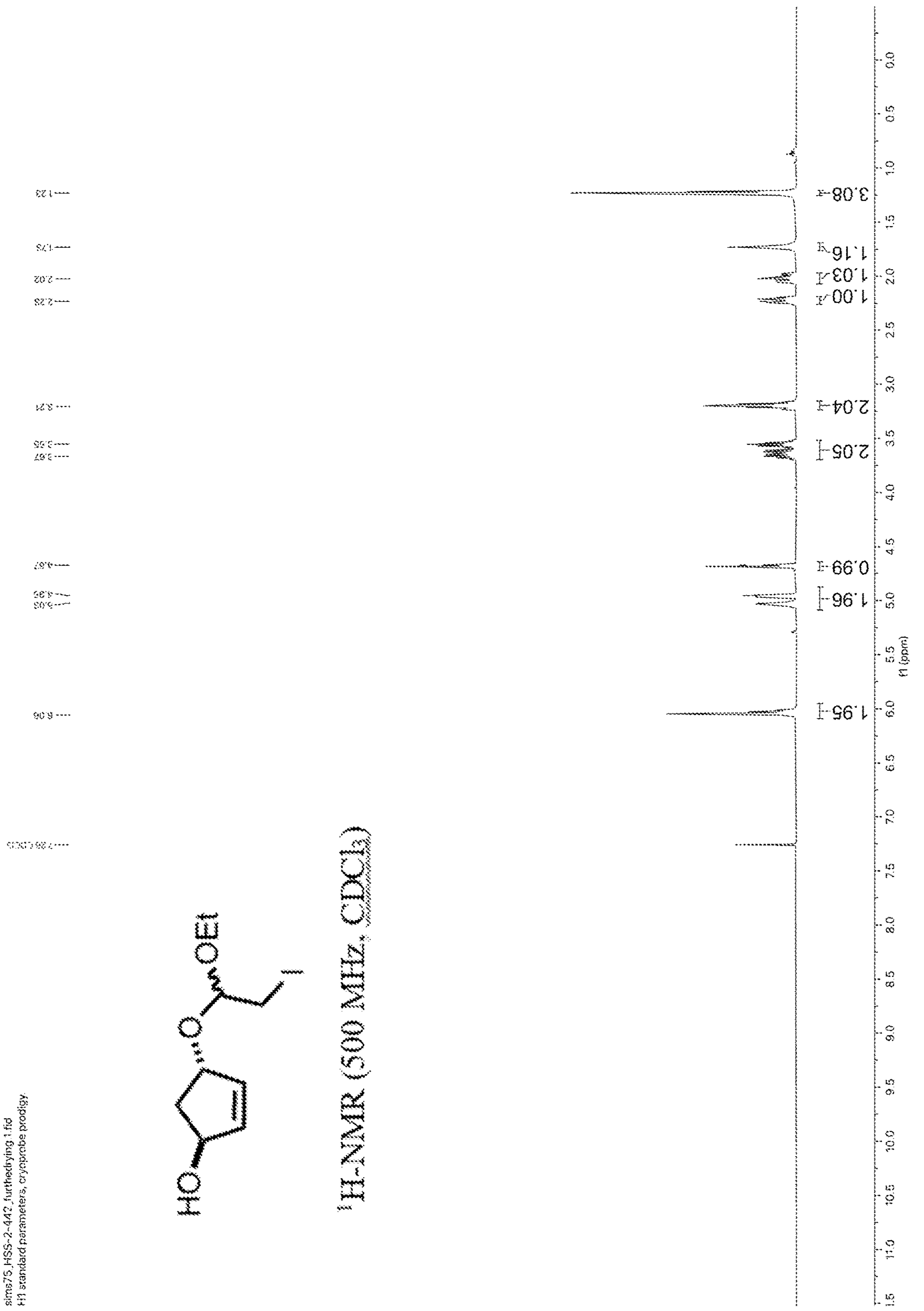
Figure 8:
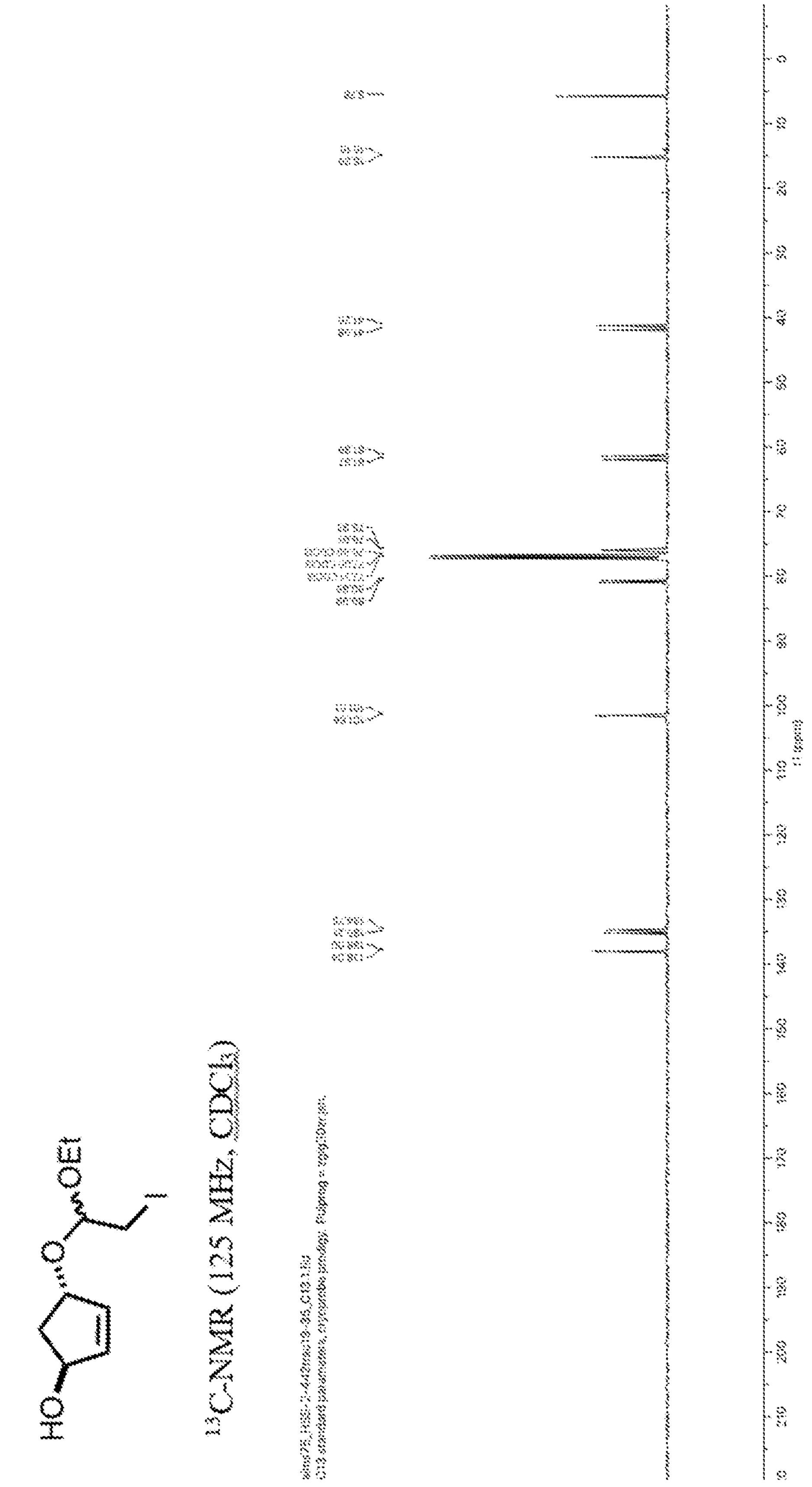
Figure 8:
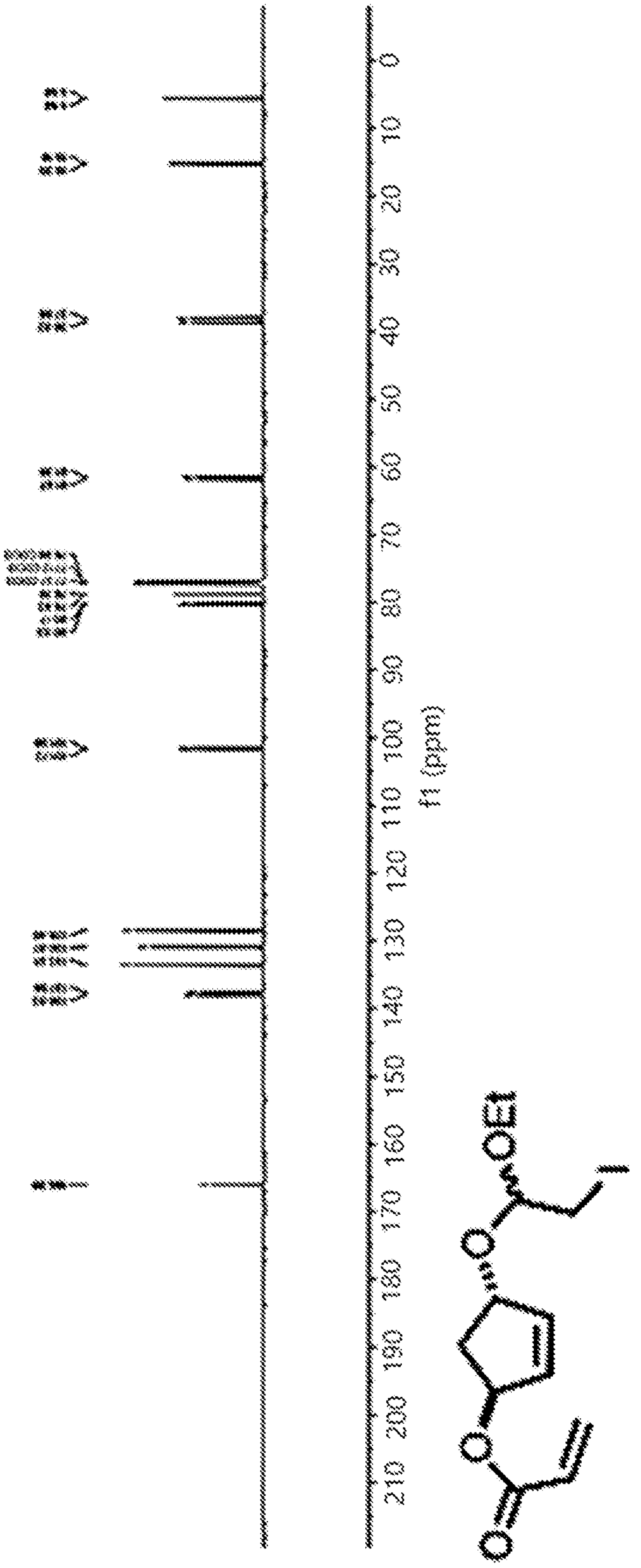
Figure 8:
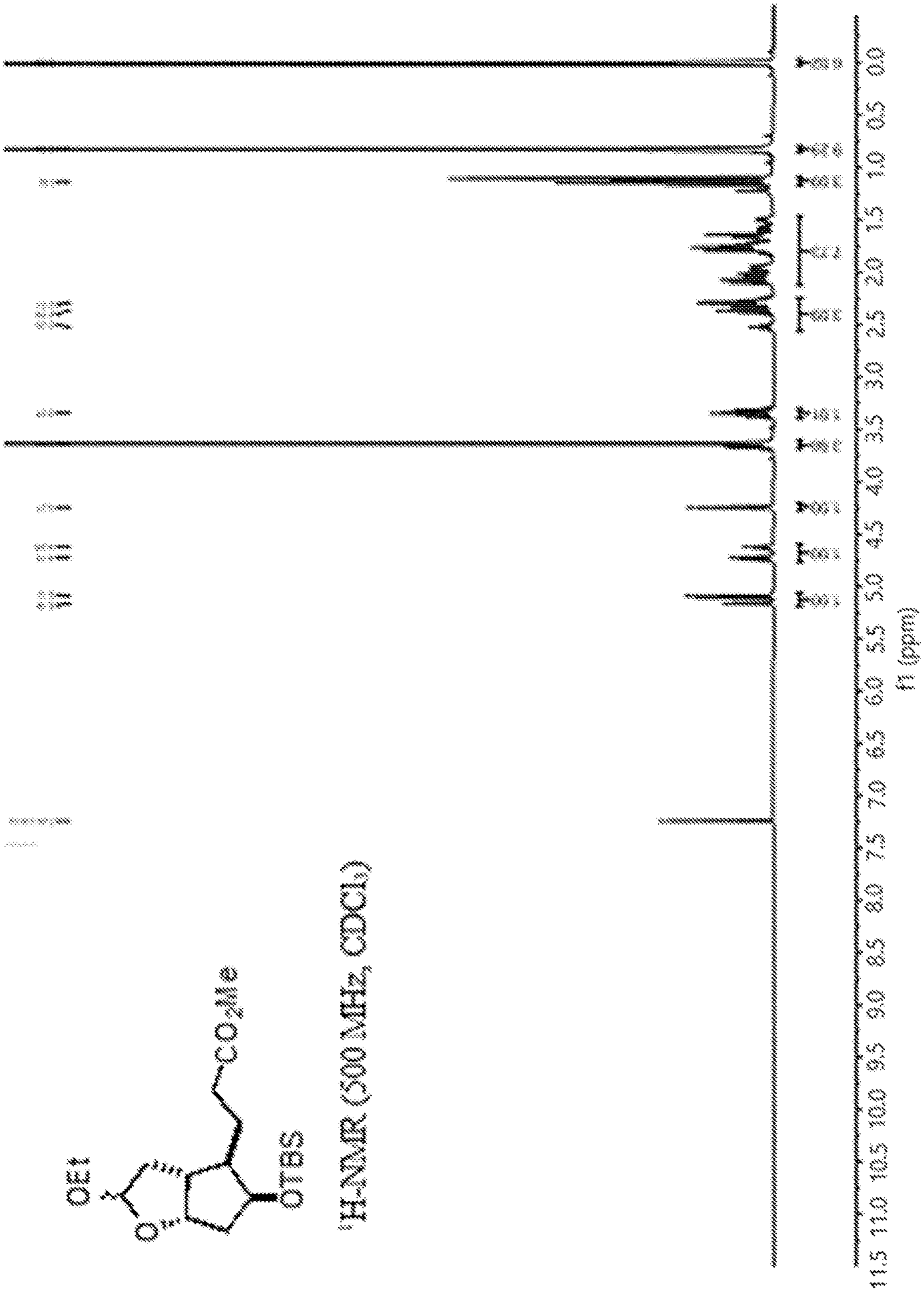
Figure 8:
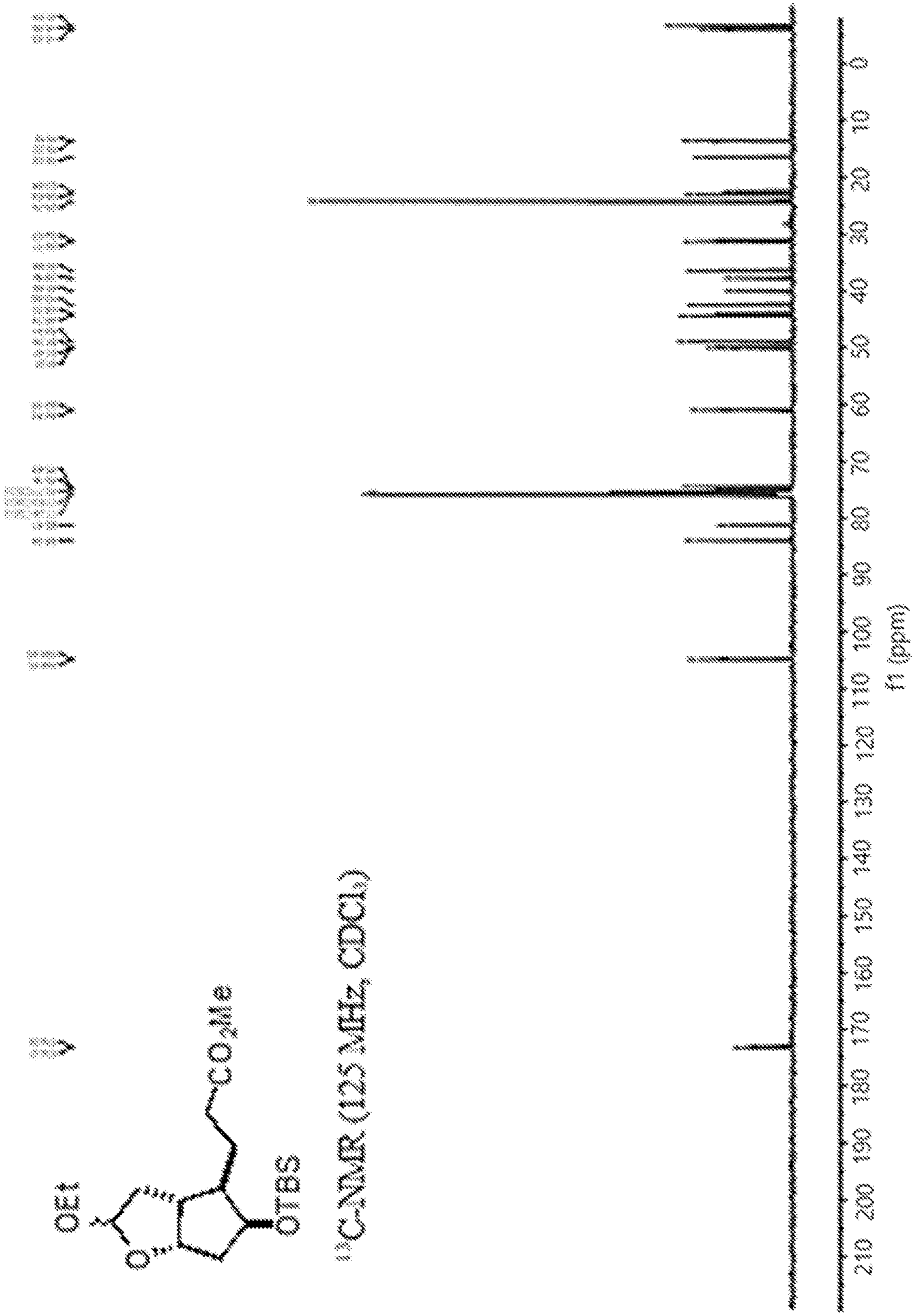
Figure 8:
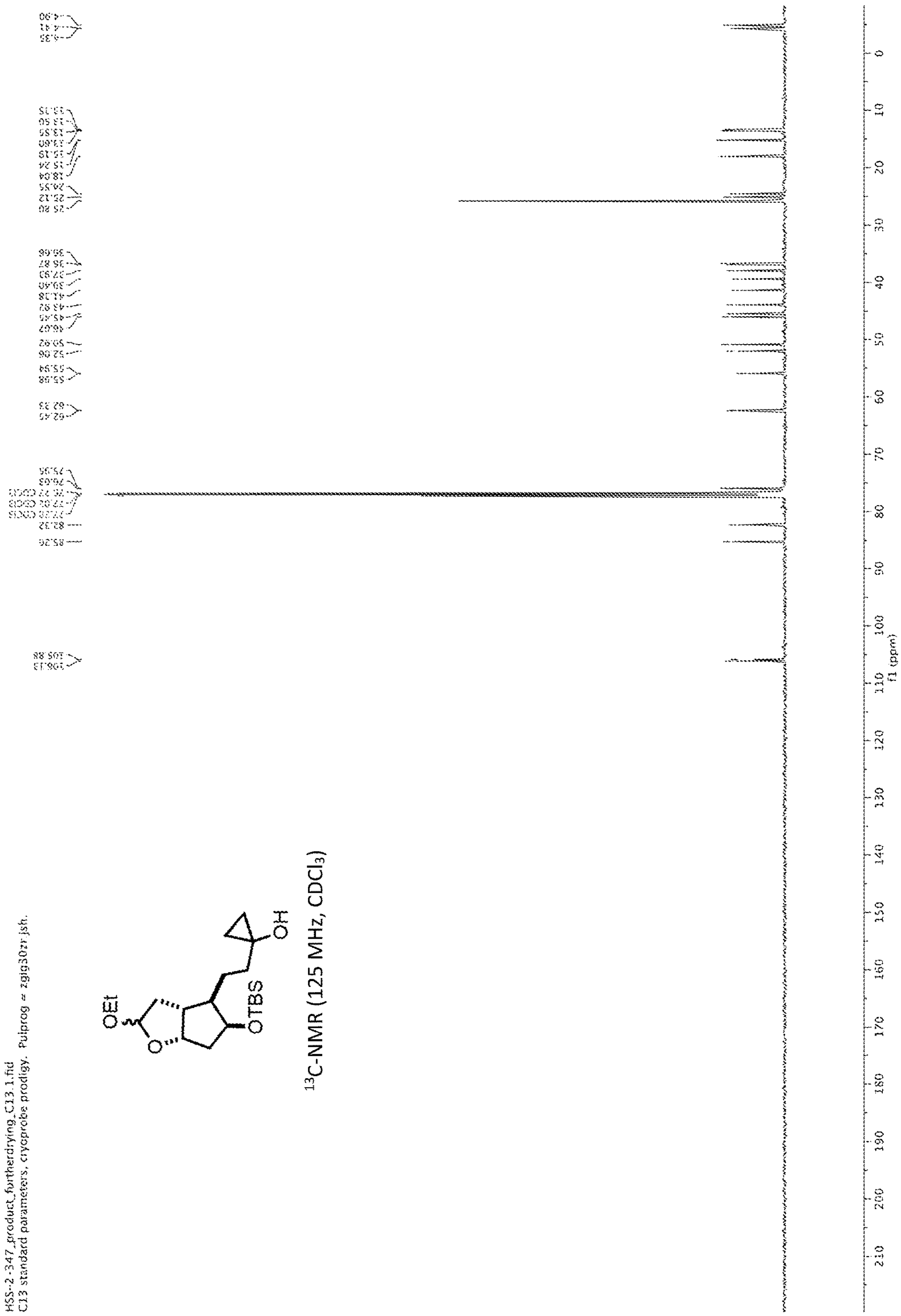
Figure 8:
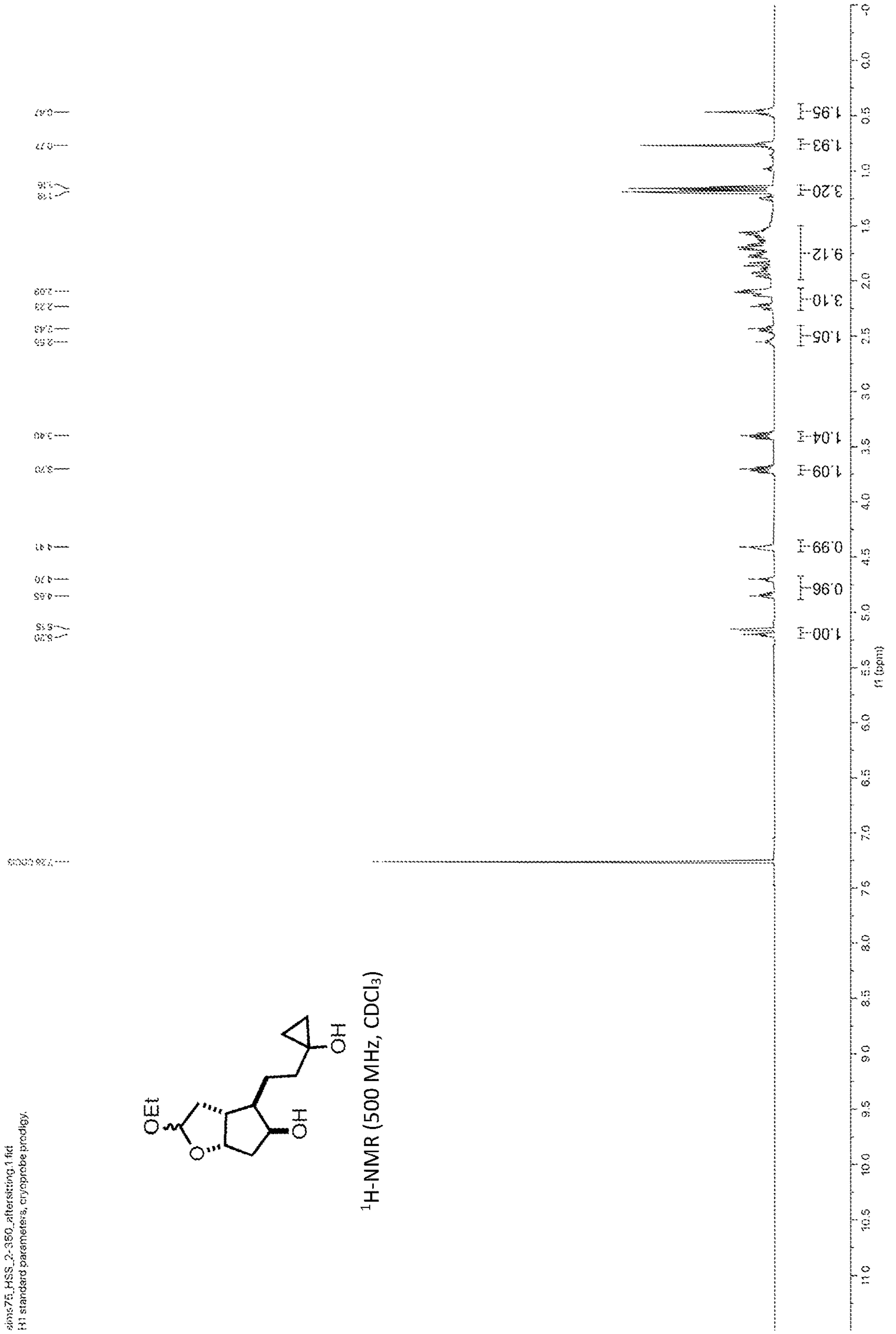
Figure 8:
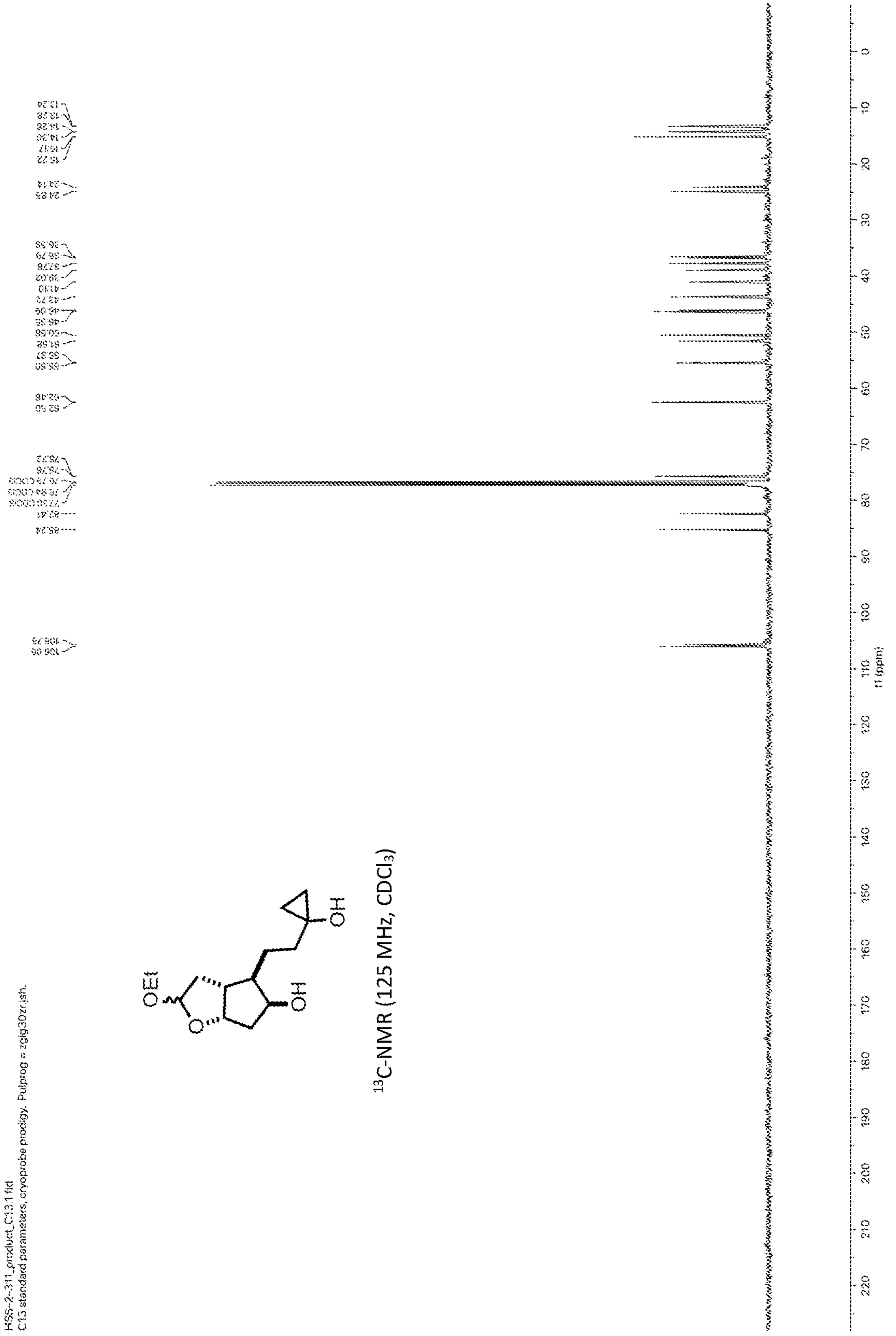
Figure 8:
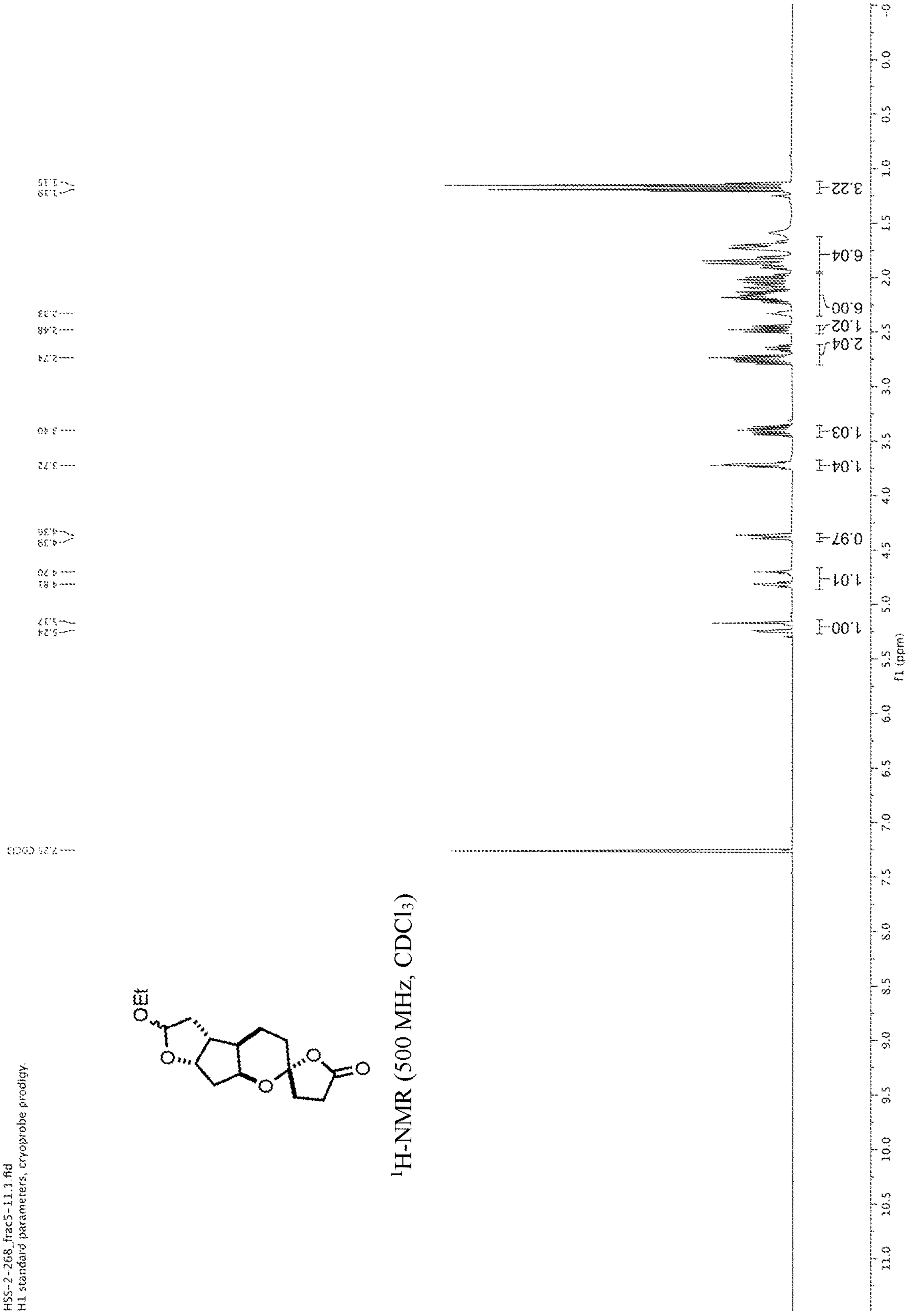
Figure 8:
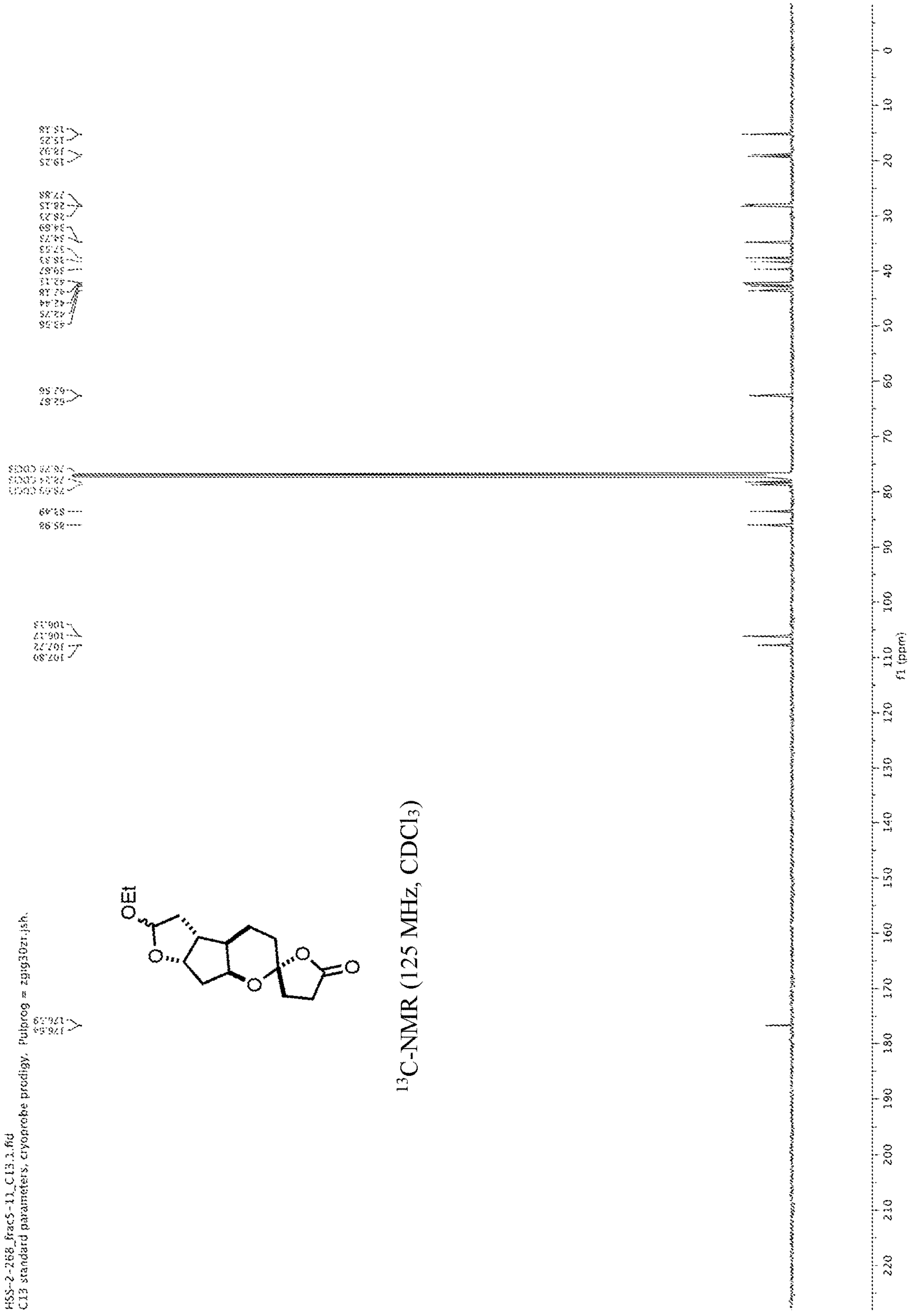
Figure 8:
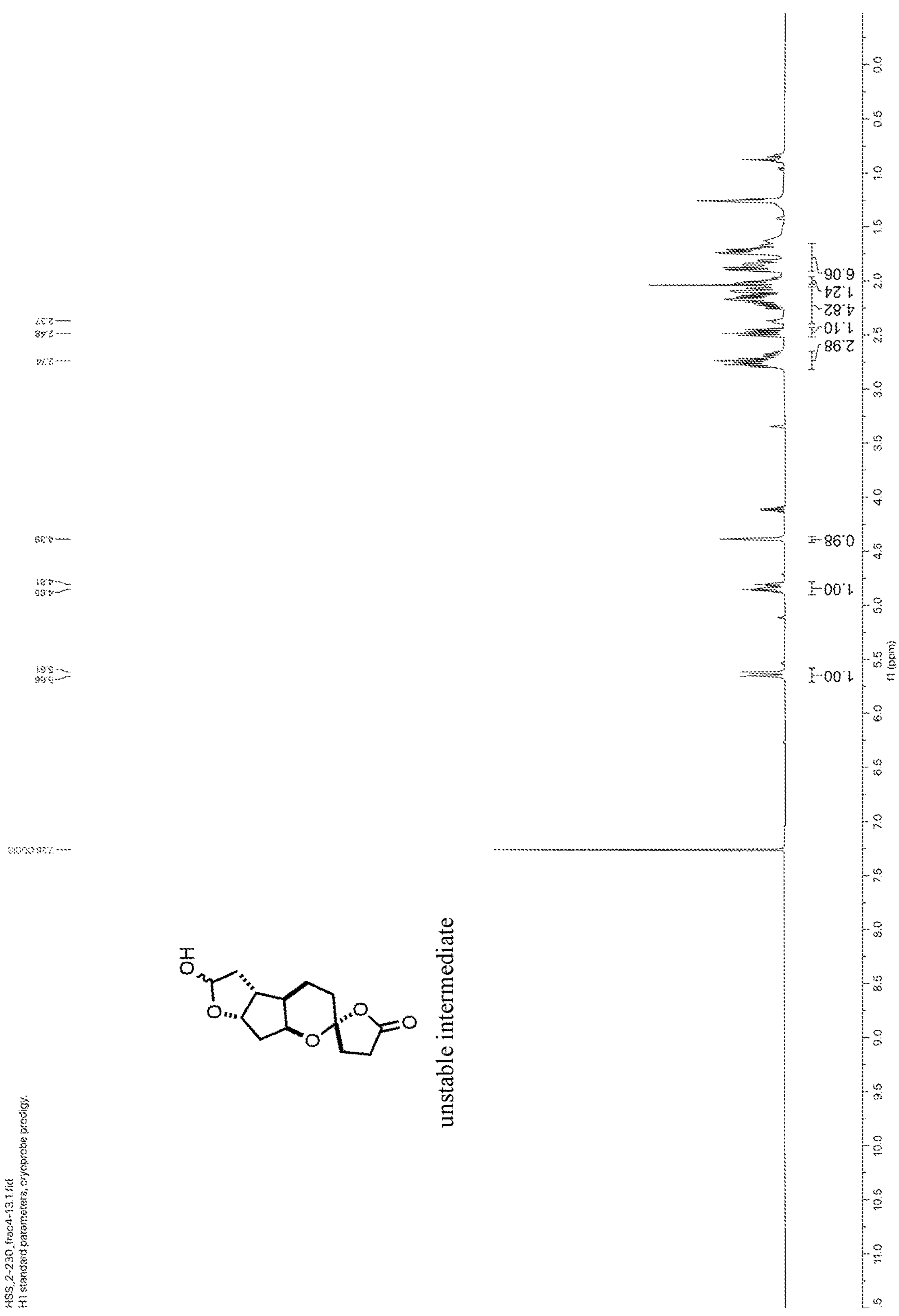
Figure 8:
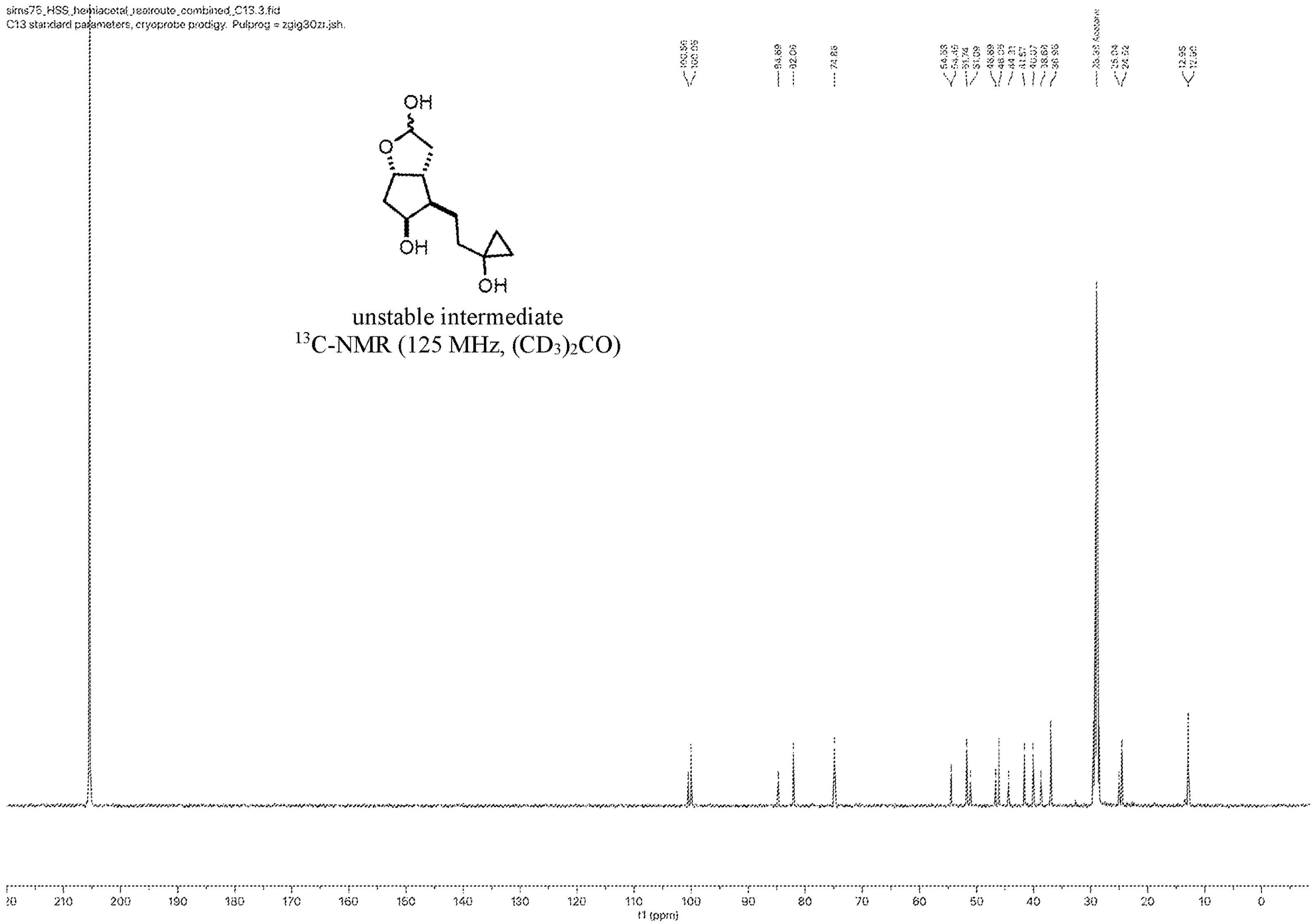
Figure 8:
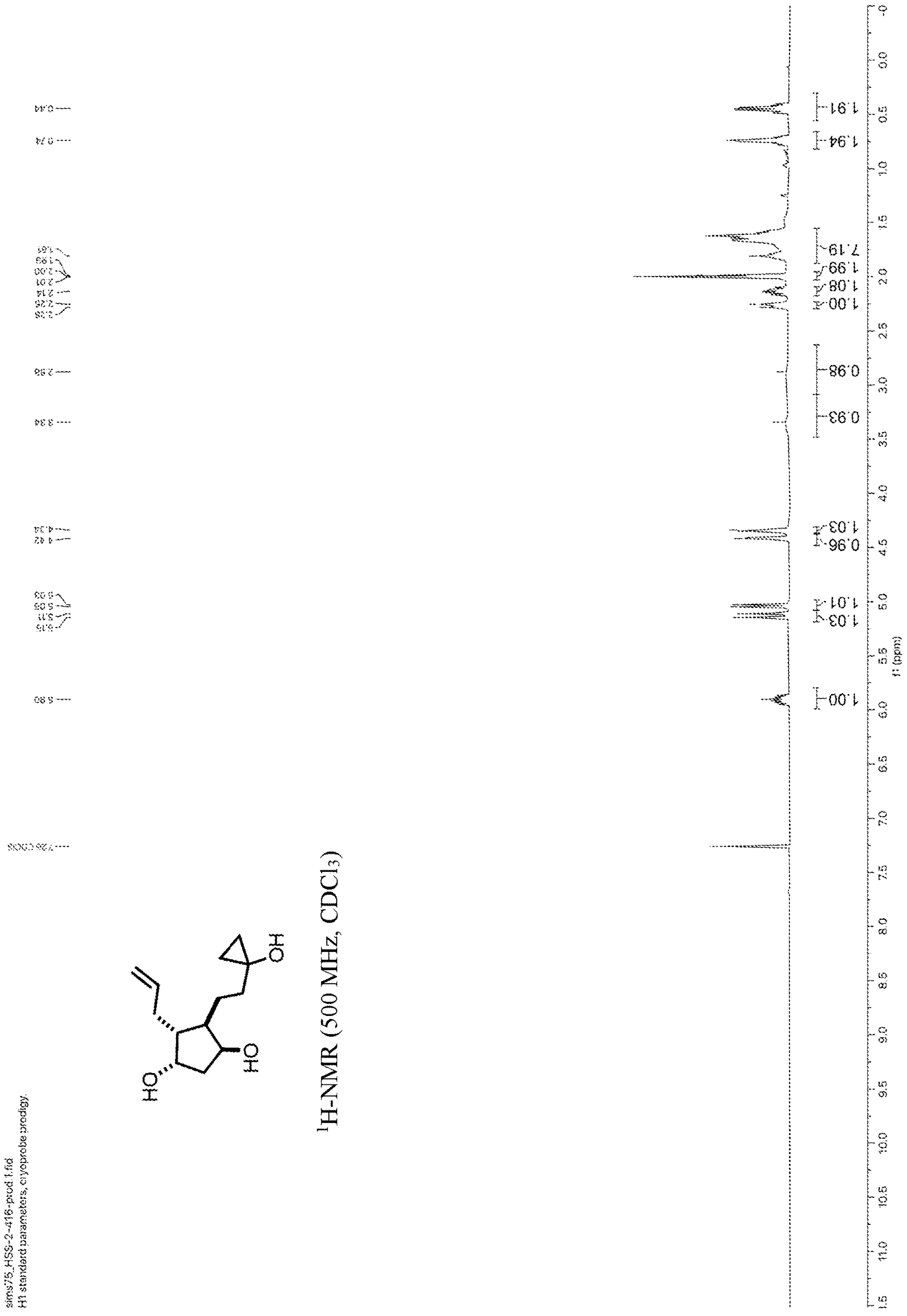
Figure 8:
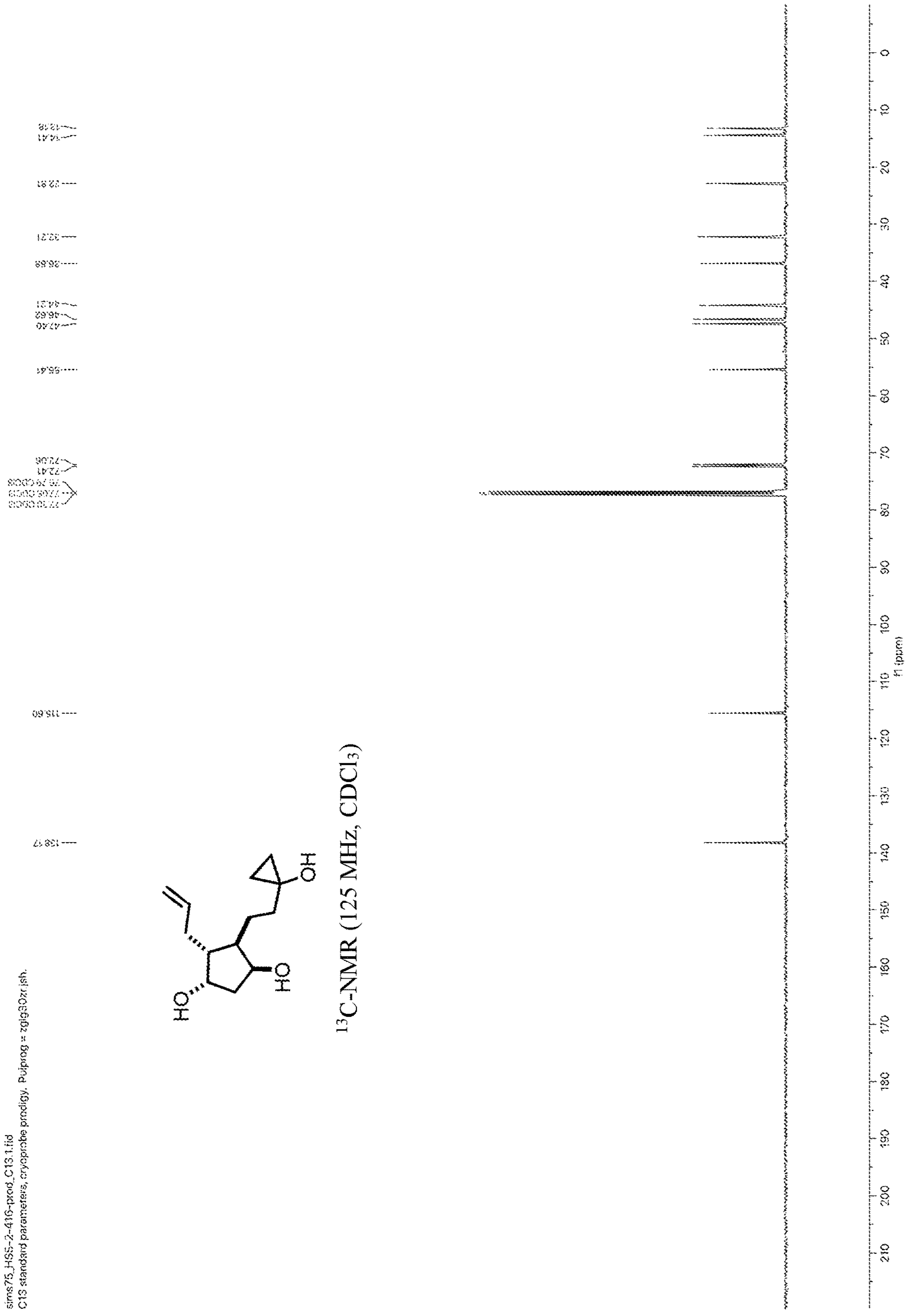
Figure 8:
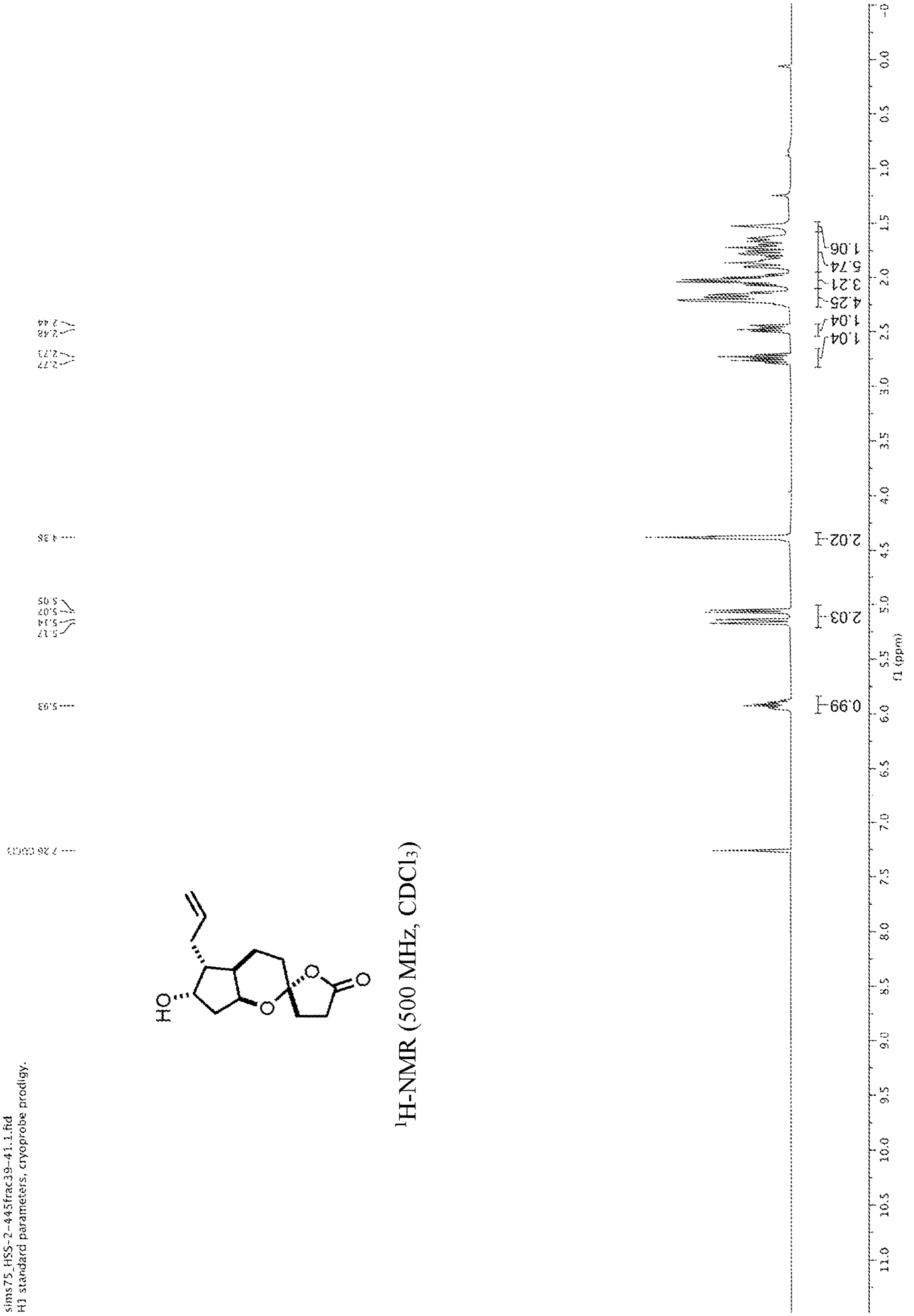
Figure 8:
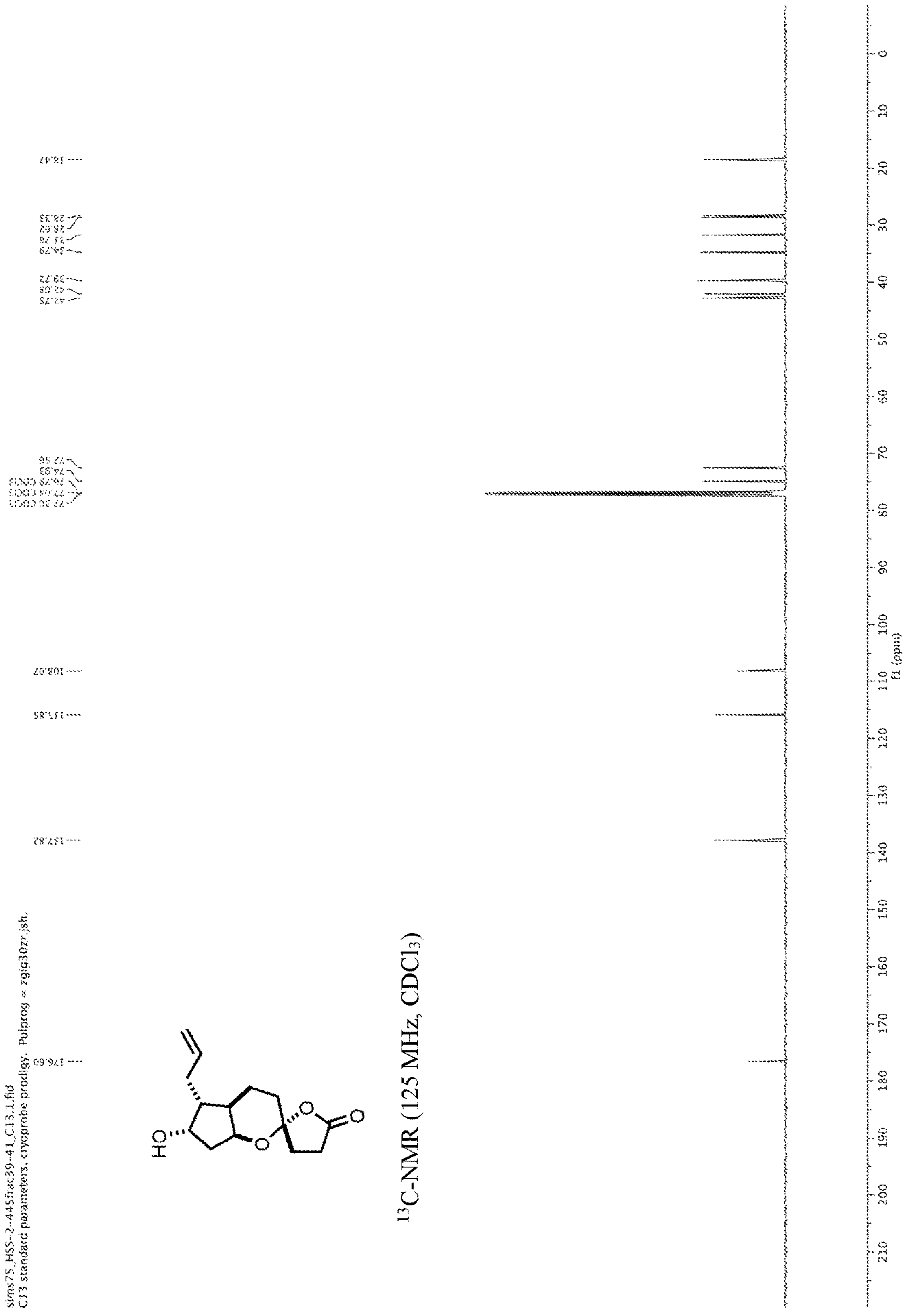
Figure 8:
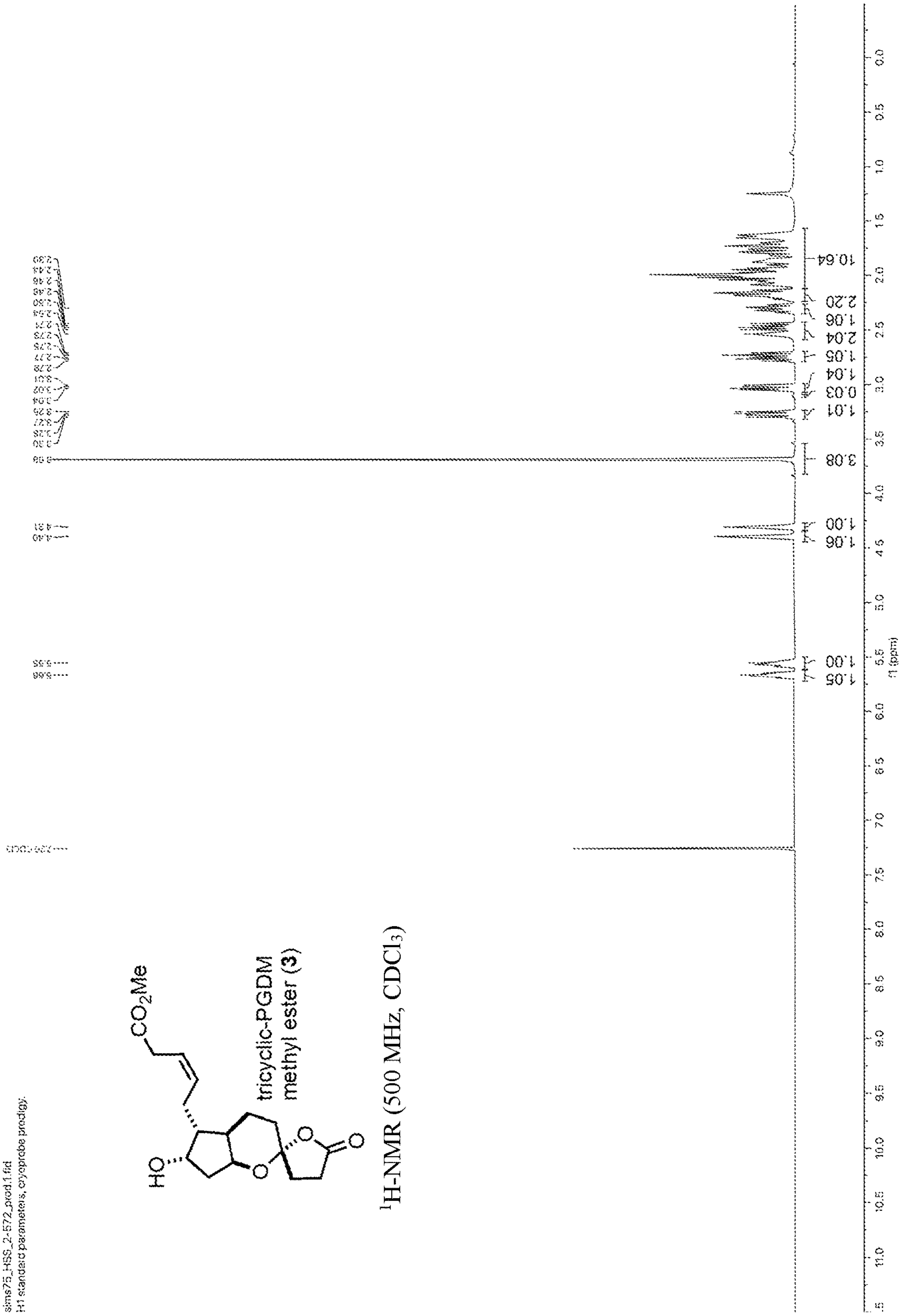
Figure 8:
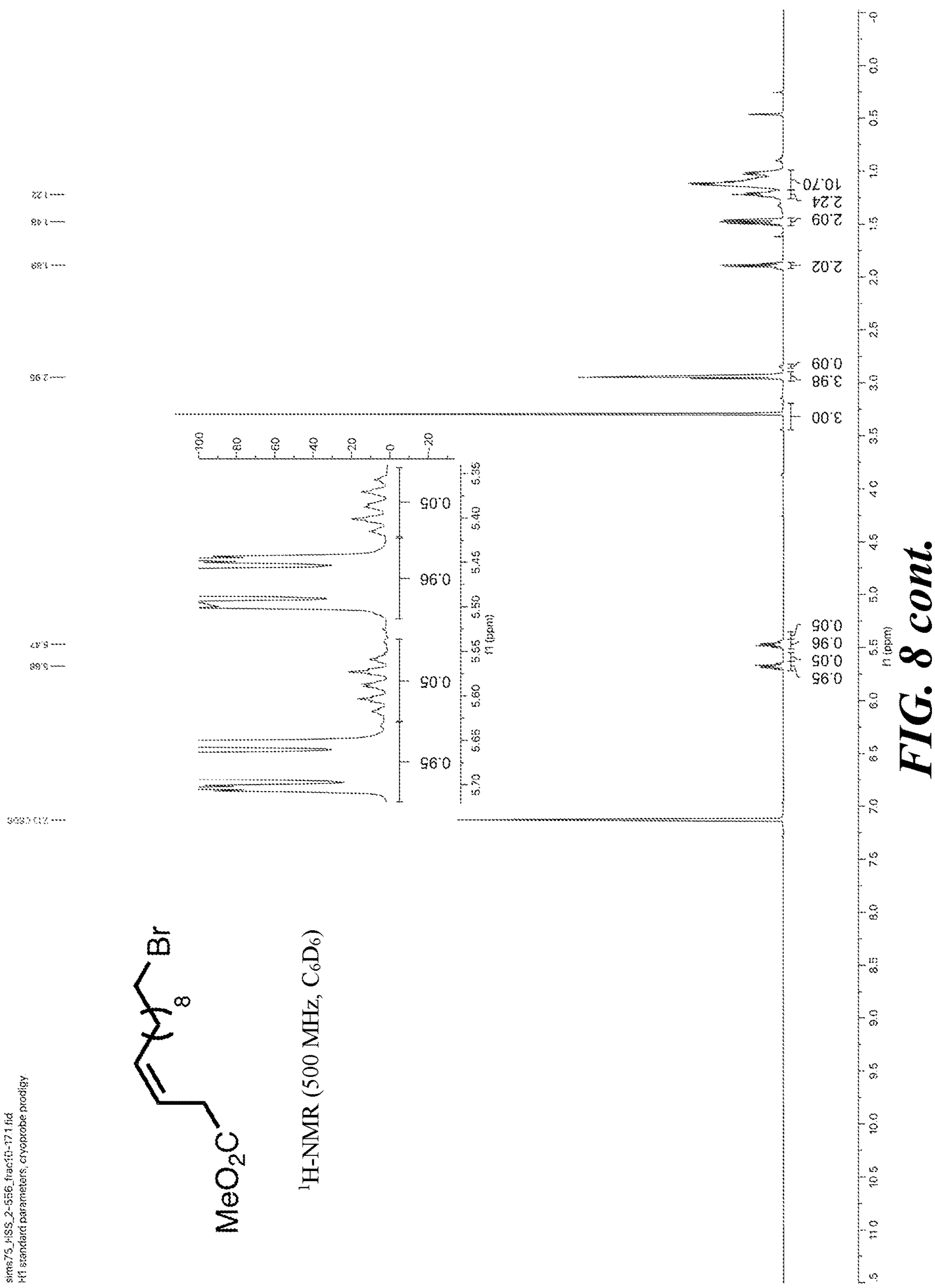
Figure 8:
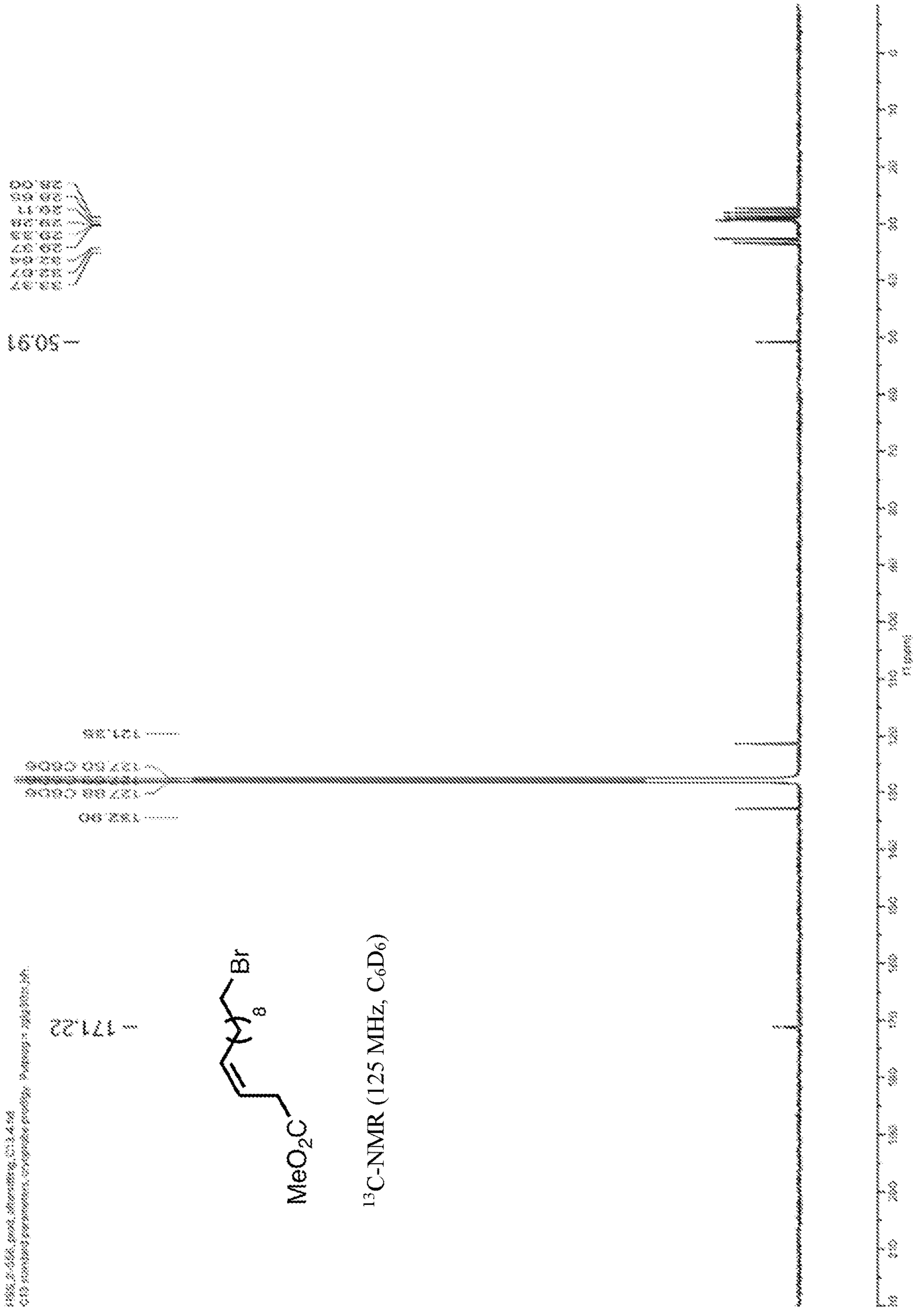
Figure 8:
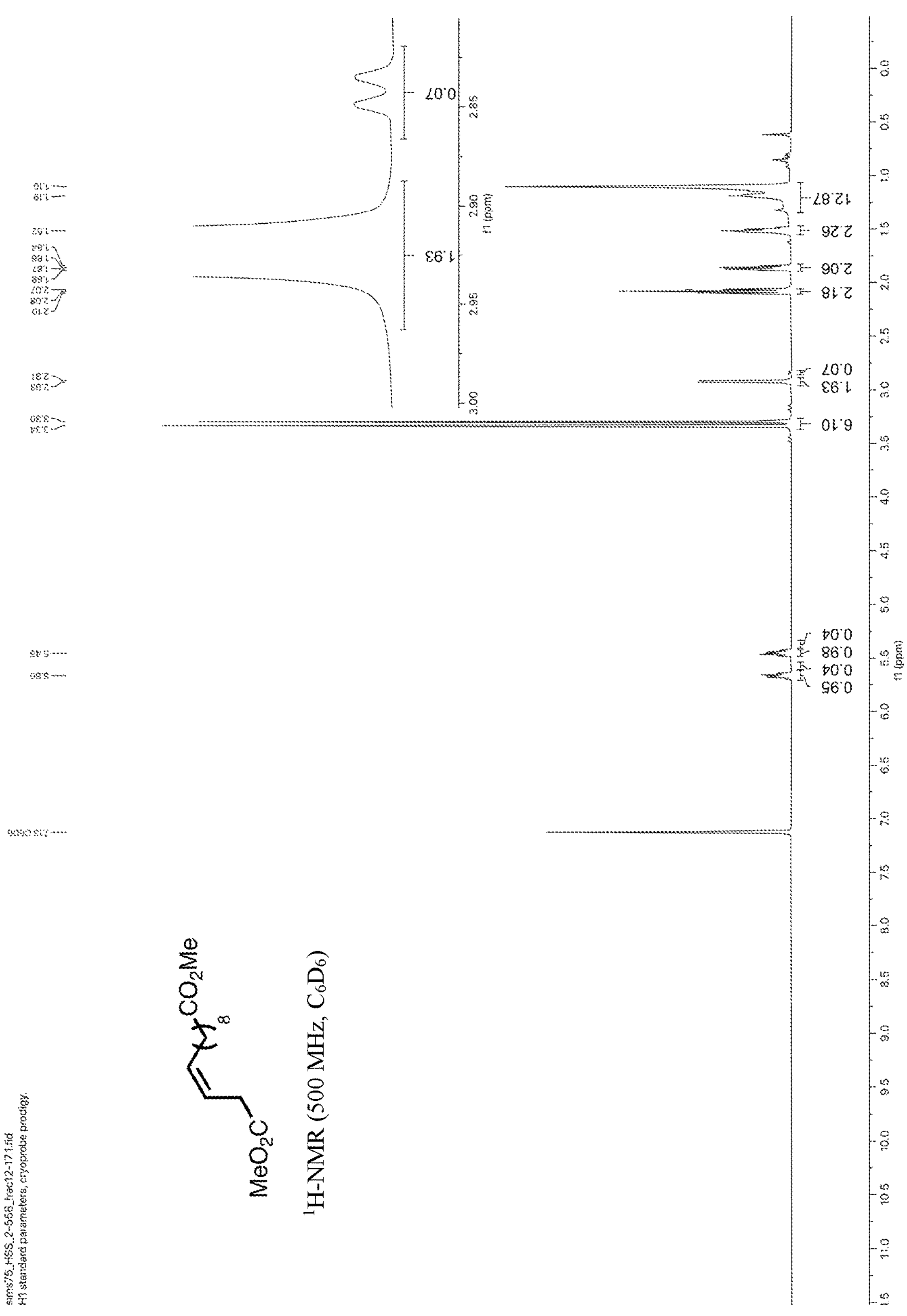
Figure 8:
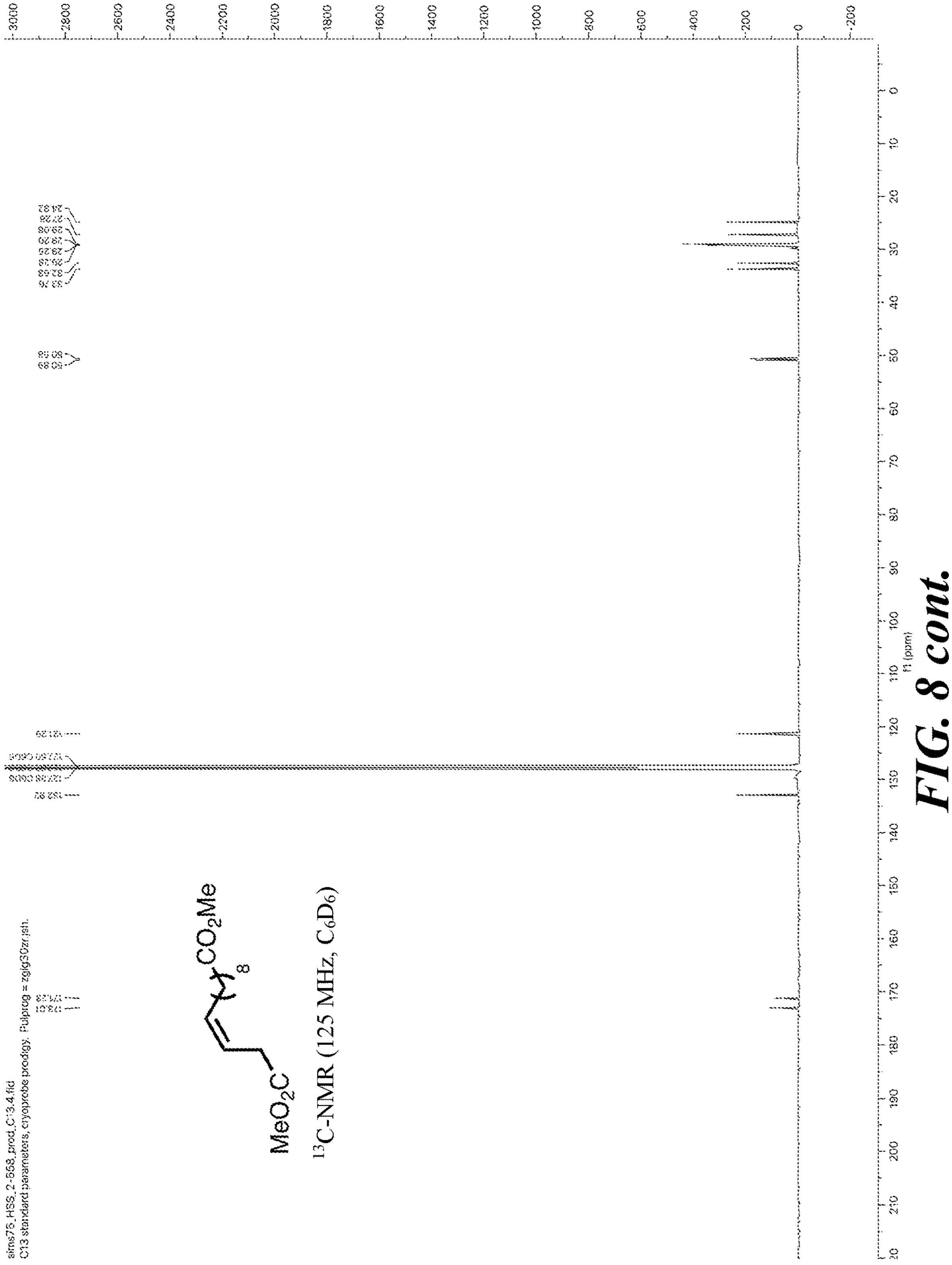
Figure 8:
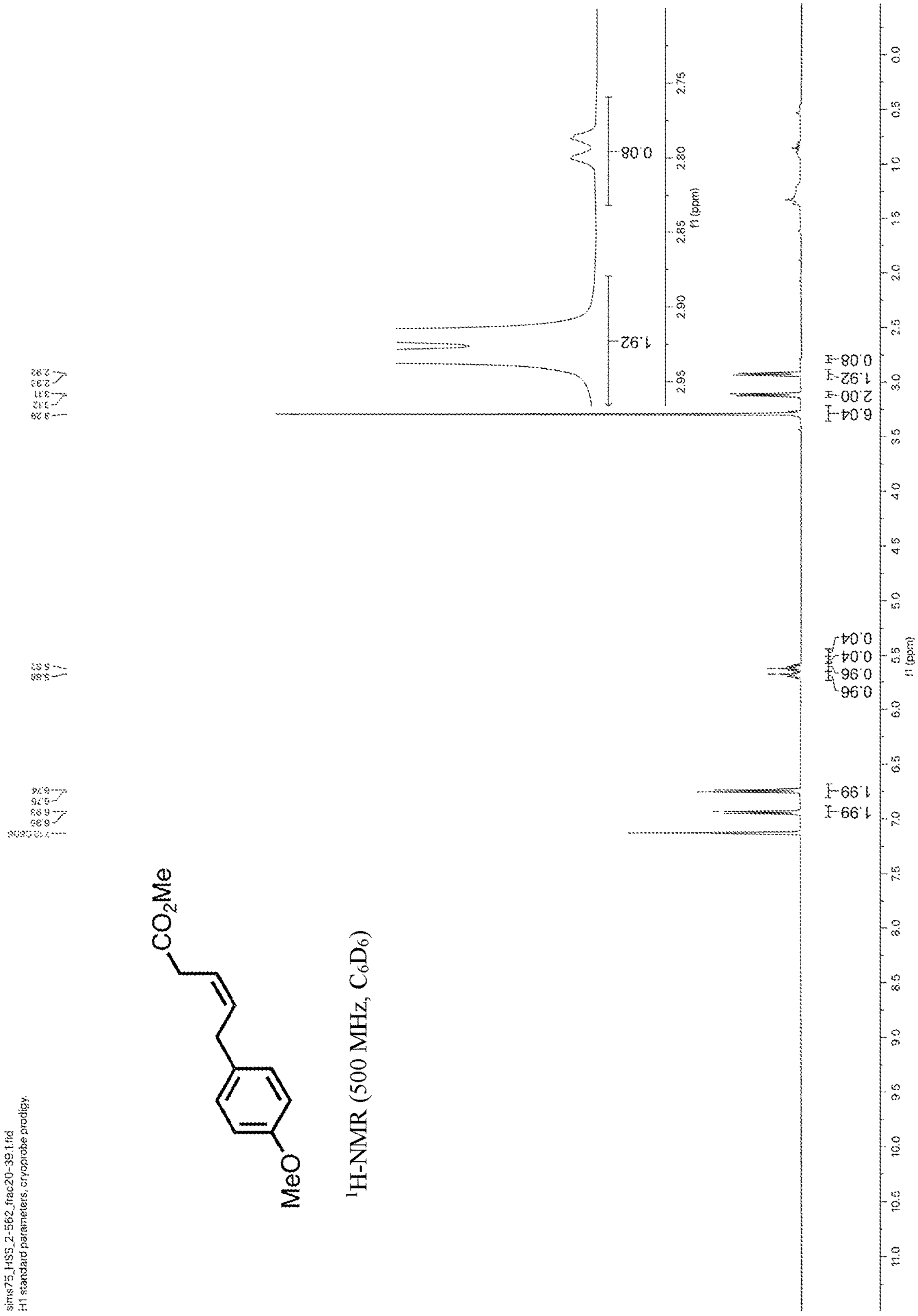
Figure 8:
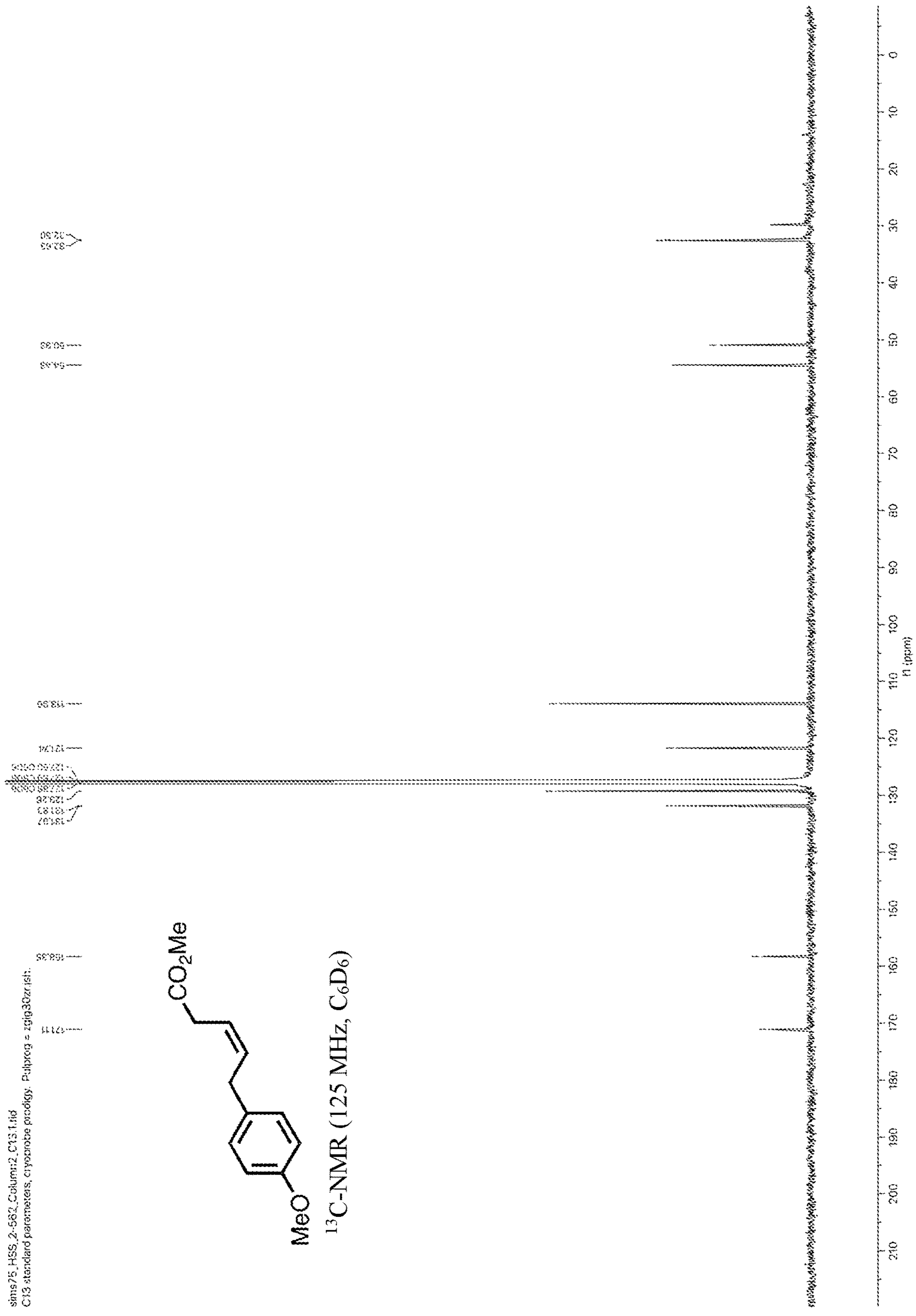
Figure 8:
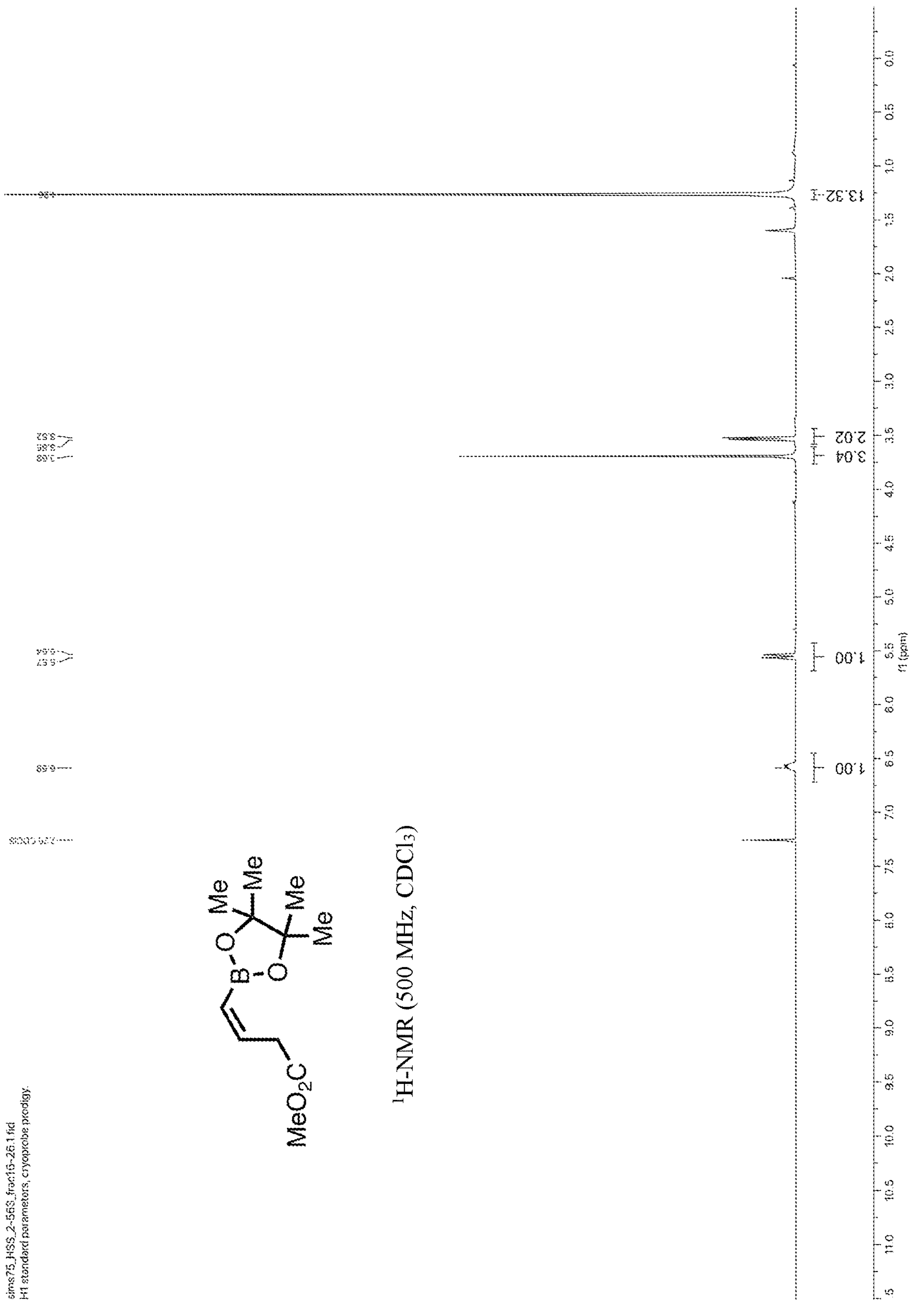
Figure 8:
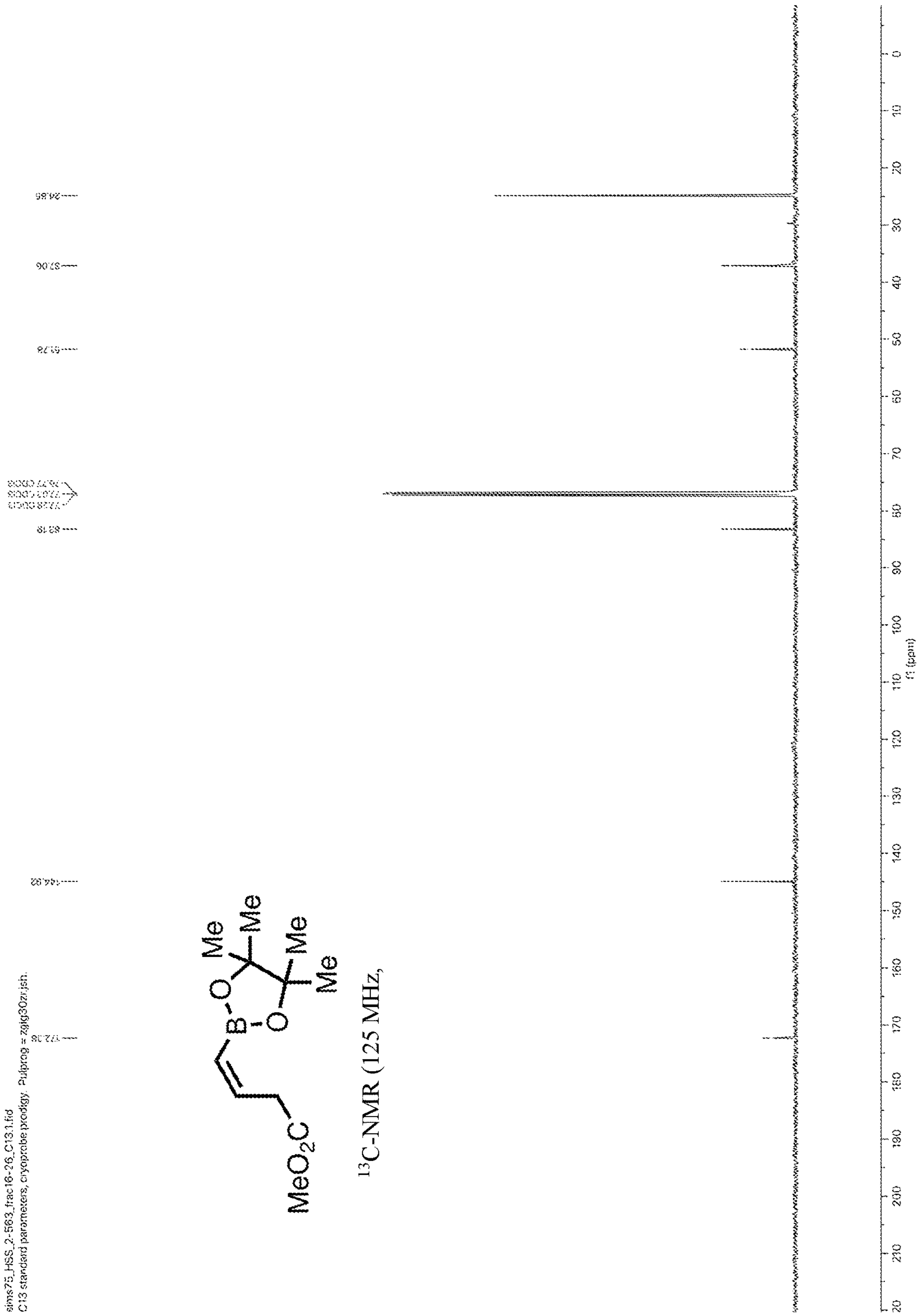
Figure 8:
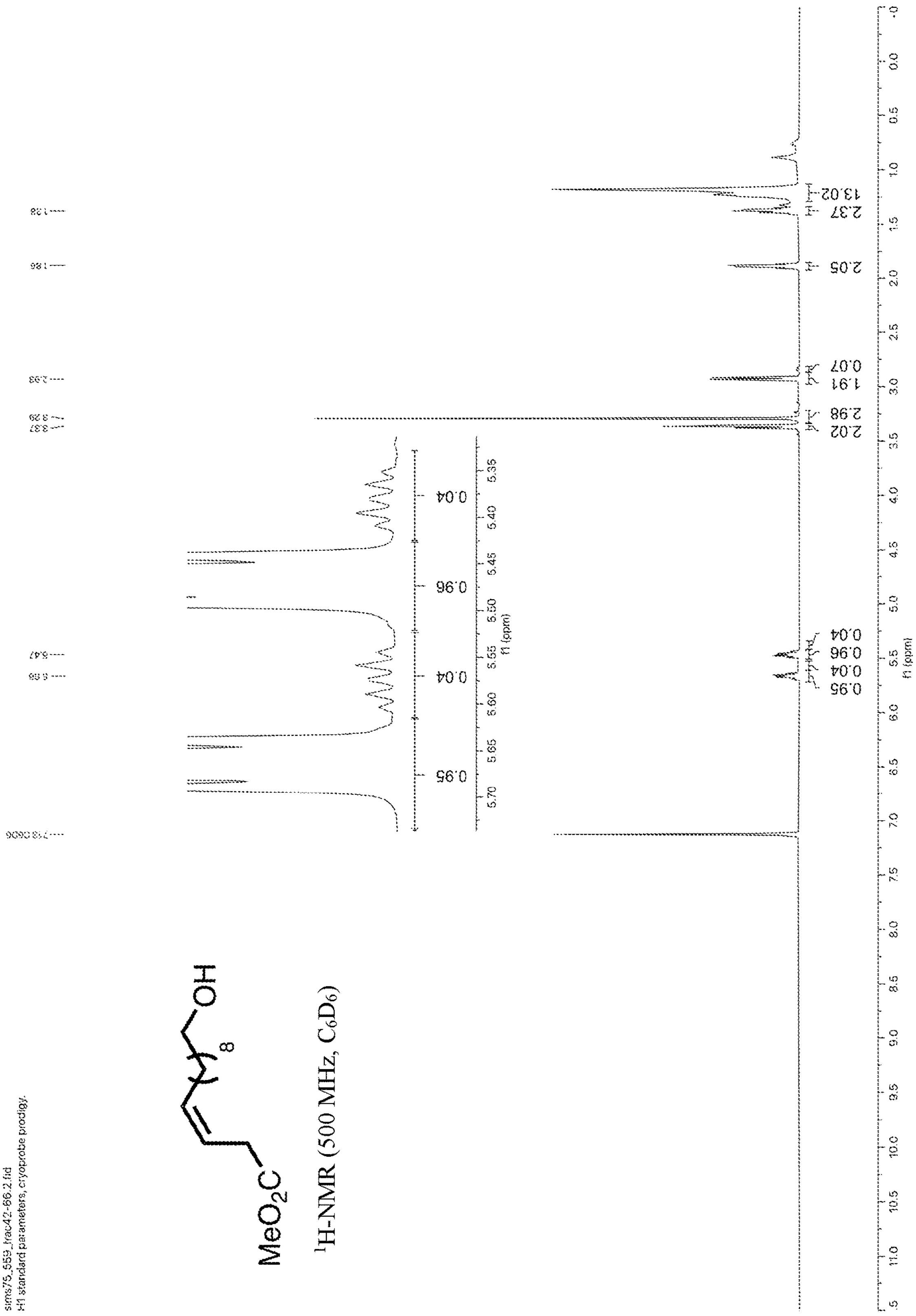
Figure 8:
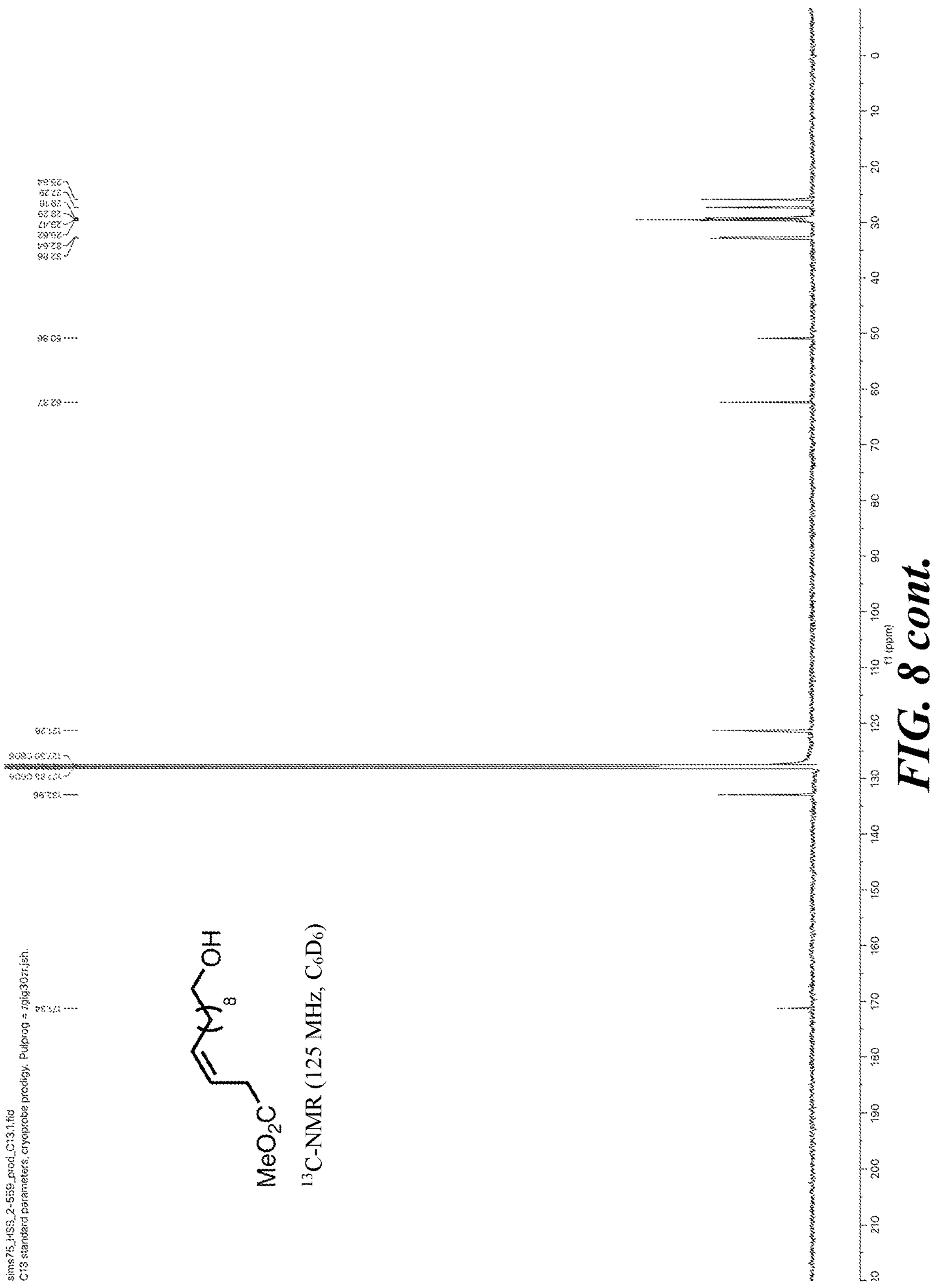
Figure 8:
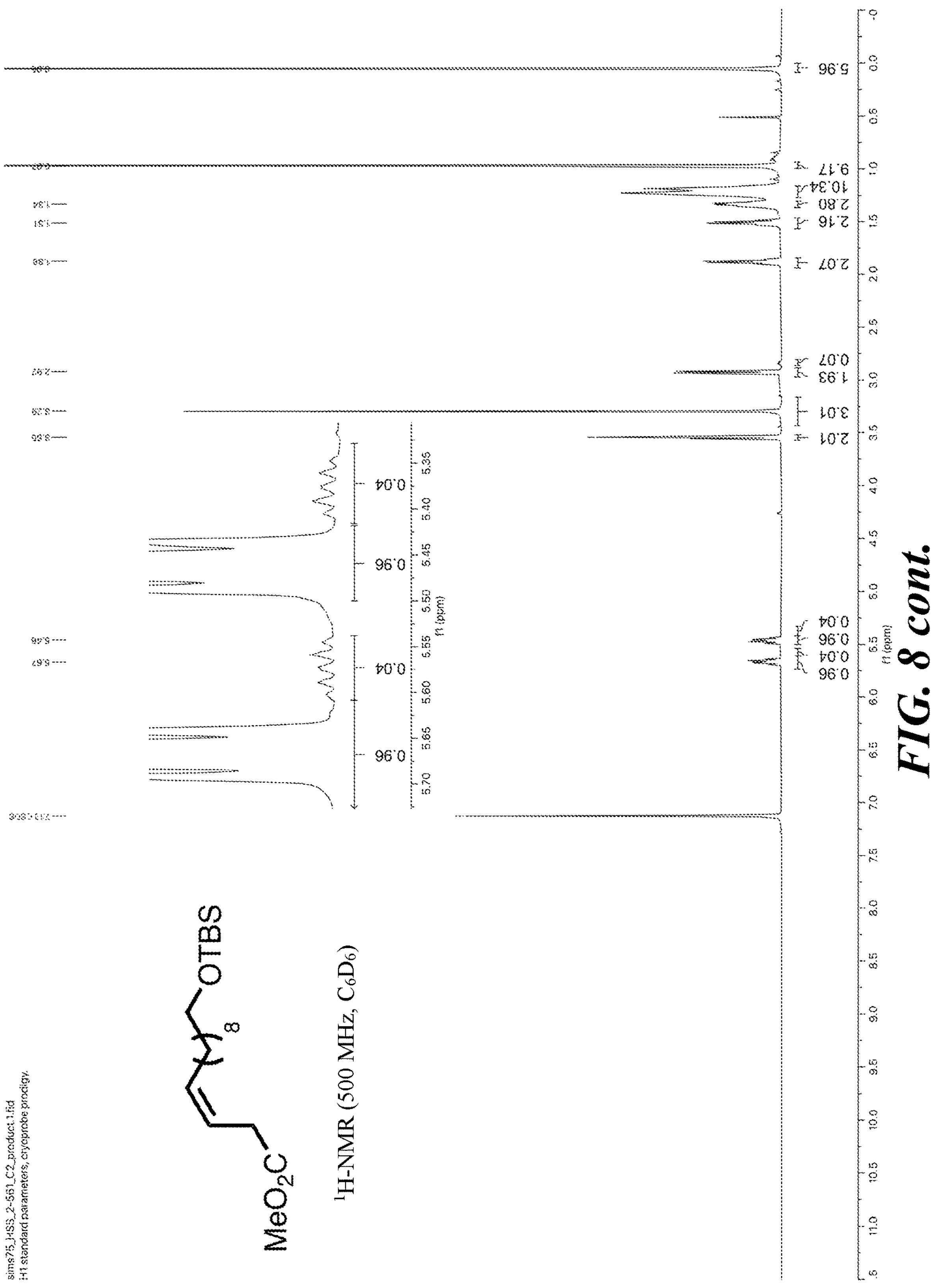
Figure 8:
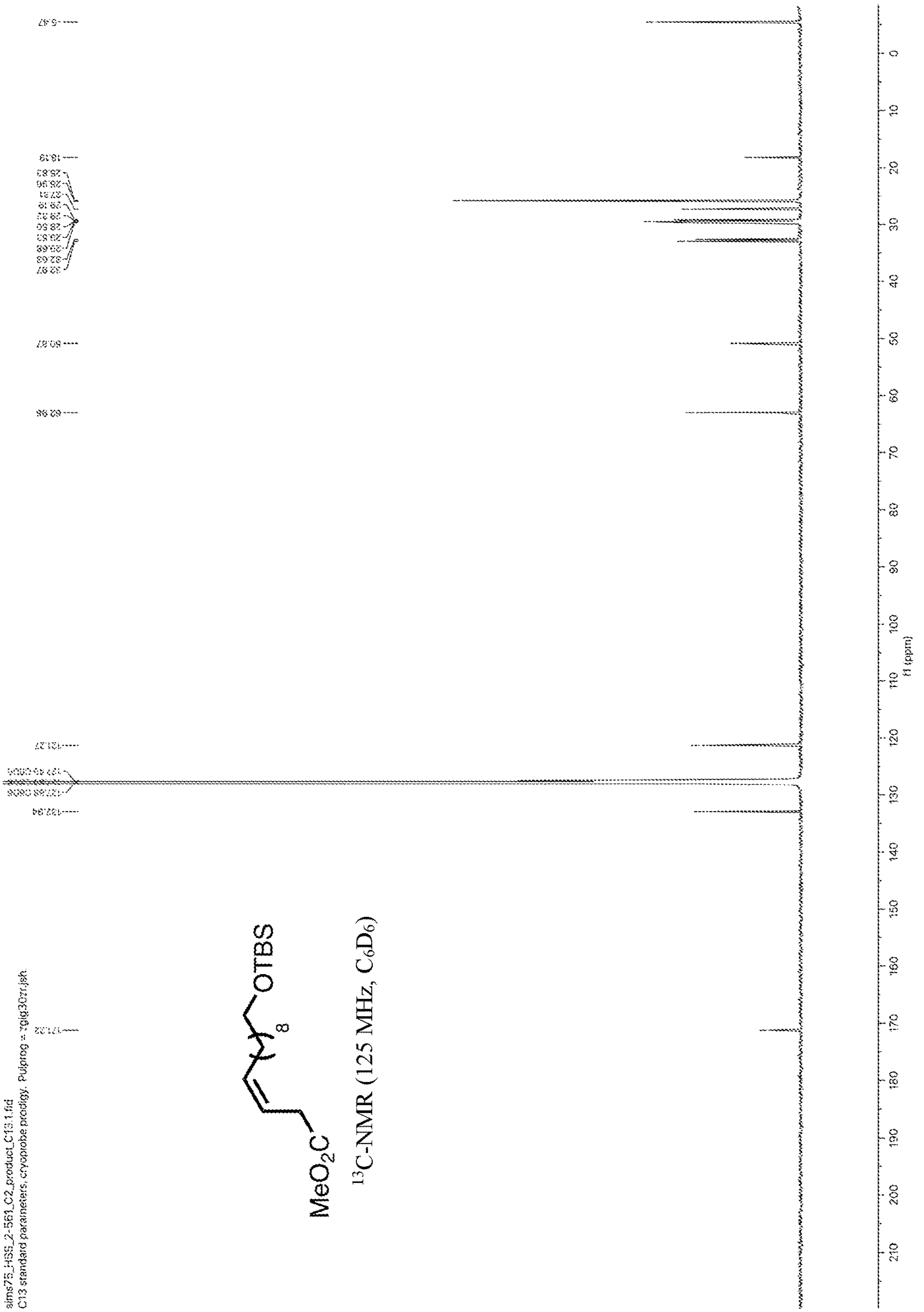
Figure 8:
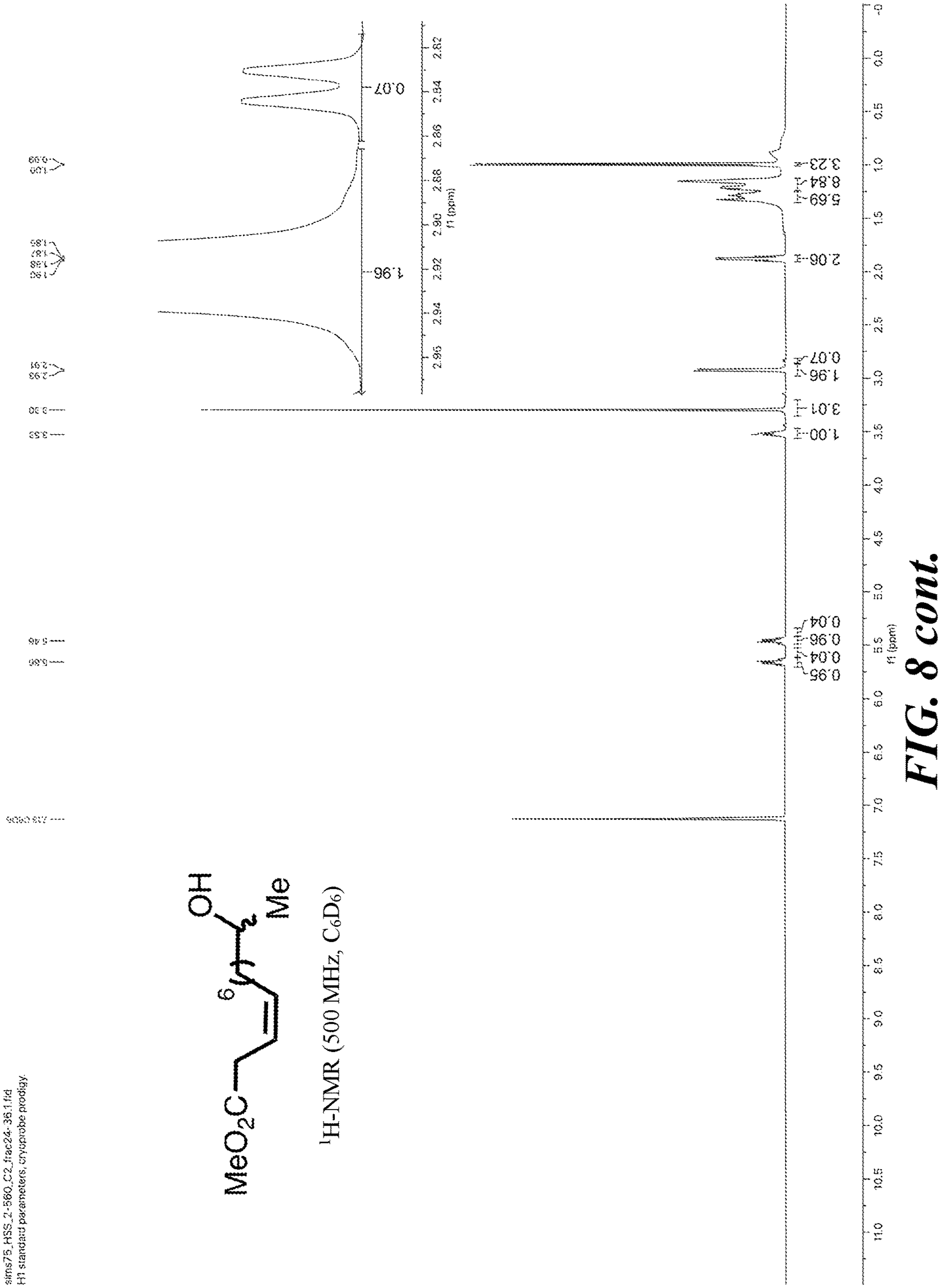
Figure 8:
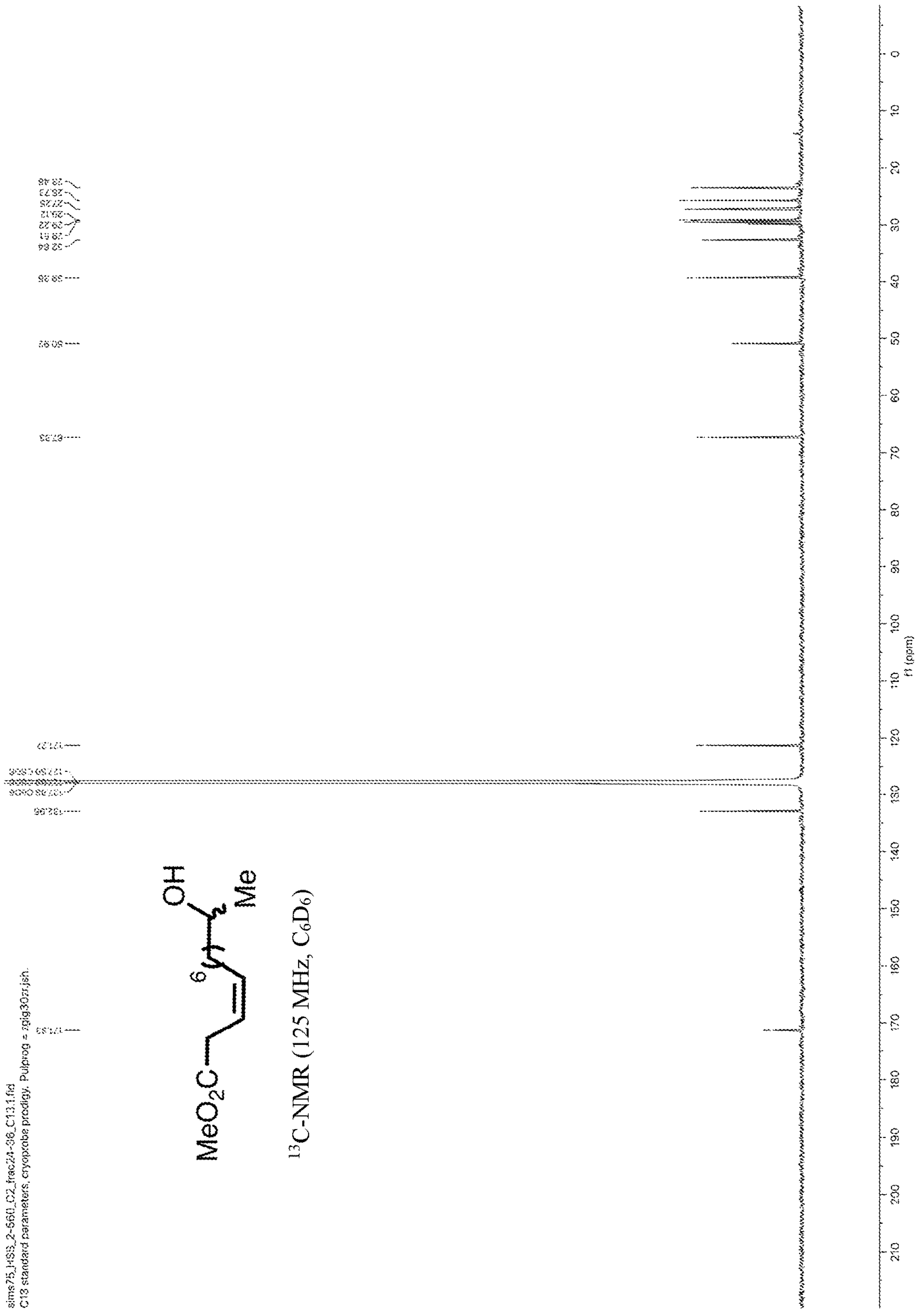

Spectra data for $^1$H and $^{13}$C NMR spectra listed in the above examples are shown in FIG. 8.

The invention claimed is:

1. A method for synthesis of a tricyclic-prostaglandin $D_2$ metabolite (PGDM) methyl ester or a pharmaceutically acceptable salt thereof, the method comprising:

(a) converting a first compound having the structure

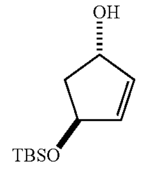 [SMILES: CC(C)(C)[Si](C)(C)O[C@@H]1C=C[C@@H](O)C1]

to an iodo-acetal compound by:

(1) combining the first compound with anhydrous dichloromethane (DCM) and N-iodosuccinimide to form a solution; and (2) adding ethyl vinyl ether to the solution and mixing at about −20° C. for at least 30 minutes and mixing at about 0° C. for at least 4 hours to produce the iodo-acetal compound having the structure

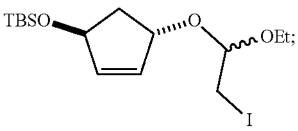 [SMILES: CCOC(CI)O[C@@H]1C=C[C@@H](O[Si](C)(C)C(C)(C)C)C1]

;

(b) subjecting the iodo-acetal compound to either a first cyclization reaction with a methyl ester or a second cyclization reaction with a methyl ester to provide a cyclization product having the structure

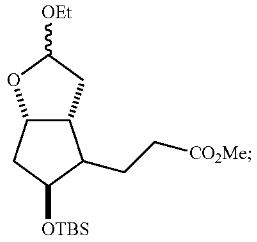

;

wherein the first cyclization reaction comprises:

combining the iodo-acetal compound with 2,2'-azobis (2-methylpropionitrile) (AIBN), sodium cyanoborohydride ($NaCNBH_3$), tert-Butyl alcohol (BuOH), methyl acrylate, and $nBu_3SnCl$ to form an iodo-acetal solution; and heating the iodo-acetal solution to about 85° C. and mixing for at least 72 hours to produce the cyclization product; and wherein the second cyclization reaction comprises:

combining the iodo-acetal compound with nickel (II) chloride ethylene glycol dimethyl ether complex and neocuproine to form a mixture;

stirring the mixture at room temperature for at least 10 minutes, and then to 40° C. for at least 10 minutes; and adding Zn nanopowder and methyl acrylate and stirring at 40° C. for at least 1 hour to produce the cyclization product;

(c) reacting the cyclization product to form a cyclopropanol compound by:

combining the cyclization product with $ClT^{i}(O_{i}Pr)_3$ or titanium tetrachloride/tetra n-butyl titanate ($TiCl_4$) to form a second solution; and adding a Grignard reagent and mixing at about 0° C. for at least one hour and then to room temperature for at least 30 minutes to produce the cyclopropanol compound having the structure

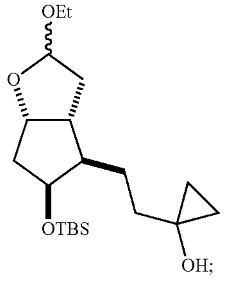

(d) deprotecting the cyclopropanol compound to form a deprotected cyclopropanol compound by:

combining the cyclopropanol compound with anhydrous tetrahydrofuran (THF) to form a third solution and cooling to about 0° C.;

adding tetra-n-butylammonium fluoride (TBAF) and allowing the third solution to warm to room temperature; and mixing the third solution for at least 43 hours to give the deprotected cyclopropanol compound having the structure

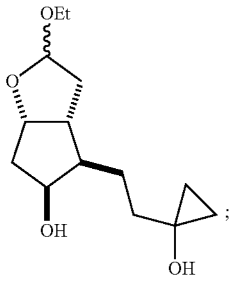

(e) hydrolyzing the deprotected cyclopropanol compound by combining the deprotected cyclopropanol compound with THF and HCl and stirring to form a hemi-acetal compound

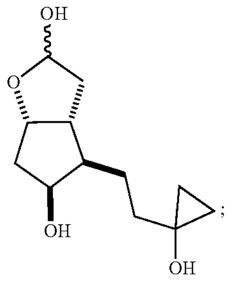

(f) reacting the hemi-acetal compound by:

combining methyltriphenylphosphonium bromide ($CH_3PPh_3Br$) with anhydrous THF, and potassium hexamethyldisilazanide (KHMDS) and mixing at room temperature for at least 1 hour and, subsequently, mixing at about 0° C. for at least another 1 hour to form a cooled ylide solution;

combining the cooled ylide solution and a hemi-acetal solution comprising the hemi-acetal and THF; and stirring the combined hemi-acetal and cooled ylide solution at about 0° C. for at least 37 minutes to form an olefin compound having the structure

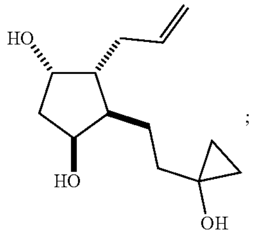 [SMILES: C=CC[C@@H]1[C@@H](CCC2(O)CC2)[C@@H](O)C[C@@H]1O]

(g) subjecting the olefin compound to a carbonylative spirolactonization reaction by:

to form a solution, combining and mixing (1) the olefin compound with anhydrous benzene or anhydrous THE, and 2,3-dichloro-5,6-dicyano-1,4-benzoquinone (DDQ), and (2) palladium(II) acetate ($Pd(OAc)_2$) or palladium(II) trifluoroacetate ($Pd(TFA)_2$; and quenching the solution with triethyl amine (TEA) and mixing for at least 30 minutes to produce a compound having an oxaspirolactone moiety having the structure

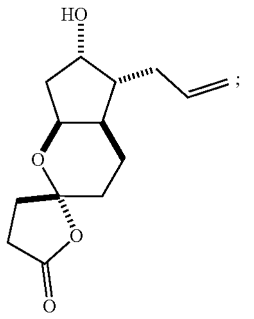

and (h) combining the compound having an oxaspirolactone moiety with a solvent, dichloroethane (DCE) or THF, a molecule having a terminal olefin, and a Z-selective catalyst comprising Ru-Mes or DIPP, and allowing the resulting combination to mix for at least 2 hours at between 30-53° C. to produce tricyclic-PGDM methyl ester or a pharmaceutically acceptable salt thereof;

wherein the molecule having a terminal olefin has the structure

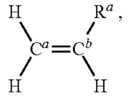

wherein $R^a$ is alkyl, alkenyl, heteroalkyl, heteroalkenyl, aryl, heteroaryl, or acyl.

2. The method of claim 1, wherein the Grignard reagent is selected from the group consisting of: ethyl magnesium bromide, methyl magnesium chloride, and methyl magnesium bromide.

3. The method of claim 1, further comprising quenching hydrolysis with $K_2CO_3$ when at or about 5-10% of the deprotected cyclopropanol compound remains as detected by thin-layer chromatography (TLC).

4. The method of claim 1, further comprising concentrating the hemi-acetal compound with dichloromethane (DCM).

5. The method of claim 1, further comprising monitoring a reaction solution of step (f) to form the olefin compound using thin-layer chromatography (TLC) and quenching the Wittig reaction or olefination upon detection of a byproduct.

6. The method of claim 1, wherein the molecule having a terminal olefin is methyl 3-butenoate.

* * * * *